United States Patent [19]

Freiberg et al.

[11] Patent Number: 5,288,709
[45] Date of Patent: Feb. 22, 1994

[54] ERYTHROMYCIN DERIVATIVES

[75] Inventors: Leslie A. Freiberg, Waukegan; Larry L. Klein, Lake Forest; Clinton M. Yeung, Skokie; Carla M. Edwards, Evanston; David J. Bacino, Waukegan, all of Ill.

[73] Assignee: Abbott Laboratories, Abbott Park, Ill.

[21] Appl. No.: 743,424

[22] PCT Filed: Mar. 28, 1990

[86] PCT No.: PCT/US90/01658

§ 371 Date: Aug. 21, 1991

§ 102(e) Date: Aug. 21, 1991

Related U.S. Application Data

[63] Continuation-in-part of Ser. No. 329,473, Mar. 28, 1989, abandoned.

[51] Int. Cl.$^5$ .................. A61K 31/70; C07H 17/08
[52] U.S. Cl. ............................. 514/29; 536/7.2; 536/7.4
[58] Field of Search ............... 536/7.2, 7.4; 514/29

[56] References Cited

U.S. PATENT DOCUMENTS

| | | | |
|---|---|---|---|
| 3,954,881 | 5/1976 | Bouder | 536/4.1 |
| 3,963,696 | 6/1976 | Marhn et al. | 536/7.2 |
| 4,743,593 | 5/1988 | Hunt | 514/29 |
| 5,008,249 | 4/1991 | Omura et al. | 514/29 |

FOREIGN PATENT DOCUMENTS 1379395 7/1990 European Pat. Off. .

OTHER PUBLICATIONS

Kuduk-Jaworska et al., in *Bull. Acad. Pol. Sci., Ser. Sci. Chim.*, 25(1):73-80 (1977).
Banaszek et al., *Rocz. Chem.*, 43:763-73 (1969).

*Primary Examiner*—Johnnie R. Brown
*Assistant Examiner*—Elli Peselel
*Attorney, Agent, or Firm*—Andreas M. Danckers

[57] ABSTRACT

New 9-deoxo-9,12-epoxy erythromycin derivatives are disclosed which have improved antibacterial properties. Compositions comprising the erythromycin derivatives and methods of treating mammalian patients with the erythromycin derivatives are also disclosed.

5 Claims, No Drawings

ERYTHROMYCIN DERIVATIVES

This is a continuation-in-part of co-pending U.S. application Ser. No. 07/329,473, filed Mar. 28, 1989, now abandoned.

TECHNICAL FIELD

This invention relates to new 9-deoxo-9,12-epoxyerythromycin derivatives having antibacterial properties, compositions comprising the new erythromycin derivatives, and methods of treating mammalian patients therewith.

BACKGROUND OF THE INVENTION

Erythromycin and common derivatives are widely used and exhibit desirable activity against a number of gram-positive pathogens. Since some pathogens are less susceptible than others to these drugs, high doses of these antibiotics are occasionally necessary in the treatment of serious or widespread infections. As with all drugs, toxic effects are sometimes observed at higher dosage levels, particularly in patients who are seriously compromised by infection and thus are most in need of treatment. Unfortunately, improvements in potency and spectrum are often accompanied by an increase in toxicity, so that later generation drugs usually represent a compromise between these competing considerations. As a result, there is a continuing search for antibiotics which are more potent against certain organisms, or preferably, against all organisms, than those currently used. Desirably, such drugs will have an improved therapeutic ratio, which is the ratio of the effective therapeutic or prophylactic dose to the toxic dose, usually expressed in terms of the $ED_{50}/LD_{50}$ ratio.

SUMMARY OF THE INVENTION

This invention relates to 9-deoxo-9,12-epoxyerythromycin A compounds that are useful as broad spectrum antibacterial agents, with activity against gram positive and gram negative bacteria.

The compounds of the invention include those having the following formula I:

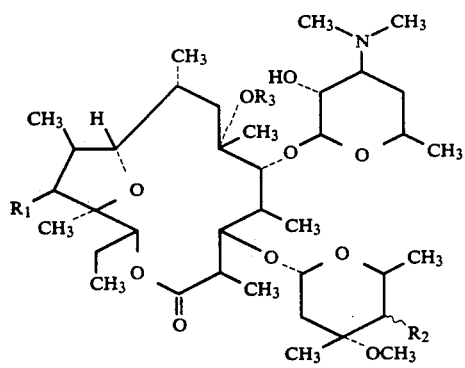

in which
  $R_1$ is an oxo, oxime, hydroxy or amino group at the 11 position;
  $R_2$ is hydrogen, an oxygen-containing group or a nitrogen-containing group at the 4" position; and
  $R_3$ is hydrogen or loweralkyl. The present invention also includes pharmaceutically acceptable salts and esters of the above compounds.

The compositions of the present invention comprise an antibacterially effective amount of a compound of the invention and a pharmaceutically acceptable carrier or diluent.

The method of the present invention includes the treatment of bacterial infections in a mammal in need of such treatment which comprises administering to the mammal an effective amount of a compound of the invention.

DETAILED DESCRIPTION OF THE INVENTION

This invention includes novel 9-deoxo-9,12-epoxyerythromycin A compounds and pharmaceutically acceptable salts and esters thereof. In structural terms, the invention includes compounds of the following formula

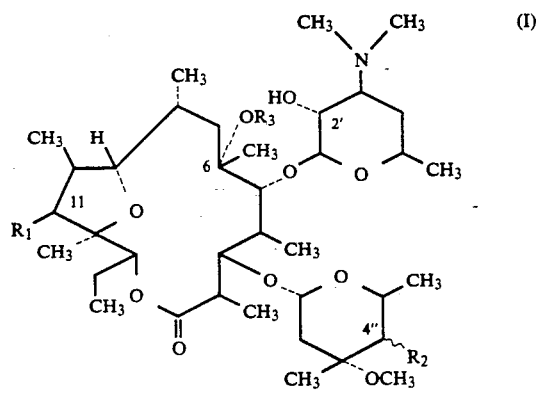

wherein
  $R_1$ is an oxo, oxime, hydroxy, or amino at the 11 position;
  $R_2$ is hydrogen, an oxygen-containing group or a nitrogen-containing group at the 4" position; and
  $R_3$ is hydrogen or loweralkyl; as well as pharmaceutically acceptable salts and esters thereof.

Where position $R_1$ is substituted by a divalent radical, such as oxo, it is understood that a double bond exists between the radical and the carbon at position 11.

This invention also includes antibacterial compositions comprising an antibacterially effective amount of a compound of the invention and a pharmaceutically acceptable carrier or diluent.

This invention further includes a method for treating bacterial infections in a mammal in need of such treatment by administering to the mammal an effective amount of a compound of the invention.

Compounds of this invention offer improved in vitro and in vivo antibiotic potency against certain organisms in comparison to erythromycin. Specific examples of antibiotic potency are disclosed in Tables 2 through 5 hereinbelow.

Compounds that are representative of the preferred class of compounds of this invention include the following compounds as well as their pharmaceutically acceptable salts and esters:
  (9S,11S)-9-Deoxo-12-deoxy-9,12-epoxyerythromycin A;
  (9S)-9-Deoxo-11,12-dideoxy-9,12-epoxy-11-oxoerythromycin A;
  (4"R,9S)-9-Deoxo-4",11,12-trideoxy-9,12-epoxy-11-oxo-4"-[[(phenylmethoxy)carbonyl]amino]erythromycin A;

(4″R,9S)-4″-Amino-9-deoxo-4″,11,12-trideoxy-9,12-epoxy-11-oxoerythromycin A;
(4″R,9S)-9-Deoxo-4″,11,12-trideoxy-9,12-epoxy-4″-[[(dimethyamino)methylene]amino]-11-oxoerythromycin A;
(4″R,9S)-4″-Acetylamino-9-deoxo-4″,11,12-trideoxy-9,12-epoxy-11-oxoerythromycin A;
(4″R,9S)-9-Deoxo-4″,11,12-trideoxy-9,12-epoxy-4″-[(methylsulphonyl)amino]-11-oxoerythromycin A;
(4″R,9S)-9-Deoxo-4″,11,12-trideoxy-9,12-epoxy-11-oxo-4″-[(phenylmethyl)amino]erythromycin A;
(4″R,9S,11S)-4″-Amino-9-deoxo-4″,12-dideoxy-9,12-epoxyerythromycin A;
(4″S,9S)-4″-Amino-9-deoxo-4″,11,12-trideoxy-9,12-epoxy-11-oxoerythromycin A;
(4″S,9S,11S)-4″-Amino-9-deoxo-4″,12-dideoxy-9,12-epoxyerythromycin A;
(4″S,9S)-9-Deoxo-4″,11,12-trideoxy-9,12-epoxy-4″-(methylsulfonyl)amino-11-oxoerythromycin A;
(9S,11S)-4″-O-aminocarbonyl-9-deoxo-12-deoxy-9,12-epoxyerythromycin A;
(9S)-9-Deoxo-11,12-dideoxy9,12-epoxy-11-hydroxyiminoerythromycin;
(9S,11S)-11-Amino-9-deoxo-11,12-deoxy-9,12-epoxyerythromycin A;
(9S,11S)-11-Amino-9-deoxo-4″,11,12-trideoxy-9,12-epoxyerythromyxin A;
(4″R,9S,11S)-4″,11-Diamino-9-deoxo-4″,11,12-trideoxy-9,12-epoxyerythromycin A;
(4″R,9S)-9-Deoxo-11,12-dideoxy-9,12-epoxy-11-oxoerythromycin A;
(4″S,9S,11S)-4″,11-Diamino-9-deoxo-4″,11,12-trideoxy-9,12-epoxyerythromycin A;
(9S,11S)-4″-O-Acetyl-9-deoxo-12-deoxy-9,12-epoxyerythromycin A;
(9S)-4″-O-Aminocarbonyl-9-deoxo-11,12-dideoxy-9,12-epoxy-11-oxoerythromycin A; and
(4″S,9S)-4″-[(Aminocarbonyl)amino]-9-deoxo-4″,11,12-trideoxy-9,12-epoxy-11-oxoerythromycin.

The preferred intermediates for the preparation of the compounds of Formula I are as follows:
9,10-Didehydro-9-deoxo-11,12-dideoxy-9,12-epoxy-11-oxo-4″-O-[(phenylmethoxy)carbonyl]erythromycin A;
2′-O-Acetyl-11-deoxy-11-oxoanhydroerythromycin A;
9,10-Didehydro-9-deoxo-11,12-dideoxy-9,12-epoxy-11-oxoerythromycin A;
(4″E) 9,10-Didehydro-9-deoxo-4″,11,12-trideoxy-9,12-epoxy-4″-hydroxyimino-11-oxoerythromycin A;
(9S,11S)-2′-O-Acetyl-9-deoxo-12-deoxy-9,12-epoxy-11-O-triethylsilyl-4″-O-(2-oxoethyl)erythromycin A; and
9,10-Didehydro-9-deoxo-11,12-dideoxy-9,12-epoxy-6-O-methyl-11-oxoerythromycin A.

The term "oxygen-containing group at the 4″ position" as used herein refers to a hydroxy, oxime, alkanoyloxy, aminoalkoxy, aminocarbonyloxy or carbonate substituent which is attached to the carbon occupying the 4″ position of the cladinose sugar moiety of the erythromycin structure.

The term "nitrogen containing group at the 4″ position" as used herein refers to an amino, oxime, imine, or carbamyl substituent which is attached to the carbon occupying the 4″ position of the cladinose sugar moiety of the erythromycin structure.

The term "at the 11 position" as used herein refers to a substituent which is attached to the carbon occupying the 11 position of the erythromycin structure.

The term "alkanoyl" as used herein refers to —C(O)R$_4$ wherein R$_4$ is a straight or branched chain loweralkyl group. Alkanoyl includes, but is not limited to, acetyl, propionyl, butyryl, isobutyryl and the like. These compounds can be unsubstituted, or they can be substituted provided that any such substituents not interfere with the efficacy of the compound.

The term "alkanoylamino" as used herein refers to —NHC(O)R$_5$ wherein R$_5$ is a loweralkyl group.

The term "alkanoyloxy" as used herein refers to —OC(O)R$_6$ wherein R$_6$ is a loweralkyl such as, for example, —OC(O)CH$_3$.

The term "alkoxy" as used herein refers to —OR wherein R is a loweralkyl group including, but not limited to, methoxy, ethoxy and the like. These compounds can be unsubstituted, or they can be substituted provided that any such substituents not interfere with the efficacy of the compound.

The term "alkoxyalkyl" as used herein refers to a loweralkyl radical substituted with one or more alkoxy groups.

The term "amine" or "amino" as used herein refers to unsubstituted as well as mono- or di-substituted amine substituents of the formula —NR$_7$R$_8$, provided that any such substituents not interfere with the efficacy of the compound. Further, it is contemplated R$_7$ and R$_8$ taken together can form a ring containing from 3 to 8 atoms which can include carbon or heteroatoms selected from N, O or S that together form a heterocyclic ring which can itself be substituted. Selection of such substituents is a routine laboratory determination, given the present disclosure. For example, R$_7$ and R$_8$ can independently include acetyl, aryl, aryl carbonyl, sulfonyl and loweralkyl substituents all of which can be further substituted provided that the substituents not interfere with the efficacy of the compound. The preferred substituted amines include, but are not limited to piperidinyl, alkanoylamino, benzylamino, methylsulfonylamino, —NHCH$_3$, —NH(CH$_3$)$_2$ and —N(CH$_3$)CH$_2$CH$_2$N(CH$_3$)$_2$.

The term "aminoalkyl group" is used herein to mean an amine group appended to a loweralkyl radical.

The term "aminocarbonyloxy" as used herein refers to —OC(O)NR$_9$R$_{10}$ wherein R$_9$ and R$_{10}$ are independently selected from hydrogen and loweralkyl such as, for example, —OC(O)NH$_2$.

The term "aminoalkoxy" is used herein to mean —OR$_{11}$ wherein R$_{11}$ is an aminoalkyl- group including, but not limited to, 2-aminoethoxy, N methyl-N benzyl-2-aminoethoxy, N-benzyl-2-aminoethoxy, and —OCH$_2$CH$_2$N(CH$_3$)$_2$.

The term "aryl" is used herein to mean aromatic radicals having five or six atoms in a single ring system which may contain one to three hetero atoms selected from S, O and N, the remaining atoms being carbon atoms. Representative aromatic radicals include phenyl, pyridyl, pyrazinyl, thiazoyl, furyl, and thienyl. Further, the single ring system may be substituted to form a multiple fused ring system, as for example 1-naphthyl, 2-naphthyl and the like. These compounds can be unsubstituted, or they can be substituted provided that any such substituents not interfere with the efficacy of the compound.

The term "carbamyl" as used herein refers to —NHC(O)OR$_{12}$ wherein R$_{12}$ is an arylalkyl such as, for example, benzylcarbamyl, or a loweralkyl.

The term "carbonate" as used herein refers to —OC(O)OR$_{13}$ wherein R$_{13}$ is an arylalkyl or a loweralkyl.

The term "cycloalkyl" as used herein refers to a three to seven carbon cyclic group. These compounds can be unsubstituted, or they can be substituted provided that any such substituents not interfere with the efficacy of the compound.

The term "enone" as used herein refers to an erythromycin derivative having an alpha beta unsaturated 11 ketone with a double bond in the 9-10 position. An example of an enone is seen in Scheme II, compound 6.

The term "imine" as used herein refers to —C=NR$_{14}$ wherein R$_{14}$ is a loweralkyl which can be substituted such as, for example, —N=CHN(CH$_3$)$_2$.

The term "loweralkyl" is used herein to mean straight or branched chain radicals of one to eight carbon atoms. Representative of such radicals are methyl, ethyl, n-propyl, isopropyl, n-butyl, sec-butyl, isobutyl, tert-butyl, 2-ethylhexyl, n-octyl, 2,4-dimethylpentyl and the like. These can be unsubstituted, or they can be substituted as, for example, with loweralkyl, cycloalkyl or aryl groups, provided they not interfere with the efficacy of the compound.

The term "oxo" as used herein refers to =O.

The term "oxime" as used herein refers to —C=NOH.

The term "sulfonyl" as used herein refers to —S-(O)$_2$R$_{15}$ wherein R$_{15}$ is aryl or loweralkyl. These compounds can be unsubstituted, or they can be substituted provided that any such substituents not interfere with the efficacy of the compound.

The term "protecting group" as used herein refers to those groups intended to protect against undesirable reactions during synthetic procedures. Such protecting groups are well known to those skilled in the art.

Contemplated equivalents of the compounds of general Formula I are compounds otherwise corresponding thereto and having the same general properties wherein one or more of R$_1$, R$_2$, and R$_3$ are simple variations of the substituents as defined herein. As will be apparent, where a substituent can be a hydrogen atom, the exact chemical nature of a substituent which is other than hydrogen at that position is not critical, so long as it does not adversely affect the efficacy of the compound.

By "pharmaceutically acceptable" is meant those salts and esters which are, within the scope of sound medical judgment, suitable for use in contact with the tissues of humans and lower animals without undue toxicity, irritation, allergic response and the like, commensurate with a reasonable benefit/risk ratio, and effective for their intended use in the chemotherapy and prophylaxis of antimicrobial infections. The salts can be prepared in situ during the final isolation and purification of the compounds of Formula (I), or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarare, succinate, tartrate, ascorbate, glucoheptonate, lactobionate, lauryl sulphate salts and the like. Representative alkali or alkaline earth metal salts include the sodium, calcium, potassium and magnesium salts, and the like.

Certain compounds of the invention exist in optically active forms. The pure R and S isomers, as well as racemic and other mixtures thereof, are contemplated by the invention. Additional asymmetric carbon atoms may be present in a substituent such as a loweralkyl group. All such isomers as well as mixtures thereof are intended to be included in the invention. In particular, stereochemistry of the substituent at the 4" position (R$_2$) can be either axial or equatorial unless specifically noted otherwise.

The compounds of the present invention can be administered to humans and animals either orally, rectally, parenterally, by inhalation spray, or topically in dosage unit formulations containing conventional non-toxic pharmaceutically acceptable carriers, adjuvants and vehicles as desired.

The term "parenteral" as used herein includes subcutaneous, intravenous, intramuscular, and intraarticular injection and infusion techniques.

The term "administration" of the antibiotic or composition herein includes systemic use, as by intramuscular, intravenous, intraperitoneal or subcutaneous injection and continuous intravenous infusion, and oral administration thereof, as well as topical application of the compounds and compositions to the site of infection or potential infection.

This invention also provides pharmaceutical compositions in unit dosage form, comprising a therapeutically effective amount of a compound of this invention in combination with a conventional pharmaceutical carrier.

By "a therapeutically effective amount" of the antibiotic herein is meant a sufficient amount of the compound to treat or prevent susceptible bacterial or other microbial infections, at a reasonable benefit/risk ratio applicable to any medical treatment. Of course, the total daily usage of the compositions herein will be decided by the attending physician within the scope of sound medical judgment. The effective amount of the antibiotic of this invention will vary with the particular organism being treated, the severity of the infection, the duration of the treatment, the specific compound, ester or salt employed, the age and weight of the patient and like factors well-known in the medical arts.

This invention also includes pharmaceutical compositions in unit dosage form, comprising a therapeutically effective amount of a compound of this invention in combination with a conventional pharmaceutical carrier.

Total daily dose of the compounds of this invention administered to a host in single or divided doses can be in amounts, for example, from 0.01 to 500 mg/kg body weight daily and more usually 0.1 to 15 mg/kg body weight daily. Single dose compositions can contain such amounts or submultiples thereof to make up the daily dose. In general, treatment and prevention regimens according to the present invention comprise administration to a patient in need of such treatment from about 100 mg to about 2000 mg. of the compound of this invention per day in multiple doses or, preferably, in a single dose of from 250 mg to about 1000 mg.

It will be understood, however, that the specific therapeutically effective dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The present invention includes one or more of the compounds of the invention formulated into compositions together with one or more non toxic pharmaceutically acceptable carriers, adjuvants or vehicles (which are collectively referred to herein as carriers) for parenteral injection, oral administration in solid or liquid form, rectal administration, and the like.

Non-toxic, inert pharmaceutically suitable carriers include solid, semi solid or liquid diluents, fillers and formulation auxiliaries of all types.

As used herein, the term "pharmaceutically acceptable carriers" means a solid or liquid filler, diluent or encapsulating material. Some examples of the materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that can be combined with the carrier materials to produce a single dosage form will vary depending upon the host treated and the particular mode of administration.

Injectable preparations such as sterile injectable aqueous or oleagenous suspensions can be formulated according to the known art using suitable dispersing or wetting agents and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's injection, U.S.P. and isotonic sodium chloride solution. In addition, sterile, fixed oils are conventionally employed as a solvent or suspending medium. For this purpose any bland fixed oil can be employed including synthetic and semisynthetic mono-, di- or triglycerides. In addition, fatty acids such as oleic acid find use in the preparation of injectables.

Suppositories for rectal administration can be prepared by mixing the drug with a suitable non-irritating excipient such as cocoa butter or a polyethylene glycol which is solid at ordinary temperatures but liquid at the rectal temperature and will therefore melt in the rectum and release the drug.

Solid dosage forms for oral administration can include capsules, tablets, pills, powders, prills and granules. In such solid dosage forms, the active compound can be admixed with at least one inert diluent such as sucrose, lactose or starch. Such dosage forms can also comprise, as is normal practice, additional substances other than inert diluents, e.g., tableting lubricants and other tableting aids such as magnesium stearate and microcrystalline cellulose. In the case of capsules, tablets and pills, the dosage forms can also comprise buffering agents. Tablets and pills can additionally be prepared with enteric and other release-controlling coatings.

Liquid dosage forms for oral administration can include pharmaceutically acceptable emulsions, microemulsions, solutions, suspensions, syrups and elixirs containing inert diluents commonly used in the art such as water. Such compositions can also comprise adjuvants such as wetting agents, emulsifying and suspending agents, and sweetening, flavoring and perfuming agents.

If desired, the compounds of the present invention can be incorporated into slow release or targeted-delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

The active compounds can also be in micro-encapsulated form with one or more excipients as noted above.

Dosage forms for topical administration of a compound of this invention further include ointments, pastes, creams, gels, powders, sprays and inhalants. The active component is admixed under sterile conditions with a pharmaceutically acceptable carrier and any needed preservatives or buffers as may be required. Opthalological formulations, ear drops, eye ointments, powders and solutions are also contemplated as being within the scope of this invention.

The ointments, pastes, creams and gels may contain, in addition to an active compound of this invention, excipients such as animal and vegetable fats, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

In general, the compounds of this invention are synthesized by reaction schemes I through XII as illustrated below. It should be understood that $R_1$, $R_2$, and $R_3$ as used herein correspond to the R groups identified by Formula I.

SCHEME I

The compounds of Formula IA are synthesized by the method discussed herein. Erythromycin A (1) is protected from oxidation at the 2'-hydroxyl group by a protecting group, for example, acetylation using acetic anhydride with or without a proton acceptor such as sodium or potassium bicarbonate, or triethylamine (TEA) in an inert solvent such as methylene chloride ($CH_2Cl_2$) or acetonitrile ($CH_3CN$). The 4"-hydroxyl group is protected from oxidation with a reactive phenylmethoxycarbonyl (CBZ) compound such as benzyl chloroformate, in the presence of a proton acceptor such as N,N-dimethylaminopyridine (DMAP) in an inert solvent such as $CH_2Cl_2$ or $CH_3CN$. The resulting 2'-O-acetyl-4"-O-CBZ erythromycin derivative is converted to the anhydroerythromycin A derivative (2) by treatment with a readily ionizable acid, such as hydrochloric acid (HCl) in aqueous solution. Compound 2 is treated with an oxidizing agent such as N-chlorosuccinimide (NCS)/dimethyl sulfide (DMS) in an inert solvent such as toluene and/or $CH_2Cl_2$ to yield the corresponding protected 11-oxo-anhydroerythromycin A derivative. This compound is subsequently converted to the deacetylated unsaturated ketone (3) by treatment with an acid-base catalyst such as hydroxylamine or ammonium acetate in a polar solvent such as methanol (MeOH). The derivative (3) may also be described as an enone. The unsaturated ketone is reduced to the saturated derivative by treatment with a hydride reducing agent such as lithium borohydride ($LiBH_4$), preferably in an ethereal solvent such as tetrahydrofuran (THF) or diethyl ether ($Et_2O$). The 11-hydroxyl group is released from the borate esters formed in the reduction by treatment with methanol. In order to protect the 2'-position during subsequent selective derivatization of the 4"-hydroxyl, the 2'-hydroxyl group is reacetylated in the same manner as described above. The 11-hydroxyl group is then protected from derivatization with a trialkylsilyl group which is attached by reaction with a silating agent such as trimethylsilyl chloride (TMSCl) or triethylsilyl chloride (TESCl) in the presence of a proton acceptor such as imidazole (Im) or pyridine in an inert solvent such as $CH_2Cl_2$. The 4"-O-CBZ group is removed by hydrogenolysis with a catalyst such as palladium on carbon (Pd/C) in a non-reactive solvent such as isopropyl alcohol (IPA) and/or ethyl acetate (EtOAc) to yield compound 4. Compound 4 is converted to protected IA by derivatization of the 4"-hydroxyl group with a reactive carbonyl compound such as acetic anhydride or N,N'-carbonyldiimidazole, in the presence of a proton acceptor such as TEA or DMAP, in an inert solvent such as $CH_2Cl_2$. The product of the reaction of the Compound 4 with carbonyldiimidazole can be hydrolyzed under basic conditions to the carbamate with a base such as ammonium hydroxide in an inert solvent such as acetonitrile ($CH_3CN$). The removal of the 2'-O-acetyl protecting group is accomplished, for example, by treatment with methanol and a weak base such as triethylamine. The silyl protecting group is removed with tetrabutylammonium fluoride in a polar solvent such as THF to give Compound IA. If the epi isomer of Compound IA is preferred, it can be obtained by the above method starting with the appropriate isomer of the starting material. In the preferred embodiments of IA, $R_1$=hydroxy; $R_2$=hydroxy, —OC(O)CH$_3$, or —OC(O)NH$_2$; and $R_3$=hydrogen.

SCHEME II

Scheme II illustrates the preferred process for the preparation of (9S,11S)-9-deoxo-12-deoxy-9,12-epoxyerythromycin A and (9S)-9-deoxo-11,12-dideoxy-9,12-epoxy-11-oxoerythromycin A. A more detailed discussion is described in Examples 4 and 5, Method A.

Erythromycin A is converted to anhydroerythromycin A by treatment with a readily ionizable acid, such as HCl in aqueous solution. The 2'-hydroxyl group of anhydroerythromycin A is protected for the subsequent oxidation step as described in Scheme I. The anhydroerythromycin A derivative (5) is then converted to an unsaturated ketone (6) by treatment with an oxidizing agent such as chromic acid or tetrapropylammonium perruthenate (TPAP) and N-methylmorpholine N-oxide (NMO), followed by treatment with an acid base catalyst such as hydroxylamine or ammonium acetate in a polar solvent such as MeOH. At this point, the derivative (6) is best described as an enone, an alpha-beta unsaturated 11 ketone with a double bond in the 9-10 position. The enone (6) is converted to II (wherein $R_1$=hydroxy) by treatment with a strong hydride reducing agent such as lithium borohydride ($LiBH_4$) or to II (wherein $R_1$=oxo) by treatment with a mild hydride reducing agent such as diisobutylaluminum hydride (DIBAH), preferably in an ethereal solvent such as $Et_2O$ or THF. The 11-hydroxyl group formed in the reduction step with $LiBH_4$ is released from its borate esters by treatment with methanol. In the preferred embodiments of II, $R_1$=oxo or hydroxy; $R_2$=hydroxy; and $R_3$=hydrogen.

Compound II ($R_1$=oxo) can be further derivatized in the 4"-hydroxyl position as described in Scheme I for Compound 4 to give IIA. In the preferred embodiments of IIA, $R_1$=oxo; $R_2$=—OC(O)NH$_2$; and $R_3$=hydrogen.

Alternatively, the 4"-hydroxyl group of the anhydroerythromycin A derivative (5) can also be protected with a CBZ group, as described in Scheme I, prior to oxidation. After oxidation and treatment with an acid-base catalyst to produce the unsaturated ketone, the CBZ-protecting group is removed from the 4" position to give compound 6 which is then converted to II as described above.

SCHEME III

The compounds of Formula III are synthesized by the method discussed herein. 6-O-Methyl erythromycin A (7) is converted to an 11-oxo-erythromycin A-9,12-hemiacetal derivative (8) by treatment with oxalyl chloride and dimethyl sulfoxide (DMSO) in an inert solvent such as $CH_2Cl_2$. Both the 2'- and the 4"-hydroxyl groups are protected from oxidation and deprotected in the same manner as discussed in Scheme I. The erythromycin derivative (8) is converted to the unsaturated ketone (9) by treatment with hydrogen, in the presence of a catalyst such as Pd/C (to remove the 4"-O-CBZ protecting group), in a basic solution such as ammonia in a polar solvent such as MeOH. The 2'-hydroxyl protecting group is removed simultaneously with the elimination reaction. The unsaturated ketone (9) is converted to III by reduction using a hydride reducing agent such as $LiBH_4$ or DIBAH, preferably in an ethereal solvent such as $Et_2O$ or THF. In the preferred embodiments of III, $R_1$=hydroxy or oxo; $R_2$=hydroxy; and $R_3$=—CH$_3$.

SCHEME IV

The compounds of Formula IV are synthesized by the method discussed herein. Erythromycin A (1) is converted to compound 4A (wherein the protecting group is a triethylsilyloxy) group as discussed in Scheme I. The 4"-O-allyl derivative (10) is prepared by treatment with an allylic halide such as allyl bromide and sodium bis(trimethylsilyl) amide in a polar solvent such as dimethyl formamide (DMF). The allyl derivative (10) is converted to the aldehyde (11) by conversion to the diol with an oxidizing agent such as osmium tetroxide ($OsO_4$) followed by treatment with sodium metaperiodate ($NaIO_4$) in aqueous THF. The aldehyde (11) is converted to IV by reductive amination using an amine such as ammonia or dimethylamine or N-methyl-N-benzylamine or benzylamine and a reducing agent such as sodium cyanoborohydride ($NaBH_4CN$) in a solvent such as $CH_3CN$ or aqueous $CH_3CN$ in the presence of an acid such as acetic acid. The 2'-O-acetyl and triethylsilyl protecting groups are removed as discussed in Scheme 1. In the preferred embodiments of IV, $R_1$=hydroxy; $R_2$=—O(CH$_2$)$_2$NH$_2$, or —O(CH$_2$)$_2$NHbenzyl, —O(CH$_2$)$_2$N(CH$_3$)$_2$, —O(CH$_2$)$_2$N(CH$_3$)benzyl; and $R_3$=hydrogen.

SCHEME V

The compounds of Formula V are synthesized by the method discussed herein. The anhydroerythromycin A derivative (5) is converted to the unsaturated ketone derivative (12) by treatment with an oxidizing agent such as NCS/DMS or DMSO/oxalyl chloride in an inert solvent such as toluene or CH$_2$Cl$_2$, followed by treatment of the intermediate 4",11-dideoxy-4",11-dioxo product with hydroxylamine hydrochloride in the presence of a base such as TEA in a polar solvent such as MeOH. The latter reaction also removes the 2'-hydroxyl protecting group. The unsaturated ketone 4"-oxime derivative (12) is then reduced to compound 13 by treatment with a hydride reducing agent such as LiBH$_4$ in a polar solvent such as dimethoxyethane (DME). The 4"-oxime derivative (13) is converted to V by the following sequence of procedures: 1.) reduction of the oxime group with hydrogen in the presence of a catalyst such as Pd/C, in an acidic solvent such as 10% glacial acetic acid in MeOH or in the presence of a catalyst such as Raney nickel in a polar solvent such as 10% concentrated ammonium hydroxide in MeOH; 2.) derivatization of the resultant 4"-amino group with a CBZ group by reaction with N-benzyloxycarbonyloxy succinimide in an inert solvent such as CH$_2$Cl$_2$ or CH$_3$CN; 3.) chromatographic separation of the isomeric N-CBZ derivatives; and 4.) removal of the N-CBZ group from each isomeric 4"-amine by hydrogenolysis with a catalyst such as Pd/C or Raney nickel in a polar solvent such as MeOH or EtOH. In the preferred embodiments of V, $R_1$=hydroxy; $R_2$=—NH$_2$; and $R_3$=hydrogen.

SCHEME VI

The compounds of Formula VI are synthesized by the method discussed herein. The 4"-oxime derivative (12) is hydrogenated, in the presence of a catalyst such as Raney nickel, in a polar solvent such as MeOH or IPA, with or without 5-10% concentrated ammonium hydroxide added. The resultant isomeric amine products are separated as their N—CBZ derivatives, which are prepared as discussed in Scheme V. The (4"R)-isomer of the CBZ-protected amine is converted to a saturated ketone derivative (14) by treatment with a mild hydride reducing agent such as DIBAH, preferably in an ethereal solvent such as THF. The (4"R)-4"-N-CBZ amino derivative (14) is converted to the corresponding (4"R)-4"-amino derivative (15) by removal of the CBZ group as discussed in Scheme V. The (4"R)-4"-amino derivative (15) is converted to VI by any of the following sequence of reactions: 1.) reductive amination of an aldehyde such as benzaldehyde, 1,5-pentanedial, formaldehyde or N-CBZ-N-methyl-2-aminoacetaldehyde with compound 15 in the presence of a reducing agent such as NaBH$_3$CN or with hydrogen and a catalyst such as Pd/C; 2.) treatment of compound 15 with dimethylformamide dimethyl acetal in an inert solvent such as CH$_2$Cl$_2$; 3.) acetylation of compound 15 using acetic anhydride in a polar solvent such as MeOH; and 4.) sulfonation of compound 15 with a sulfonating agent such as methanesulfonyl anhydride and a base such as sodium or potassium carbonate, in an inert solvent such as CH$_2$Cl$_2$; or 5.) treatment of compound 15 with a reactive carbonyl compound, such as N,N'-carbonyldiimidazole, in the presence or absence of a proton acceptor, such as TEA or DMAP, in an inert solvent, such as CH$_2$Cl$_2$, followed by hydrolysis under basic conditions to the urea with a base, such as ammonium hydroxide, in an inert solvent, such as CH$_3$CN. In the preferred embodiments of VI, $R_1$=oxo; $R_2$=—NR$_7$R$_8$, wherein R$_7$ and R$_8$ together form —CH$_2$—CH$_2$—CH$_2$—CH$_2$—, or are separately defined as follows: R$_7$=H and R$_8$=benzyl, or R$_7$ and R$_8$=—CH$_3$, or R$_7$=H and R$_8$=acetyl; or $R_2$=—NCH$_3$(CH$_2$)$_2$N(CH$_3$)$_2$; or $R_2$=—NHS(O)(O)CH$_3$; or $R_2$=—N=CHN(CH$_3$)$_2$; and $R_3$=hydrogen.

SCHEME VII

The compounds of Formula VII are synthesized by the method discussed herein. Scheme VII is identical to Scheme VI with the following exception: the S-isomer of the 4"—N—CBZ-amino derivative (16) and subsequently the S-isomer of the 4"-amino derivative (17) are prepared, preferably by hydrogenation of the 4"-oxime in the presence of ammonium hydroxide. The (4"S)—4"-amino derivative (17) is converted to VII by the same reactions discussed in Scheme VI for the conversion of the (4"R)—4"-amino derivative (15) to VI. In the preferred embodiments of VII, $R_1$, $R_2$ and $R_3$ are defined as for the preferred embodiments of VI.

SCHEME VIII

The compounds of Formula VIII are synthesized by the method discussed herein. The 9,12-epoxy derivative of erythromycin A (II, wherein, $R_1$=hydroxy, $R_2$=hydroxy and $R_3$=hydrogen) is converted to a corresponding 4",11-diketo-derivative (18) by treatment with an oxidizing agent such as chromic acid. In this process, the 2'-hydroxy group is protected from oxidation by acetylation as discussed in Scheme I. The 4"-ketone is selectively modified to give VIII by hydrogenation in the presence of a catalyst such as Raney nickel, in a polar solvent such as EtOAc/IPA, or by treatment with hydroxylamine in a polar solvent such as MeOH. In the preferred embodiments of VIII, $R_1$=hydroxy or oxo; $R_2$=hydroxy or oxime; and $R_3$=hydrogen.

SCHEME IX

The compounds of Formula IX are synthesized by the method discussed herein. The 4"-amino derivative of 11-oxo-erythromycin A (a mixture of compounds 15 and 17) is converted to the isomeric 11-oxime derivative (19) by treatment with hydroxylamine hydrochloride and a proton acceptor such as TEA in a polar solvent such as MeOH or EtOH. The 11-oxime derivative (19) is treated with titanium (III) chloride in a polar solvent such as methanolic ammonium hydroxide to yield the 11-imine derivative. This compound is then converted to IX by reduction with a reducing agent such as sodium borohydride (NaBH$_4$), in the presence of cerium (III) chloride, in a polar solvent such as MeOH. In the preferred embodiments of IX, $R_1$=—CHNH$_2$; $R_2$=—NH$_2$; and $R_3$=hydrogen.

SCHEME X

The compounds of Formula X are synthesized by the method discussed herein. A mixture of isomeric compounds 15 and 17 is converted to the isomeric 4"-N,N-dimethylamino derivatives (20) by reductive amination with formaldehyde in the presence of a reducing agent such as NaBH$_3$CN in a polar solvent such as acetic acid/CH3CN, followed by acetylation of the 2'-hydroxyl as described in Scheme I. The 2'-hydroxy group is acetylated to protect the 3'-N,N-dimethylamino group from oxidative N demethylation. The 4"-N,N-dimethylamino derivative is oxidized to X by treatment with iodine and sodium acetate in a polar solvent such as MeOH. The 2'-O-acetyl group is removed along with the 4"-N-methyl group during the oxidation step. In the preferred embodiments of X, $R_1$=oxo; $R_2$=NHCH3; and $R_3$=hydrogen.

SCHEME XI

The compounds of Formula XI are synthesized by the method described herein. The 11-Oxo-erythromycin A derivative (II, wherein $R_1$=oxo, $R_2$=hydroxy and $R_3$=hydrogen) is converted to the 11 oxime derivative (21) by treatment with hydroxylamine in a polar solvent such as EtOH or MeOH. The erythromycin 11-oxime derivative (21) is converted to XI by hydrogenation in the presence of a catalyst such as Raney nickel, in a polar solvent such as MeOH or EtOH containing 10% ammonium hydroxide. Alternately, the 11-oxime derivatives may be converted to the corresponding 11 amino derivatives using the method described in Scheme IX. In the preferred embodiments of XI, $R_1$=oxime or —CHNH2; $R_2$=hydroxy; and $R_3$=hydrogen.

SCHEME XII

The compounds of Formula XII (wherein $R_3$=hydrogen or methyl) are synthesized by the methods discussed herein. A 11-amino derivative of the preceding Scheme (XI, wherein $R_1$=—NH2) or its 6-O-methyl analog (III, wherein $R_1$=—NH2) is converted to an 11-benzyloxycarbonylamino derivative or other amino-protected derivative by treatment with a suitable reagent such as benzyloxy N-hydroxysuccinimide, after which the 2-hydroxy group is acetylated as with, for example, acetic anhydride in the presence of potassium carbonate or triethylamine. The resulting 11,2'-diprotected compound is then converted to a thiocarbamate (22) by treatment with a thiocarbonyl reagent such as 1,1'-thiocarbonyl-bis-1H-imidazole, preferably in the presence of one to five molar equivalents of a suitable base such as N,N-dimethyl-4-aminopyridine. This product (22) is then converted to a compound of Formula 23 by treatment with tri-n-butyl tin hydride in the presence of a free radical initiator such as 2,2'-azobisisobutyronitrile.

The intermediate (23) is finally deprotected to form the desired product XII, either by separately removing the amino- and hydroxy-protecting groups using the methods of Scheme I or by simultaneous removal of the two protecting groups using, for example, Raney nickel in methanol in the presence of a base such as ammonium hydroxide.

For all of the schemes outlined above (Schemes I-XII) the particular reaction products formed, the ratios of the different products and the reaction yields will vary with the reaction conditions used including, for example, solvent, catalyst, ratio of reactants, temperature and reaction time.

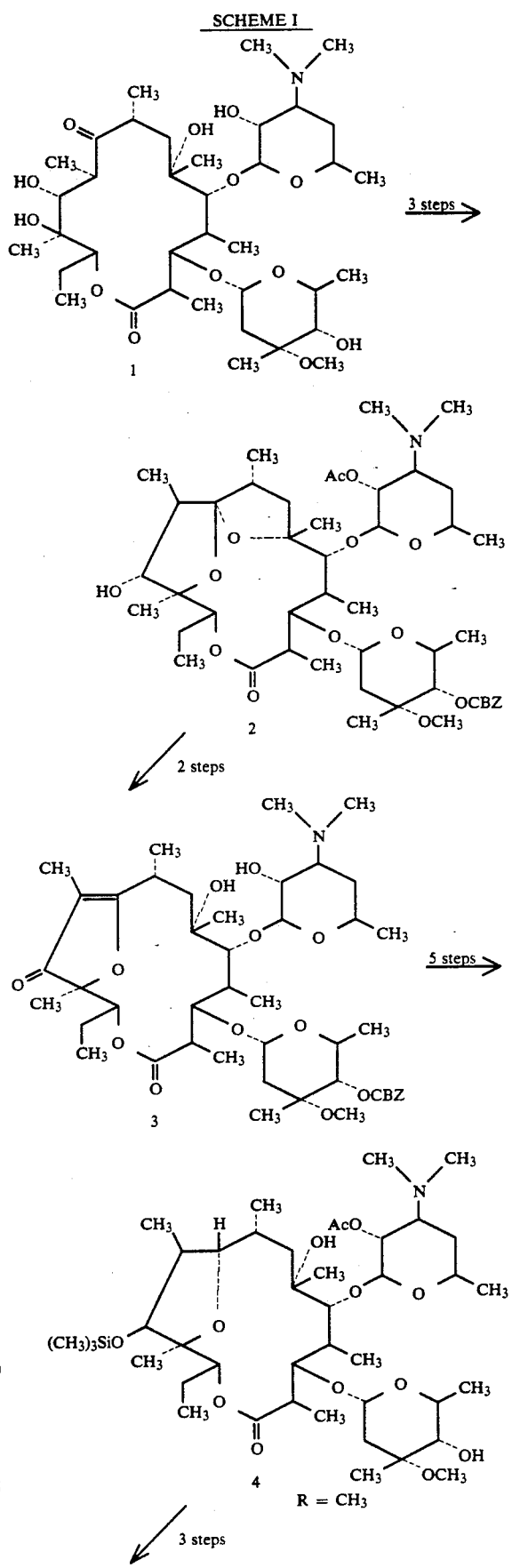

SCHEME I

-continued
SCHEME I
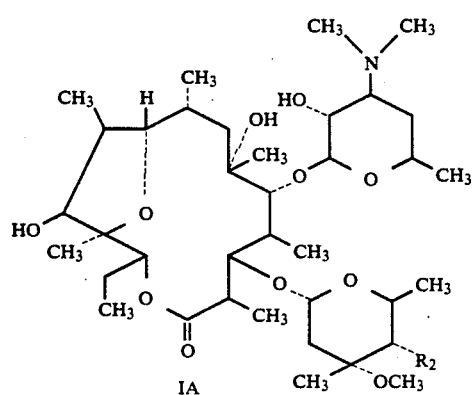
IA
SCHEME II
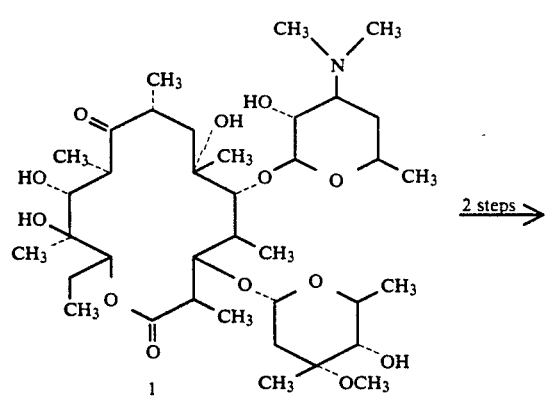
1
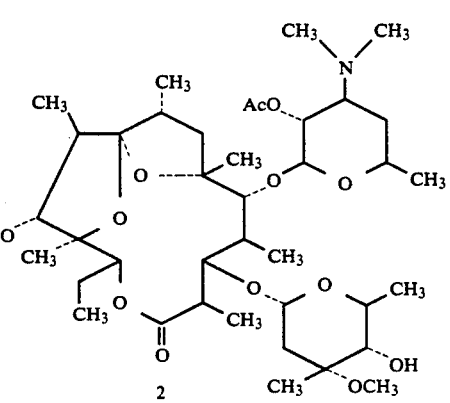
2
↓ 2 steps
-continued
SCHEME II
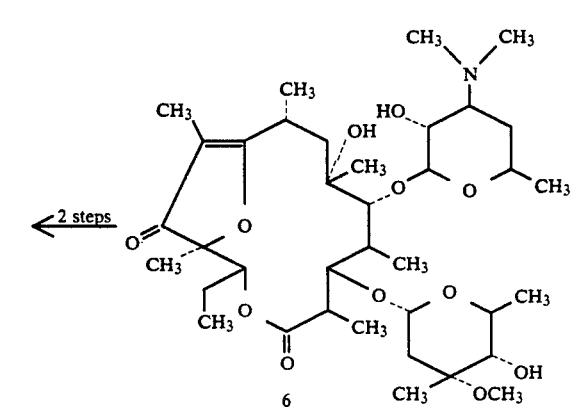
6
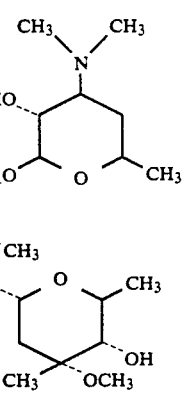
II
↓
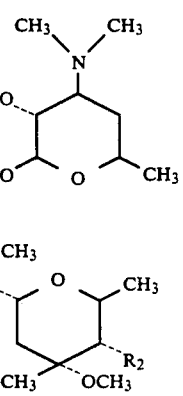
II A

SCHEME III
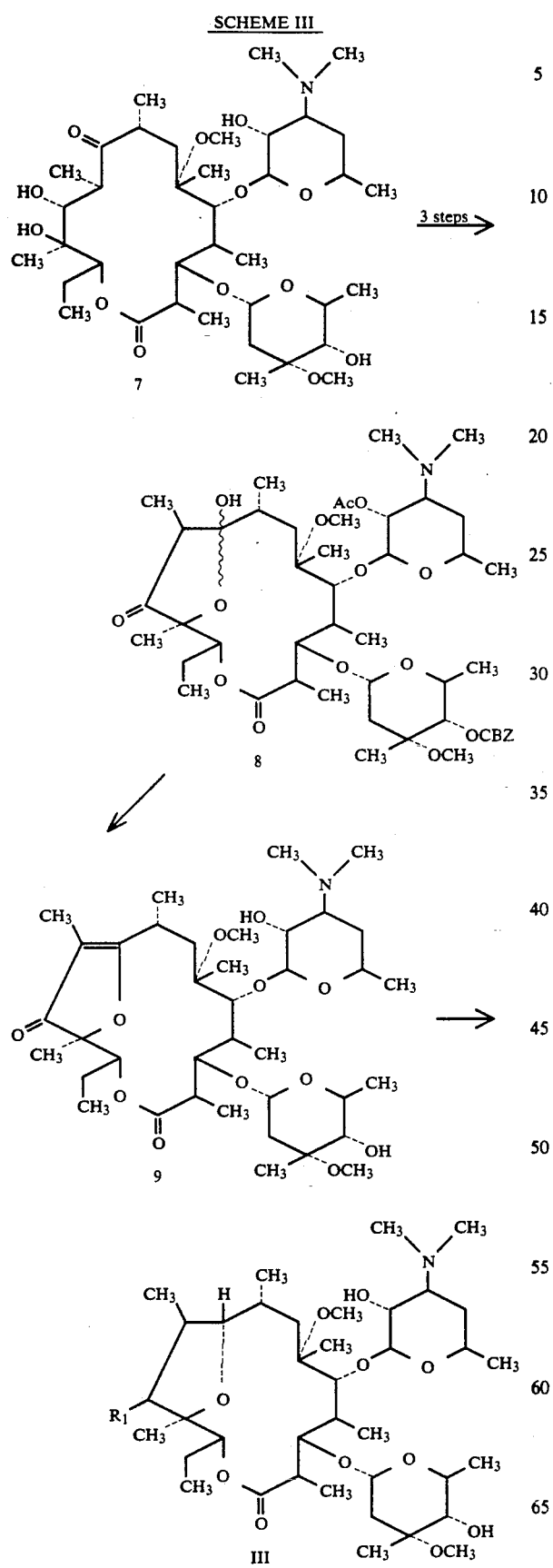
SCHEME IV
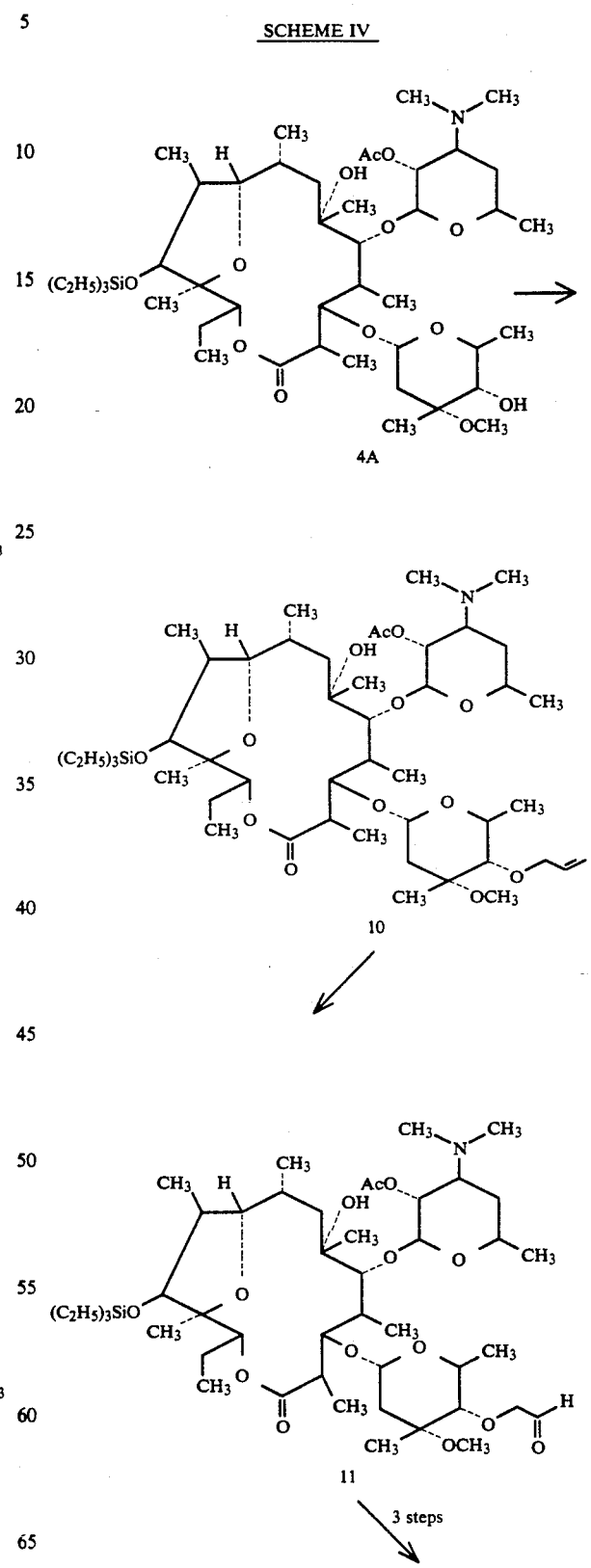

-continued
SCHEME IV
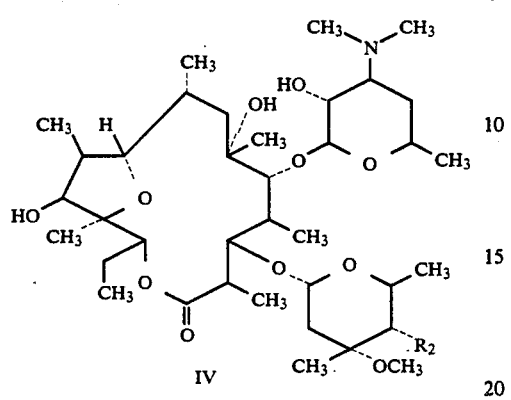
IV
SCHEME V
5 →(2 steps)
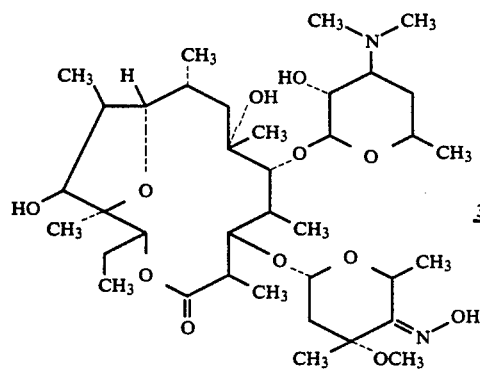
12
13
-continued
SCHEME V
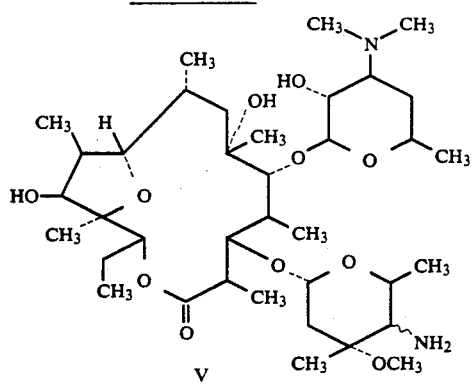
V
SCHEME VI
12 →(3 steps)
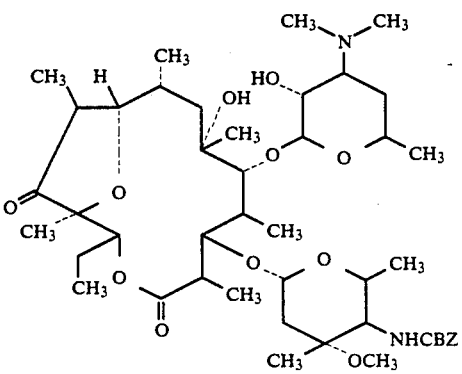
14
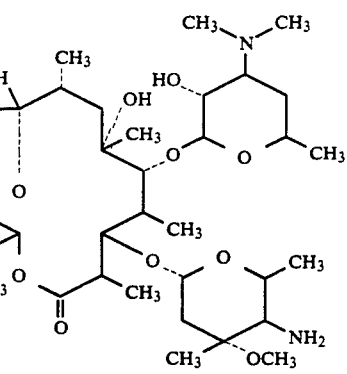
15
SCHEME VII
12 →(3 steps)

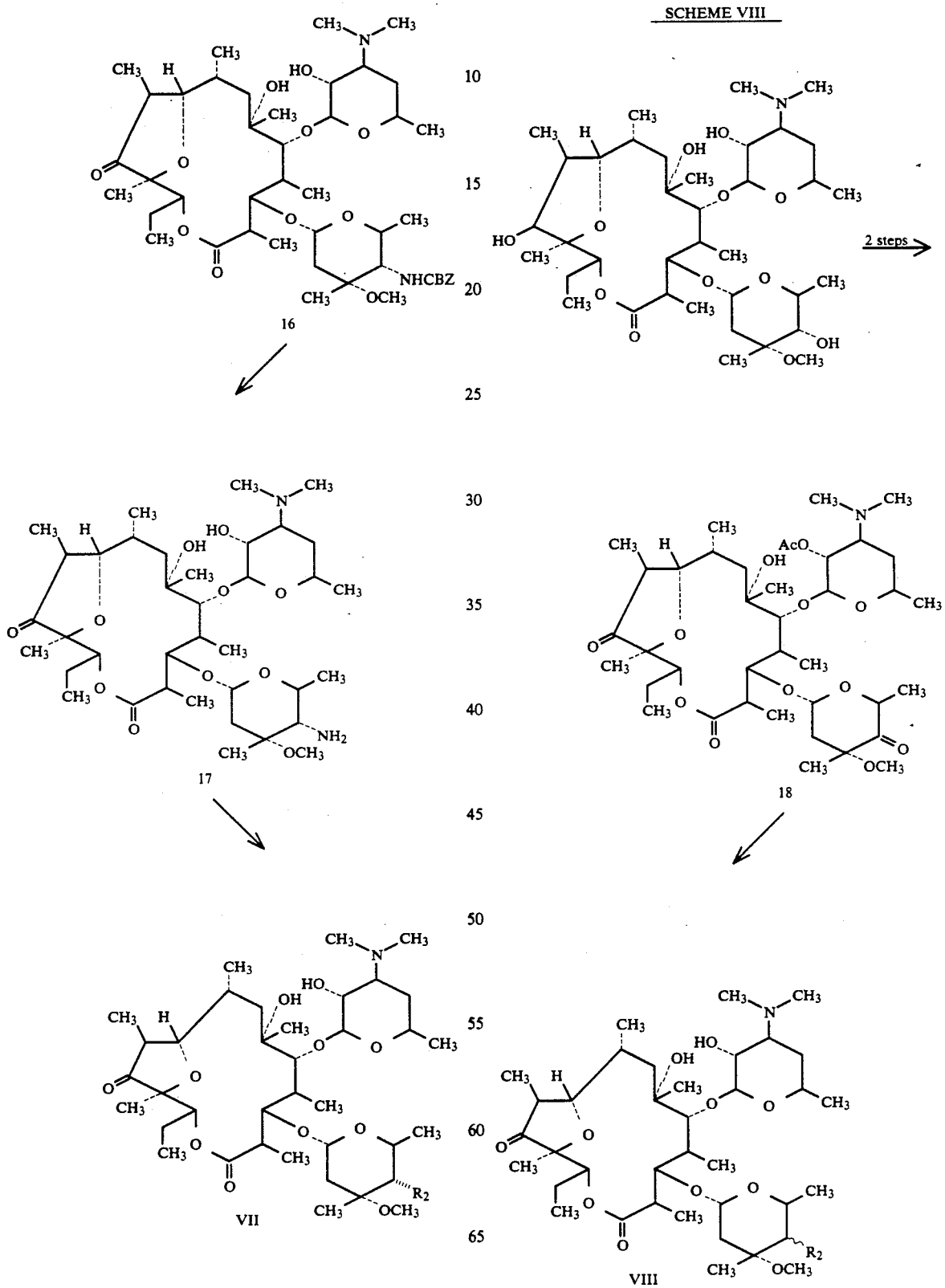

SCHEME IX
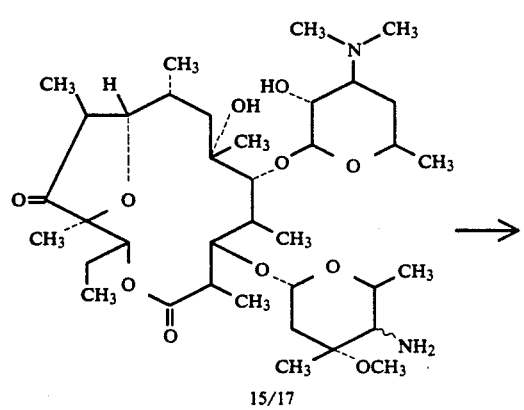
15/17
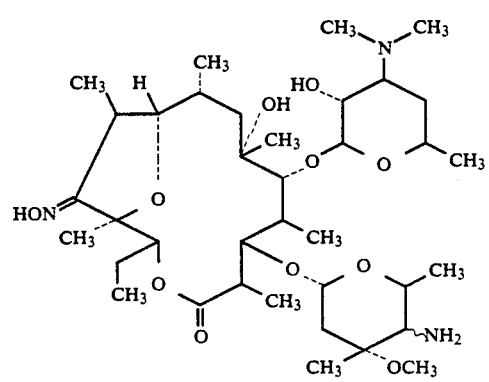
19
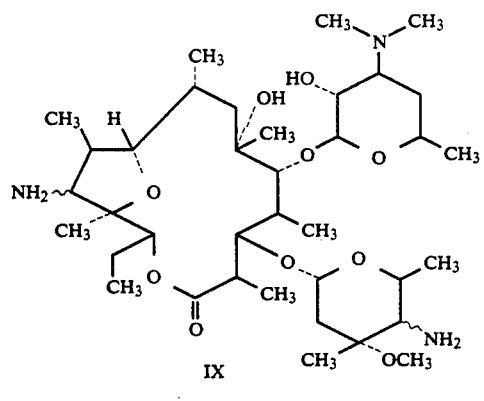
IX
SCHEME X
15/17 <u>2 steps</u> →
SCHEME X
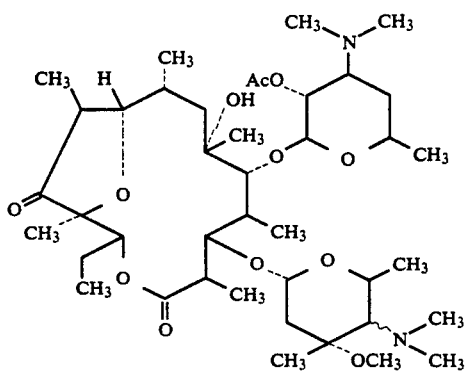
20
X
SCHEME XI
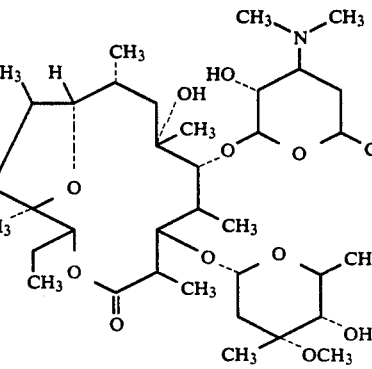
II -continued
SCHEME XI

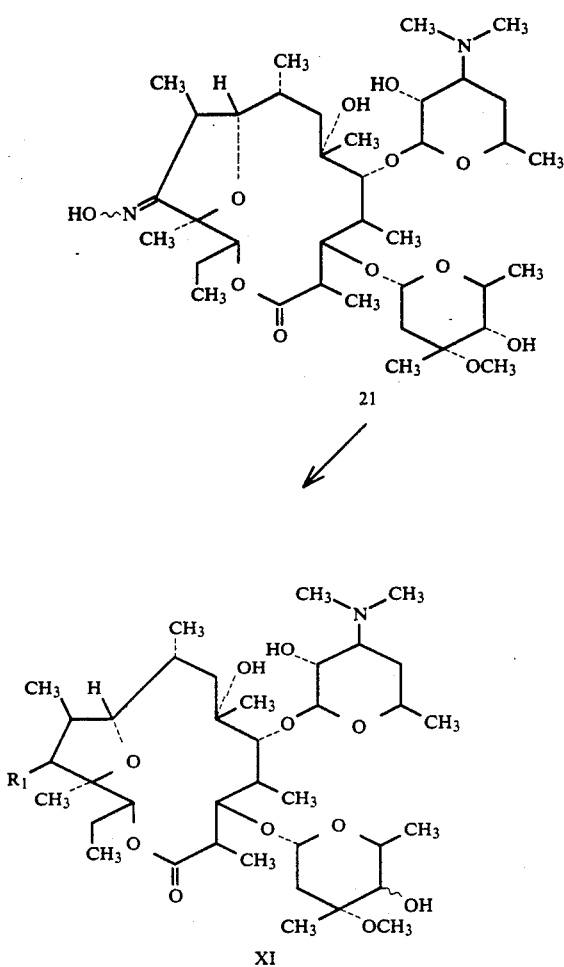

SCHEME XII

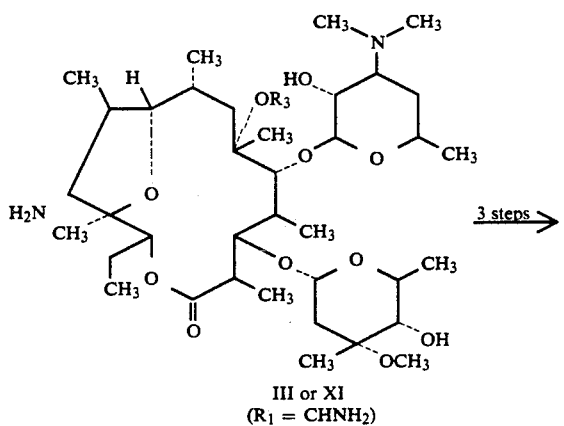

-continued
SCHEME XII

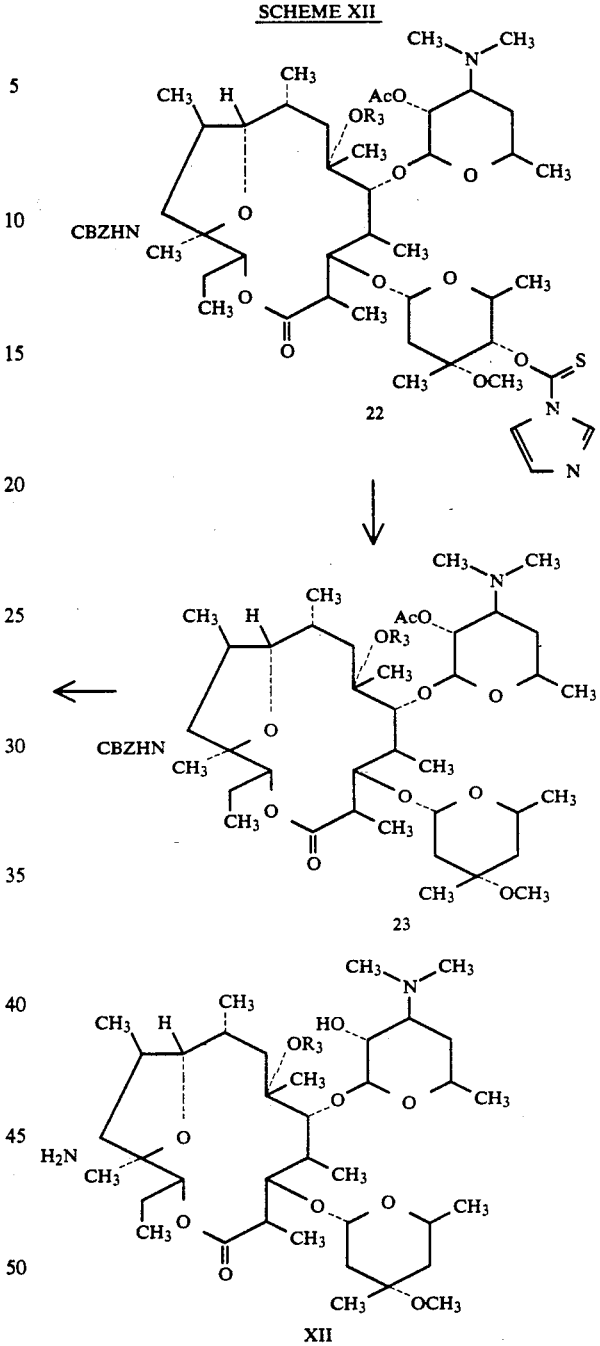

The foregoing may be better understood by reference to the following examples which are provided for illustration and are not intended as a limitation of the practice of the present invention.

EXAMPLE 1

9,10-Didehydro-9-deoxo-11,12-dideoxy-9,12-epoxy-11-oxo-4''-O-[(phenylmethoxy)carbonyl]erythromycin A Step A 2'-O-Acetylerythromycin A Erythromycin A (50.0 g, 68.1 mmol) (commercially available from Abbott Laboratories) was dissolved in 600 mL of methylene chloride ($CH_2Cl_2$) at ambient temperature. Triethylamine (20 mL) and 10 mL (10.82 g, 106 mmol) of acetic anhydride were added to this solution. The reaction mixture was heated to reflux and 100 mL of $CH_2Cl_2$ was distilled from the reaction mixture to remove any traces of water. The reaction mixture was heated at reflux temperature for an additional five hours. After six hours, when the reaction was complete according to TLC analysis, the reaction mixture was cooled to ambient temperature and transferred to a separatory funnel. The $CH_2Cl_2$ solution was washed with 300 mL of ammonium hydroxide/sodium bicarbonate solution containing 2.9% ammonia and 1.8% sodium bicarbonate, dried over anhydrous sodium sulfate, and filtered. The $CH_2Cl_2$ was removed using a rotary evaporator with a water bath temperature of 30°–40° C. The residue was crystallized from 200 mL of acetonitrile ($CH_3CN$) by first dissolving it in hot $CH_3CN$ and allowing the solution to stand overnight at ambient temperature, then cooling it to −25° C. and maintaining this temperature for 24 hours. The product was isolated as white crystals which were washed with cold (−25° C.) $CH_3CN$ and dried in a vacuum oven at 50° C. for approximately 64 hours. The 2'-O-acetylerythromycin A was obtained in 83% yield (43.91 g). mp. 138°–145° C.

$^1H$ NMR ($CDCl_3$) delta 2.06 (s, $OCOCH_3$), 4.76 (dd, 2').

Step B

2'-O-Acetyl-4''-O-[(phenylmethoxy)carbonyl]erythromycin A

2'-O-Acetylerythromycin A (46.57 g, 60.3 mmol). from STEP A, and 29.34 grams (240 mmol) of dimethylaminopyridine were dissolved in 500 mL of $CH_2Cl_2$ and the resultant solution was cooled to −25° C. To this solution, 25.7 mL (30.84 g, 180.8 mmol) of benzylchloroformate was added over a period of 30 minutes. The reaction mixture was kept at −25° C. for four days then washed with 2×300 mL portions of aqueous 4% potassium dihydrogen phosphate solution and 200 mL of 2% sodium bicarbonate solution. The $CH_2Cl_2$ layer was dried over anhydrous sodium sulfate, filtered and the solvent was removed with a rotary evaporator. The residue was dried in a vacuum oven for 24 h at 50° C. then crystallized twice from acetonitrile at −25° C. The crystals were dried in a vacuum oven at 50° C. to give 32.25 grams (65% yield) of 2'-O-acetyl 4''-O-[(phenylmethoxy)carbonyl]erythromycin A, m.p. 123°–128° C.

Anal. Calculated for $C_{47}H_{75}NO_{16}$ (910.119): C, 62.03; H, 8.31; N, 1.54. Found: C, 61.77; H, 8.11; N, 1.87.

$^1HNMR$ ($CDCl_3$) delta 2.05 (s, $OCOCH_3$), 4.46 (d, 4''), 4.74 (dd, 2'), 5.13 (d, benzylic H), 5.25 (d, benzylic H), 7.36 (s, $C_6H_5$)

Step C

2'-O-Acetyl-4''-O-[(phenylmethoxy)carbony]anhydroerythromycin A

2'-O-Acetyl-4''-O-[(phenylmethoxy)carbonyl]erythromycin A (53.16, 58.4 mmol), from STEP B, was dried in a vacuum oven at 50° C. After being crushed to a fine powder, it was suspended with vigorous stirring in 975 mL of distilled water in a 2 L round bottom flask. Concentrated hydrochloric acid (5.6 mL of 37% HCl) was then added in one portion at ambient temperature. The reaction mixture was stirred at ambient temperature for 40–90 minutes and monitored by TLC. The silica gel TLC plates were eluted with a mixture of chloroform, methanol and ammonia (9.5:0.3:0.2, v/v/v). When the starting material had been consumed, according to TLC analysis, the reaction mixture was filtered, made basic with concentrate ammonium hydroxide and extracted three times with 300 mL of chloroform. The combined chloroform extracts were washed once with 300 mL of 5% sodium bicarbonate ($NaHCO_3$) solution, once with 300 mL of saturated sodium chloride solution (brine), dried over anhydrous sodium sulfate, and filtered. The chloroform was removed on a rotary evaporator to yield crude product. Recrystallization from ethyl acetate (EtOAc): heptane yielded 33.85 grams (65% yield) of pure 2'-O-acetyl 4''-O-[(phenylmethoxy)]carbonylanhydroerythromycin A as white crystals: mp 134°–137° C.

Anal. Calculated for $C_{47}H_{73}NO_{15}$ (892.104): C, 63.28; H, 8.25; N, 1.57. *Found: C, 63.61; H, 8.28; N, 1.44.

IR (5% in $CDCl_3$): max 2975, 2940, 2880, 2835, 2785, 1738, 1458, 1375, 1340, 1292, 1260, 1189, 1169, 1109, 1052, 1008 $cm^{-1}$.

FAB $(M+H)^+$ at M/Z: 892.

$^1HNMR$ ($CDCl_3$) delta 2.09 (s, $OCOCH_3$), 4.47 (d, 4''), 4.81 (dd, 2'), 5.19 (s, benzylic $CH_2$), 7.36 (m, $C_6H_5$)

Step D

2'-O-Acetyl-11-deoxy-11-oxo-4''-O-[(phenylmethoxy)carbonyl]anhydroerythromycin A A solution of N chlorosuccinimide (30.4 g, 228 mmol) in 558 mL of a mixture of toluene and benzene (2.88:1.00, v/v) was prepared at ambient temperature and cooled to −10° C. Methyl sulfide (22 mL, 18.6 g, 299 mmol) was added and the mixture was stirred for 20 minutes at −10° C. A second solution containing 33.85 g (37.9 mmol) of 2'-O-acetyl-4''-O-[(phenylmethoxy)carbonyl]anhydroerythromycin A 6,9,12-cyclic acetal, from STEP C, in 300 mL of a mixture of toluene and $CH_2Cl_2$ (2 33:1.00, v/v) was prepared at ambient temperature and added to the reaction mixture solution. The resultant solution was stirred for 10 minutes at −10° C. and was kept at 25° C. for 2.5 hours. After an additional 2.5 h, 36 mL of dry triethylamine (TEA) was added to the reaction mixture with swirling and this solution stood for 5 minutes at ambient temperature. The reaction mixture was washed with 250 mL of 5% sodium bicarbonate solution followed by 250 mL of brine, dried over anhydrous sodium sulfate, and filtered. The solvents were removed on a rotary evaporator. The residue was recrystallized from isopropyl alcohol yielding 28.6 g. (85% yield) of 2'-O-acetyl-11-deoxy-11-oxo-4''-O-[(phenylmethoxy)carbonyl]anhydroerythromycin A as white crystals: mp 128°–132° C.

Anal. calculated for $C_{47}H_{71}NO_{15}$ (890.088): C, 63.42; H, 8.04; N, 1.57. Found: C, 63.29; H, 8.08; N, 1.44.

IR (5% in $CDCl_3$): max 2980, 2940, 2880, 1740, 1458, 1374, 1260, 1170, 1058, 1009 $cm^{-1}$.

FAB $(M+H)^+$ at M/Z: 890.

$^1HNMR$ ($CDCl_3$) delta 2.05 (s, $OCOCH_3$), 4.47 (d, 4''), 4.73 (dd, 2'), 5.19 (s, benzylic $CH_2$), 7.36 (m, $C_5H_6$) $^{13}C$ NMR ($CDCl_3$) delta 115.0 (C 9), 215.6 (C 11).

Step E 9,10-Didehydro-9-deoxo-11,12-dideoxy-9,12-epoxy-11--oxo-4''-O--[(phenylmethoxy)carbonyl]erythromycin A 2'-O-acetyl-11-deoxy-11-oxo-4''-O-[(phenylmethoxy) carbonyl]anhydroerythromycin A, from STEP D, was dried for 24 h in a vacuum oven at 50° C. A slurry was made from 25.74 g (28.9 mmol) of the dried material in 805 mL of methanol. Triethylamine (22 mL) was added to the slurry followed by 11.2 grams (161 mmol) of hydroxylamine hydrochloride. The reaction mixture was brought to reflux temperature and was maintained at reflux temperature for 3.5 hours. The clear solution which formed was cooled to ambient temperature, concentrated to about 100 ml and was diluted with 400 mL of methylene chloride, washed with 400 mL of 5% sodium bicarbonate, 400 mL of brine, dried over anhydrous sodium sulfate, and filtered. The solvents were removed on a rotary evaporator to yield 21 g (24 mmol, 83% yield) pure 9,10-didehydro-9-deoxo-11,12-dideoxy-9,12-epoxy-11-oxo-4''-O-(phenylmethoxy)carbonyl]erythromycin A.

Anal. calculated for $C_{45}H_{69}NO_{14}$ (848.050): C, 63.73; H, 8.20; N, 1.65. Found: C, 63.29, H, 8.26, N, 1.71.

IR (5% in $CDCl_3$): 3400, 2980, 2940, 2880, 1734, 1690, 1613, 1458, 1383, 1262, 1180, 1018 $cm^{-1}$.

FAB $(M+H)^+$ at M/Z: 848.

$^1$HNMR ($CDCl_3$) delta 1.74 (s, 10 $CH_3$), 3.31 (dd, 2'), 4.48 (d, 4''), 5.14 (d, benzylic H), 5.22 (d, benzylic H), 7.36 (m, $C_6H_5$)

$^{13}$C NMR ($CDCl_3$) delta 108.8 (C 10), 193.1 (C 9), 204.9 (C 11).

EXAMPLE 2

2'-O-Acetyl-11-deoxy-11-oxoanhydroerythromycin A

Method A

2'-O-Acetyl-11-deoxy-11-oxo-4''-O-[(phenylmethoxy) carbonyl]anhydroerythromycin A, the product of Example 1 STEP D, (2.0 g, 2.25 mmol) was dissolved in 100 ml of ethyl acetate (EtOAc). To this solution was added 2.00 g 10% palladium on carbon (Pd/C). The resultant suspension was shaken at ambient temperature, under 4 atmospheres of hydrogen gas, for 1.5 h. The reaction mixture was then filtered to remove the catalyst and the filter cake washed with 4×100 mL of EtOAc. The gray colored filtrate was concentrated in vacuo to 200 mL and washed with 2×mL or 5% aqueous sodium bicarbonate solution. The EtOAc solution was clear and colorless after washing. The clear solution was dried over anhydrous sodium sulfate, filtered and concentrated in vacuo. The residue was pumped to dryness with a vacuum pump to yield 1.48 g (87.3% yield) of the title compound as a white glass, which was further dried in a vacuum oven at 100° C. for 2 h.

Anal. calculated for $C_{39}H_{65}NO_{13}$ (755.952): C, 61.97; H, 8.67; N, 1.85. Found: C, 61.71; H, 8.58; N, 1.83.

FAB $(M+H)^+$ at M/Z: 756.

IR (0.15% in $CCl_4$): 3560, 1750, 1740 $cm^{-1}$.

$^1$H NMR ($CDCl_3$ delta 2.07 (s, $COCH_3$), 2.27 (s, $N(CH_3)_2$), 3.01 (dd, 4''), 3.28 (s, $OCH_3$), 4.37 (d, 1'), 4.77 (dd, 2'), 5.13 (2H, m, 1'',13).

Method B

Steps A, B and C

2'-O-Acetylanhydroerythromycin A

Step A

Erythromycin A (50.0 g, 68.1 mmol) was ground with a mortar and pestle to a fine powder and suspended in 1.5 L of water in a 4 L Erlenmeyer flask. The suspension was mechanically stirred. Three 25 mL aliquots of 1N hydrochloric acid solution were added lowering the pH of the reaction mixture to 2. After stirring for one hour at ambient temperature, no starting material was detected by HPLC analysis on a $C_8$ reverse phase column 4.6×250 mm (YMC, INC, Morris Plains, N.J.); water:acetonitrile:methanol (12:7:1, v/v/v) containing 10 g/L sodium acetate trihydrate and 0.5 mL/L glacial acetic acid; isocratic elution; flow rate=1 mL/min; retention time of starting material: 7.4 min) and the intermediate, anhydroerythromycin A, was eluted with a retention time of 11.4 minutes (purity 95.5%, RI detection). This intermediate was not characterized for this synthesis, but was previously purified and characterized by NMR and MS data: $^1$HNMR ($CDCl_3/D_2O$) delta 2.99 (d, 4''), 3.21 (dd, 2'), 3.50 (d,11), $^{13}$C NMR delta 115.9 (C 9), FAB $(M+H)^+$ at M/Z: 716. Approximately 0.5 mL of concentrated ammonium hydroxide was added to bring the pH of the reaction mixture to 4.5 in order to quench any further reaction. The reaction mixture was transferred to a separatory funnel and 100 mL of concentrated ammonium hydroxide was added to make the clear solution basic. The precipitated product was extracted with 3×400 mL of chloroform. The combined chloroform layers were washed with 400 mL of 5% sodium bicarbonate and dried over anhydrous sodium sulfate.

Step B

The dried chloroform solution was filtered into a 2L round-bottom flask and 50 mL of triethylamine was added, followed by 20 mL (21.64 g, 212 mmol) of acetic anhydride. The reaction mixture was stirred overnight at ambient temperature. According to HPLC and TLC analyses, conversion to the product, 2'-O-acetylanhydroerythromycin A (retention time on HPLC: 42.6 minutes) was complete. The chloroform solution was washed once with 450 mL of a basic solution containing 400 mL of 5% sodium bicarbonate and 50 mL concentrated ammonium hydroxide, once with 5% sodium bicarbonate, dried over anhydrous sodium sulfate and filtered. The chloroform was removed on a rotary evaporator. The residue was redissolved in acetonitrile and the acetonitrile was subsequently removed on the rotary evaporator to yield the product, 2'-O-acetylanhydroerythromycin A. The title compound was dried at ambient temperature to give 49.4 g (95.7% yield).

$_1$H NMR ($CDCl_3$) delta 2.10 (s, $COCH_3$), 3.01 (m, 4''), 3.51 (m, 11), 4 83 (dd, 2').

FAB $(M+H)^+$ at M/Z: 776 (775.983 calculated for $C_{39}H_{69}NO_{14}$).

Step C1

A solution was prepared containing 84.59 g (111.5 mmol) of 2'-O-acetylanhydroerythromycin A (from STEP B) and 14.69 g (125.4 mmol) of N-methylmorpholine N oxide (NMO) in 1.5 L of methylene chloride ($CH_2Cl_2$) To this solution was added 50 g of 4 A molecular sieves and the resultant suspension was stirred mechanically for approximately five minutes. Tetrapropylammonium perruthenate (TPAP; 3.19 g, 9.1 mmol) was added, with stirring, and the reaction mixture was stirred at ambient temperature for 2 hs. The reaction mixture was then filtered by gravity, through 2 micron filter paper, into a separatory funnel. The $CH_2Cl_2$ solution was washed with 2×1 L of 5% aqueous sodium sulfite solution, followed by 1 L of 5% aqueous sodium dihydrogen phosphate solution (pH=5). The washed organic layer was then dried over anhydrous sodium sulfate, filtered and concentrated in vacuo. The concentrate (a black slurry) was dissolved in 900 mL of isopropyl alcohol (IPA) and treated with activated charcoal (seven spatulafuls of Darco G-60). The charcoal suspension was swirled and left to stand at ambient temperature for approximately five minutes. The spent charcoal was then removed by filtration and the IPA removed in vacuo to yield 73 g of crude 2'-O-acetyl-11-deoxy-11-oxoanhydroerythromycin A which was 63.1% pure according to HPLC analysis using a YMC R-ODS-7 ($C_8$) reverse phase column with the following conditions: eluent: $CH_3CN:H_2O:MeOH$ (13:7:1, v/v/v) containing 10 g/L sodium acetate and 0.5 mL/L glacial acetic acid; isocratic elution; flow rate 1.0 mL.min.

Step C2

A chromic acid solution containing 20 grams (68.0 mmol) of potassium dichromate, 15 mL (281.3 mmol) of sulfuric acid and 110 mL of glacial acetic acid in 900 mL of water was prepared. To this solution, with mechanical stirring, was added 49.0 grams (64.6 mmol) of the 2'-O-acetylanhydroerythromycin A, from STEP B, which was dissolved in 1 L of methylene chloride. The biphasic reaction mixture was stirred at ambient temperature for 2.5 hours. The reaction progress was followed by HPLC (YMC) on a $C_8$ reverse phase column 4.6×250 mm; eluent: $CH_3CN:H_2O:CH_3OH$ (13:7:1, v/v/v) containing 10 g/L sodium acetate and 0.5 mL/L glacial acetic acid; isocratic elution; flow rate 1.0 mL/min). After 2.5 hours, the desired product peak area was 73.7% (RI detection: retention time 20.4 minutes) and the reaction was quenched with 30 mL of isopropyl alcohol. The reaction mixture was then stirred at ambient temperature for an additional hour, at which time it was cooled in an ice/water bath. The reaction mixture was made basic by the addition of 100 mL of concentrated ammonium hydroxide. The layers were separated and the aqueous layer was extracted with 300 mL of methylene chloride. The methylene chloride layers were combined and washed with 4×400 mL of 5% sodium bicarbonate followed by 5–400 ml washings of brine (until the washings were near colorless). The methylene chloride solution was then dried over anhydrous sodium sulfate and filtered. The solvent was removed on the rotary evaporator to give a residue which was redissolved in acetonitrile. The acetonitrile was evaporated to yield 45.3 grams of crude product which was 73.2% 2'-O-acetyl-11-deoxy-11-oxoanhydroerythromycin A according to HPLC analysis.

EXAMPLE 3

9,10-Didehydro-9-deoxo-11,12-dideoxy-9,12-epoxy 11oxoerythromycin A

Method A

The product of EXAMPLE 1 (2.06 g, 2.4 mmol) was dissolved in 70 mL of methanol and allowed to stand at ambient temperature for 2 days. To this solution was added 1 g of 20% palladium on carbon. The suspension was shaken at ambient temperature, under 4 atmospheres of hydrogen gas for 10 hours. The reaction mixture was then filtered sequentially by gravity and through a millipore filter to remove the catalyst. The methanol was removed on a rotary evaporator and the residue was taken up in 100 mL of methylene chloride. The methylene chloride solution was washed with 200 mL of 5% sodium bicarbonate solution, 150 mL of brine, dried over anhydrous sodium sulfate, filtered, and concentrated on a rotary evaporator. The residue was 1.24 g of pure 9,10-Didehydro-9-deoxo-11,12-dideoxy-9,12-epoxy-11-oxoerythromycin A, which was crystallized from hot acetonitrile: mp 149°–153° C.

Anal. calculated for $C_{37}H_{63}NO_{12}$ (713.914): C, 62.25; H, 8 89; N, 1.96. Found: C, 61.92; H, 9.06; N, 1.94.

$FAB(M+H)^+$ at M/Z: 714.

IR (5% in $CDCl_3$): 3400 (O-H), 1730 (lactone C=O), 1687 (enone C=O), 1612 (enone C=C) $cm^{-1}$.

$^1HNMR$ ($CDCl_3/D_2O$) delta 1.74 (s, 10 $CH_3$), 2.32 (s, $N(CH_3)_2$), 3.02 (d, 4"), 3.29 (s, $OCH_3$), 3.37 (dd, 2'), 5.02 (dd, 13).

$^{13}C$ NMR ($CDCl_3$) delta 96.5 (C 1"), 104.7 (C 1'), 108.6 (C 10), 193.0 (C 9), 204.9 (C 11).

Method B

The product of EXAMPLE 2/Method B was dissolved in 1.25 L of methanol and 250 mL of methanol was distilled to remove any residual methylene chloride. Triethylamine (80 mL) and hydroxylamine hydrochloride (40 g, 0.58 mol) were added and the reaction was run as described in EXAMPLE 1, STEP E. The crude product was recrystallized twice from acetonitrile to yield 22.47 grams of pure 9,10-didehydro-9-deoxo-11,12-dideoxy-9,12-epoxy-11-oxoerythromycin A: mp 149°–153° C.

FAB $(M+H)^+$ at M/Z: 714.

IR (5% in $CDCl_3$): 3400 (O—H), 1730 (lactone C=O), 1687 (enone C=O), 1612 (enone C=C) $cm^{-1}$.

The 300 MHz $^1H$ and $^{13}C$ NMR spectra were identical with the product of Method A.

EXAMPLE 4

(9S,11S)-9-Deoxo-12-deoxy-9,12-epoxyerythromycin A

Method A

Step A (9S,11S)-9-Deoxo-12-deoxy-9,12-epoxy-4"-O-[(phenylmethoxy)carbonyl]erythromycin A The product of EXAMPLE 1 was dried in a vacuum oven at 50° C. for 24 hours and 20.28 g (23.91 mmol) of this product was dissolved in a mixture of 260 mL of tetrahydrofuran (THF) and 33 mL of isopropyl alcohol. Lithium borohydride (8.0 g, 367.3 mmol) was added, with stirring, to the solution at ambient temperature. Heat and gas were evolved during the addition. The resultant gray suspension was kept at 5° C. for 2 days, then treated with 25 mL of 50% sodium carbonate and diluted with 300 mL of benzene. The organic layer was washed with 5×100 mL portions of sodium bicarbonate (until bubbling stopped) and 100 mL of brine, dried over anhydrous sodium sulfate, and concentrated to 18 g of crude (9S,11S)-9-deoxo-12-deoxy-9,12-epoxy-4"-O-[(phenylmethoxy)carbonyl]erythromycin A as a white glass. The crude product was dissolved in methanol and this solution was left at ambient temperature for two days to decompose borate ester complexes. The methanol was removed on a rotary evaporator. The residue (in divided portions) was purified on a silica gel column (3.5 X 50 cm) which was eluted with 1 L of a mixture of chloroform, methanol and ammonia (9.5:0.15:0.15 v/v/v), collecting fractions at 1.8 minute intervals. The fractions containing the product were combined and the solvents were removed on a rotary evaporator to yield 7.0 g (35% yield) pure (9S,11S)-9-deoxo-12-deoxy 9,12-epoxy 4"-O-[(phenylmethoxy) carbonyl]erythromycin A.

FAB $(M+H)^+$ at M/Z: 852 (852.082 calculated for $C_{45}H_{73}NO_{14}$).

IR (5% in CDCl$_3$): 3440 (O-H), 1740 (C=O) cm$^{-1}$.

$^1$HNMR (CDCl$_3$) delta 3.17 (dd, 2'), 2.28 (s, N(CH$_3$)$_2$), 3.31 (s, OCH$_3$), 3.67 (dd, 9), 4.28 (dd, 11), 4.49 (d, 4''), 5.13 (d, benzylic H), 5.24 (d, benzylic H), 7.35 (m, C$_6$H$_5$).

Step B (9S,11S)-9-Deoxo-12-deoxy-9,12-epoxyerythromycin A (9S,11S)-9-Deoxo-12-deoxy-9,12-epoxy-4''-O-[(phenylmethoxy)carbonyl]erythromycin A, from STEP A, was deprotected, specifically, the 4''-O-benzyloxycarbonyl (CBZ) group was removed, as described in EXAMPLE 3, METHOD A, for the removal of the CBZ group from 9,10-didehydro-9-deoxo-11,12-dideoxy-9,12-epoxy-11-oxo-4''-O-[(phenylmethoxy)carbonyl]erythromycin A. The title compound was obtained as white crystals from benzene/heptane in 92% yield, mp 137-°143° C.

Anal. calculated for C$_{37}$H$_{67}$NO$_{12}$ (717.946): C, 61.90; H, 9.41; N, 1.95. Found: C, 61.86; H, 9.36; N, 1.90.

FAB (M+H)$^+$ at M/Z: 718.

$^1$HNMR (CDCl$_3$) delta 3.01 (dd, 4''), 3.22 (dd, 2'), 3.66 (dd, 9), 4.27 (dd, 11).

Method B 9,10 Didehydro-9-deoxo-11,12-dideoxy-9,12-epoxy-11oxoerythromycin A, from EXAMPLE 3, (22.39 g, 31.36 mmol) was dissolved in 800 mL of tetrahydrofuran (THF) in a 3 L 3-neck round-bottom flask fitted with an overhead mechanical stirrer. Lithium borohydride (9.0 g, 413.2 mmol) was added and rinsed into the flask with an additional 200 mL of THF. The reaction mixture was stirred at ambient temperature and sampled periodically for TLC analysis. The silica gel TLC plates were eluted with a solvent mixture of chloroform, methanol, and ammonia (9:1:0.2). After 7.5 h, an additional 1.0 g of lithium borohydride was added and the reaction mixture was stirred overnight, at ambient temperature. The following morning, 100 mL of methanol was added dropwise to the stirring reaction mixture. Neither hydrogen evolution nor an increase in the temperature of the reaction mixture was observed. Glacial acetic acid (25 mL) was then added dropwise into the reaction mixture from an addition funnel. Hydrogen gas was evolved for 30-40 minutes and the mixture was cooled in an ice/water bath. After 2 h of stirring at ambient temperature, 800-900 mL of THF was removed on a rotary evaporator. The concentrated reaction mixture was diluted with 1.0 L of 5% sodium bicarbonate solution. The resultant solution was extracted with 3×300 mL of methylene chloride. The combined extracts were washed with 400 mL of 5% sodium bicarbonate solution, dried over anhydrous sodium sulfate, and filtered. A rotary evaporator was used to remove the solvent yielding crude product, which was redissolved in 100 mL of acetonitrile. The acetonitrile was removed on a rotary evaporator and the residue was pumped to dryness (1 hour) with a vacuum pump to give 21.8 g of crude product. It was necessary to add 500 mL of methanol to completely decompose the borohydride complex of the product. The methanol solution was stirred at ambient temperature for four days, after which the methanol was removed on a rotary evaporator. The residue was redissolved in 500 mL of ethyl acetate and the ethyl acetate solution was washed with 3×200 mL of 5% sodium bicarbonate solution, dried over anhydrous sodium sulfate, and filtered. The ethyl acetate was removed on a rotary evaporator yielding a white glass, which was dried by vacuum pump for 3 days. The glass was dissolved in 40 mL of chloroform containing 3% methanol and 0.2% concentrated ammonium hydroxide (the eluting solvent). This solution was loaded onto a silica gel (70-230 mesh) column (5×41.5 cm) which had been packed in acetonitrile and preconditioned with 4 L of a 3% solution of concentrated ammonium hydroxide in chloroform, followed by 3.0 L of the eluting solvent. The column was run at 3.5 mL/min and fractions were collected at 7 minute intervals. At fraction number 135, the concentration of ammonium hydroxide in the eluent solvent was increased to 0.3%. Fractions numbered 55-210 were combined and the solvent was removed with a rotary evaporator to yield a white glass, which was dried on the vacuum pump to constant weight at ambient temperature. The white glass was crystallized from 200 mL of hot benzene, to which was added 200 mL of n-heptane. The crystals were washed with 50/50 benzene/heptane solution and air dried yielding 11.23 g of (9S,11S)-deoxo-12-deoxy-9,12-epoxyerythromycin A, mp 137°-143° C. An additional 1.9 g of product was recovered from the mother liquor making the yield of (9S,11S)- 9-deoxo-12-deoxy-9,12-epoxyerythromycin A 58.2%.

FAB (M+H)$^+$ at M/Z: 718.

$^1$HNMR was identical with the Product of Method A.

EXAMPLE 5

(9S)-9-Deoxo-11,12-dideoxy-9,12-epoxy-11-oxoerythromycin A

Method A 9,10-Didehydro-9-deoxo-11,12-dideoxy-9,12-epoxy-11-oxoerythromycin A, from EXAMPLE 3, was treated with diisobutylaluminum hydride in tetrahydrofuran as described in EXAMPLE 7, STEP B, for 9,10-didehydro-9-deoxo-11,12-dideoxy-9,12-epoxy-11-oxo-4''-O-[(phenylmethoxy)carbonyl]erythromycin A to give the title compound as needles from methanol/water, mp 159°-161° C.

Anal. calculated for C$_{37}$H$_{65}$NO$_{12}$ (715.930): C, 62.07; H, 9.15; N, 1.96. Found: C, 61.83; H, 9.20, N, 1.90.

FAB (M+H)$^+$ at M/Z: 716.

IR (0.15% in CDCl$_3$): 3480 (O-H), 1755 and 1738 (C=O) cm$^{-1}$.

$^1$HNMR (CDCl$_3$) delta 2.30 (s, N(CH$_3$)$_2$), 3.03 (dd, 4''), 3.28 (s, OCH$_3$), 3.30 (dd, 2'), 3.78 (dd, 9), 5.13 (dd, 13).

$^{13}$C NMR delta 87.5 (C 9), 97.7 (C 1''), 105.1 (C 1'), 177.0 (C 1), 217.6 (C 11).

Method B

Step A (9S,11S)-2'-O-Acetyl-9-deoxo-12-deoxy-9,12-epoxy-4''-O-[(phenyl methoxy)carbonyl]erythromycin A The product of EXAMPLE 4, METHOD A, STEP A, (3.4 g, 4.0 mmol) was dissolved in 23 mL of methylene chloride at ambient temperature. Potassium carbonate (1.7 g, 12.3 mmol) was crushed with a mortar and pestle and added to the solution with stirring, followed by acetic anhydride (1.13 mL, 1.22 g, 12.0 mmol). The reaction mixture was stirred at ambient temperature for 2 h, at which time the reaction was quenched by the addition of 23 mL of 5% sodium bicarbonate solution. The methylene chloride layer was separated and washed with 23 mL of brine, dried over anhydrous sodium sulfate, filtered and concentrated on a rotary evaporator to yield 2.85 g (80% yield) of (9S,11S,-2-O-acetyl-9-deoxo-12-deoxy-9,12-epoxy-4'''-O-[(phenylmethoxy)carbonyl]erythrocmycin A as a white powder.

FAB (M+1)+ at M/Z:894 (894.120 calculated for $C_{47}H_{75}O_{15}$).

$^1$HNMR (CDCl$_3$) delta 2.06 (s, COCH$_3$), 2.27 (s, N(CH$_3$)$_2$), 3.32 (s, OCH$_3$), 3.66 (dd, 9), 4.48 (d, 4''), 4.75 (dd, 2''), 5.15 (d, benzylic H), 5.24 (d, benzylic H), 7.37 (m, C$_6$H$_5$).

Step B (9S)-2'-O-Acetyl-9-deoxo-12-deoxy-9,12-epoxy-11-oxo-4'''-O-[(phenylmethoxy)carbonyl]erythromycin A (9S,11S) 2'-O-acetyl-9-deoxo-12-deoxy-9,12-epoxy-4'''-O-[(phenylmethoxy)carbonyl]erythromycin A (0.95 g, 1.06 mmol), from STEP A, was dissolved in 12.4 mL of toluene. In a separate flask, NCS (N chlorosuccinimide) (1.5 g, 11.2 mmol) was dissolved in a mixture of 20.7 mL of toluene and 6.9 mL of benzene. The NCS solution was cooled to −20° C. and dimethylsulfide (DMS; 1.1 mL, 15.0 mmol) was added in one portion, with stirring. The resultant solution was stirred at −20° C. for 20 minutes. The solution of (9S,11S)-2'-O-acetyl-9-deoxo-12-deoxy-9,12-epoxy-4'''-O-[(phenylmethoxy)carbonyl]erythromycin A in toluene was added to the solution containing NCS and DMS. The reaction mixture was cooled to −25° C. and stirred at −25° C. for 2.5 hours. The reaction was quenched by the addition of 2 mL of triethylamine and washed with 25 mL of 5% sodium bicarbonate solution. The aqueous layer was extracted with 20 mL of toluene and the combined organic layers were washed with brine, dried over anhydrous sodium sulfate, filtered, and concentrated on a rotary evaporator to 0.89 g (94% yield) of the title compound.

Anal. calculated for $C_{47}H_{73}NO_{15}$ (892.104): C, 63.28; H, 8.25; N, 1.57. Found: C, 62.93; H, 8.51; N, 1.53.

FAB (M+1)+ at M/Z: 892.

$^1$HNMR (CDCl$_3$) delta 2.06 (s, COCH$_3$), 2.26 (s, N(CH$_3$)$_2$), 3.32 (s, OCH$_3$), 3.78 (dd, 9), 4.48 (d, 4''), 4.75 (dd, 2'), 5.13 (d, benzylic H), 5.24 (d, benzylic H), 7.37 (m, C$_6$H$_5$).

Step C (9S)-9-Deoxo-11,12-didoxy-9,12-epoxy-11-oxoerythromycin A

The protecting groups were removed from the 2' (O-acetyl) and 4'' (O-benzyloxycarbonyl) positions of (9S)-2'-O-acetyl-9-deoxo-11,12-dideoxy-9,12-epoxy 11-oxo-4'''-O-[phenylmethoxy)carbonyl]erythromycin A, the product of STEP B, as described in EXAMPLE 3, METHOD A, to yield 0.62 g (87% yield) of (9S)-9-deoxo-11,12-didoxy-9,12-epoxy-11-oxoerythromycin A, mp 159°–161° C.

FAB (M+H)+ at M/Z: 716 (715.930 calculated for $C_{37}H_{65}NO_{12}$).

IR bands (0.15% in CDCl$_3$): 3480 (O-H), 1755 and 1738 (C=O) cm$^1$.

$^1$HNMR was identical to the product obtained in Method A.

EXAMPLE 6

(4''E)-9,10-Didehydro-9-deoxo-4'',11,12-trideoxy-9,12-epoxy-4''-hydroxyimino-11-oxoerythromycin A

Method A

Step A

2'-O-Acetyl-4'',11-dioxoanydroerythromycin A

2'-O-Acetylanhydroerythromycin A (40 g, 52.8 mmol), from EXAMPLE 2, was treated with N chlorosuccinimide (54.0 g; 404 mmol) and dimethyl sulfide (33.0 g, 531 mmol) as described in EXAMPLE 1, STEP D, to yield 37.7 g (94% yield) of the title compound as a glass.

Anal. calculated for $C_{39}H_{63}NO_{13}$ (753.936): C, 62.13; H, 8.42; N, 1.86. Found: C, 61.71; H, 8.42; N, 1.87.

FAB (M+H)+ at M/Z: 754.

$^1$HNMR (CDCl$_3$) delta 2.07 (s, COCH$_3$), 2.28 (s, N(CH$_3$)$_2$), 3.28 (s, OCH$_3$), 4.72 (dd, 2'), 5.10 (dd, 13), 5.67 (t, 1'').

Step B (4''E)-9,10-Didehydro-9-deoxo-4'',11,12-trideoxy-9,12-epoxy-4''-hydroxyimino-11-oxoerythromycin A 2'-O-Acetyl-4'',11-dideoxy-4'',11-dioxoanhydro erythromycin A (53.97 g, 71.7 mmol), from STEP A, was dissolved in 1.0 L of methanol. Hydroxylamine hydrochloride (19.3 g, 27.8 mmol) was added in one portion at ambient temperature followed by triethylamine (40.5 mL, 285.7 mmol).

The reaction was carried out and the product isolated as described in EXAMPLE 1, STEP E. The crude product was recrystallized from hot ethyl acetate to yield 19.6 g (37.7% yield) of (4''E)-9,10-Didehydro-9-deoxo 4'',11,12-trideoxy-9,12-epoxy-4''- hydroxyimino-11-oxoerythromycin A. A 1.1 g sample of the title compound was recrystallized several times from ethyl acetate to yield 0.48 g of white crystals, mp 236°–241° C.

Anal. calculated for $C_{37}H_{62}N_2O_{12}$ (726.913): C, 61 14; H, 8.60; N, 3.85. Found: C, 61.31; H, 8.63; N, 3.83.

IR (0.5% in CHCl$_3$): 3595, 1734, 1695, 1620 cm$^{-1}$.

FAB (M+H)+ at M/Z: 727.

$^1$HNMR (CDCl$_3$) delta 1.76 (s, 10 CH$_3$), 2.32 (s, N(CH$_3$)$_2$), 3.29 (s, OCH$_3$), 3.38 (dd, 2'), 4.59 (d, 1'), 4.97 (dd, 13), 5.11 (dd, 1''), 5.31 (q, 5''), 8.73 (S$_2$=NOH). $^{13}$C NMR (CDCl$_3$) delta 93.7 (C 1''), 104.2 (C 1'), 109.1 (C 10), 159.5 (C 4''), 177.3 (C 1), 192.5 (C 9), 204.5 (C 11).

Method B

Step A

2'-O-Acetyl-4'',11-dideoxy-4'',11-dioxoanhydroerythromycin A

A solution of oxalyl chloride (24 mL, 275 mmol) in 250 mL of methylene chloride in a 1 L 3-neck flask was cooled to −70° C. in a dry ice/acetone bath. A solution of dimethyl sulfoxide (35mL, 493 mmol) in 45 mL of methylene chloride was added dropwise from an addition funnel to the oxalyl chloride solution at −70° C. After addition was complete, the reaction mixture was stirred for 5 minutes. A solution of 2'-O-acetylanhydroerythromycin A, from EXAMPLE 2, (13.9 g, 18.34 mmol) in 250 mL of methylene chloride was then added through the addition funnel. The reaction mixture was stirred for 75 min at −70° C. and quenched with 118 mL of triethylamine. The reaction mixture was allowed to warm to −30° C. and it was diluted with 250 mL of methylene chloride, then transferred to a separatory funnel. It was then washed with 3×300 mL of 6% phosphate buffer (pH 6.0) and 300 mL of brine, dried over anhydrous sodium sulfate, filtered and concentrated in vacuo to yield the title compound, which was taken on to STEP B without further purification.

Step B (4"E)-9,10-Didehydro-9-deoxo-4",11,12-trideoxy-9,12-epoxy-4"-hydroxyimino-11-oxoerythromycin A The residue from STEP A (18 g) was treated with hydroxylamine hydrochloride and triethylamine in methanol as described in EXAMPLE 6, METHOD A, STEP B. The title compound was obtained in 53% yield (from 2'-O-acetylanhydro erythromycin A) after recrystallization from ethyl acetate.

FAB (M+H)+ at M/Z: 727 (726.913 calculated for $C_{37}H_{62}N_2O_{12}$). The 300 MHz $^1H$ and $^{13}C$ NMR spectra were consistent with the proposed structure.

EXAMPLE 7

(4"R,9S)-9-Deoxo-4",11,12-trideoxy-9,12-epoxy-11-oxo-4"-[[(phenylmethoxy)carbonyl]amino]erythromycin A Step A 4"-Amino-9,10-didehydro-9-deoxo-4",11,12-trideoxy-9,12-epoxy-11-oxoerythromycin A (4"E)-9,10-Didehydro-9-deoxo-4",11,12-trideoxy-9,12-epoxy-4"-hydroxyimino-11-oxoerythromycin A (6.35 g, 8.75 mmol), the product of EXAMPLE 6, was dissolved in 250 mL of isopropyl alcohol and Raney nickel (30 g) was added. The reaction mixture was put on a Parr shaker at ambient temperature, under 4 atmospheres of hydrogen gas, for 24 hours. The reaction mixture was filtered and the filter cake was washed with isopropyl alcohol. The isopropyl alcohol washes were combined with the first filtrate and concentrated on a rotary evaporator to yield 5.90 g of a mixture of 4"-amino epimers of the title compound as a colorless foam which was taken on to the next step.

Step B (4"R)-9,10-Didehydro-9-deoxo-4",11,12-trideoxy-9,12-epoxy-11-oxo-4"[[(phenylmethoxy)carbonyl]amino]erythromycin A 4"Amino-9,10-didehydro-9-deoxo-4",11,12-trideoxy-9, 12-epoxy 11-oxoerythromycin A (2.7 g, 3.8 mmol), from STEP A, was dissolved in 110 mL of methylene chloride, and benzyloxycarbonyl N hydroxysuccinimide (1.24 g, 5.0 mmol) was added. The reaction mixture was stirred at ambient temperature for 16 h then washed with 3×80 mLs of 6% (pH 6.0) phosphate buffer solution and 80 mLs of brine. The washed organic layer was dried over anhydrous sodium sulfate and concentrated on a rotary evaporator to yield 3.2 g of residue. This residue was purified on a silica gel column (2.5×60 cm) eluted with 0.2% ammonium hydroxide in acetonitrile. Fractions numbered 185-230 were combined and concentrated on a rotary evaporator to yield 0.51 g (15% yield) of the title compound.

FAB (M+H)+ at M/Z: 847. (847.056 calculated for $C_{45}H_{70}N_2O_{13}$).

$^1$HNMR (CDCl$_3$) delta 1.74 (s, 10 CH$_3$), 2.32 (s, N(CH$_3$)$_2$), 3.30 (s, OCH$_3$), 3.32 (dd, 2'), 3.47 (d, 4", $J_{4'',5''}$=3 Hz), 4.58 (d, 1'), 4.71 (q, 5"), 4.83 (d, 1"), 5.01 (dd, 13), 5.12 (d, NH), 5.14 (s, benzylic CH$_2$), 7.36 (m, C$_6$H$_5$).

Step C (4"R, 9S)-9-Deoxo-4", 11,12-trideoxy-9,12-epoxy-11-oxo-4"-[[(phenylmethoxy)carbonyl]amino]erythromycin A (4"R)-9,10-Didehydro-9-deoxo-4", 11,12-trideoxy-9,12-epoxy-11-oxo-4"-[[(phenylmethoxy)carbonyl]amino]erythromycin A (1.68 g, 1.98 mmol), from STEP B, was dissolved in 68 mL of dry THF in a 250 mL round bottom flask which had been dried in a glassware oven overnight and flushed with nitrogen. The solution was cooled to −45° C. in a dry ice/acetonitrile bath and diisobutyl aluminum hydride (15.5 mL of 1.0M solution in toluene) was added by syringe. The reaction mixture was stirred at 45° C., under nitrogen atmosphere, for 2 hours. Methanol (1.2 mL) was added carefully in 0.1 mL portions and the reaction mixture was stirred, open to the atmosphere, at −45° C. for 5 minutes. Water (1.9 mL) was then added in 0.1 mL portions and the reaction mixture was again stirred at −45° C. for 10 minutes. The reaction mixture was allowed to warm to ambient temperature with stirring for several hours; filtered through a scintered glass funnel; and rinsed with 3×50 mL of THF or methanol. The solvent was removed on a rotary evaporator to yield 1.58 g of a colorless solid. This residue was purified on a silica gel column (40–60 mesh, 2.5 ×45 cm) which was eluted with 0.2% ammonium hydroxide in acetonitrile. The title compound was obtained (1.03 g, 60% yield) pure as a glass from fractions numbered 43–118.

FAB (M+H)+ at M/Z: 849.

$^1$HNMR (CDCl$_3$) delta 2.31 (s, N(CH$_3$)$_2$), 3.29 (s, OCH$_3$), 3.30 (dd, 2'), 3.50 (d, 4"), 3.77 (dd, 9), 4.41 (d, 1'), 4.72 (q, 5", $J_{4'',5''}$=1.5 Hz), 4.85 (d, 1"), 5.10 (dd, 13), 5.11 (d, NH), 5.15 (s, benzylic CH$_2$), 7.37 (m, C$_6$H$_5$).

EXAMPLE 8

(4"R,9S)-4"-Amino-9-deoxo-4",11,12-trideoxy-9,12-epoxy 11-oxoerythromycin A (4"R,9S)-9-Deoxo-4",11,12-trideoxy-9,12-epoxy-11-oxo-4"-[[(phenylmethoxy)carbonyl]amino]erythromycin A (0.92 g, 1.1 mmol), the product of EXAMPLE 7, was catalytically hydrogenated to remove the CBZ protecting group as described in EXAMPLE 3, METHOD A, to yield 0.7 g (89% yield) of the title compound as a glass.

Anal. calculated for $C_{37}H_{66}N_2O_{11}$ (714.945): C, 62.16; H, 9.30; N, 3.92. Found: C, 62.66; H, 9.24; N, 3.76.

FAB (M+H)+ at M/Z: 715.

IR (0.15% in CCl$_4$): 3480 (O—H), 1756 and 1736 (C=O) cm$^{-1}$.

$^1$HNMR (CDCl$_3$) delta 2.30 (s, N(CH$_3$)$_2$), 3.29 (s, OCH$_3$), 3.33 (dd, 2'), 3.77 (dd, 9), 4.41 (d, 1'), 4.68 (dq, 5", $J_{4'',5''}$=1.2 Hz), 4.83 (d, 1"), 5.13 (dd, 13).

EXAMPLE 9

(4"R,9S)-9-Deoxo-4",11,12-trideoxy-9,12-epoxy-4"-[[(dimethyamino)methylene]amino]-11-oxoerythromycin A (4"R,9S)-4-Amino-9-deoxo-4",11,12-trideoxy-9,12-epoxy-11-oxoerythromycin A (The product of EXAMPLE 8) (0.20 g, 0.28 mmol) was dissolved in 2.5 mL of freshly distilled methylene chloride in a flask which had been dried in a glassware oven overnight. Dimethylformamide dimethyl acetal (0.18 mL, 1.35 mmol) was added in one portion and the reaction mixture was stirred at ambient temperature for 20 hours. The reaction mixture was then poured into 5 mL of methylene chloride and washed with 5 mL of 5% sodium bicarbonate solution. The aqueous layer was extracted with 3×5 L of methylene chloride and the organic layers were combined. The combined organic layers were washed with 10 mL of brine, dried over anhydrous sodium sulfate, filtered and concentrated to 0.15 g of a yellow glass. The yellow residue was purified on a silica gel column which was eluted with a mixture of heptane, chloroform, methanol and ammonia (6:3:1:0.2, v/v/v/v). Fractions numbered 94–105 were combined and concentrated to yield 21.4 mg (10% yield) of the title compound as a foamed glass.

FAB (M+H)+ at M/Z: 770 (770.025 calculated for $C_{40}H_{34}N_3O_{11}$).

$^1$HNMR (CDCl$_3$) delta 2.30 (s, N(CH$_3$)$_2$), 2.55 (bs, NCH$_3$), 2.90 (bs, NCH$_3$), 3.28 (dd, 2'), 3.30 (s, OCH$_3$), 3.77 (dd, 9), 4.43 (d, 1'), 4.62 (bm, 5''), 4.93 (d, 1''), 5.12 (dd, 13), 7.25 (bs, N=CH—N).

EXAMPLE 10

(4''R,9S) 4''-Acetylamino-9-deoxo-4'',11,12-trideoxy-9,12-epoxy-11-oxoerythromycin A (4''R,9S) 4''-Amino-9-deoxo-4'',11,12-trideoxy-9,12-epoxy-11-oxoerythromycin A (the product of EXAMPLE 8) (34.7 mg, 0.049 mmol) was dissolved in 2 mL of methanol in a 25 mL round bottom flask. The solution was cooled to 0° C. in an ice bath. Triethylamine (4.9 mg, 0.048 mmol) was added to the solution with stirring, followed by acetic anhydride (8.0 mg, 0.78 mmol). After one hour of stirring at 0° C., the reaction mixture was diluted with 40 mL of ethyl acetate. The resultant solution was washed with 3×20 mL of 4% sodium bicarbonate solution and 20 mL of brine, dried over anhydrous sodium sulfate, filtered and concentrated on a rotary evaporator to give 29 mg (79% yield) of the title compound.

FAB (M+H)+ at M/Z: 756 (756.983 calculated for $C_{39}H_{68}N_2O_{12}$)

$^1$HNMR (CDCl$_3$) delta 2.07 (s, NCOCH$_3$). 2.31 (s, N(CH$_3$)$_2$), 3.28 (s, OCH$_3$), 3.32 (dd, 2'), 3.78(dd, 9), 3.83 (bd, 4'', $J_{4'',5''}$=1.2 Hz), 4.41 (d, 1''), 4.73 (dq, 5''), 5.14 (dd, 13), 5.78 (bd, NHCO).

EXAMPLE 11

(4''R,9S)-9-Deoxo-4'',11,12-trideoxy-9,12-epoxy-4''-[(methylsulphonyl)amino]-11-oxoerythromycin A The product of EXAMPLE 8 (4''R,9S) 4''-amino-9-deoxo-4'',11,12-trideoxy-9,12-epoxy-11-oxoerythromycin A (0.075 g, 0.105 mmol) was added to a 25 mL round bottom flask, followed by 0.07 g (0.507 mmol) of finely ground potassium carbonate and 8 mL of methylene chloride. The suspension was cooled in an ice bath and stirred under a nitrogen atmosphere. A solution of methanesulfonic anhydride (0.057 g, 0.33 mmol) in 1 mL of methylene chloride was prepared and added to the suspension by syringe. The reaction mixture was stirred at 0° C., under nitrogen atmosphere, for 40 minutes, at which time it was diluted with 20 mL of methylene chloride and transferred to a separatory funnel. It was washed with 3×15 mL of 4% sodium bicarbonate solution, once with 15 mL of brine, dried over anhydrous sodium sulfate, filtered and concentrated on a rotary evaporator to yield a colorless solid residue. The residue was purified on a silica gel column (1.1×30 cm) which was eluted with 0.3% ammonium hydroxide in acetonitrile. Fractions numbered 11–20 were combined to yield 0.05 g (63% yield) of pure (4''R,9S)-9-deoxo-4'',11,12-trideoxy-9,12-epoxy-4''-[(methylsulphonyl)amino]-11-oxoerythromycin A.

FW calculated for $C_{38}H_{68}N_2O_{13}S$ (793.031).

$^1$HNMR (CDCl$_3$) delta 2.30 (s, N(CH$_3$)$_2$), 3.03 (s, NSO$_2$CH$_3$), 3.22 (d, 4'', $J_{4'',5''}$=1.2 Hz), 3.29 (s, OCH$_3$), 3.31 (dd, 2'), 3.78 (dd, 9), 4.39 (d, 1'), 4.65 (bd, NHSO$_2$), 4.78 (dq, 5''), 4.84 (d, 1''), 5.12 (dd, 13).

EXAMPLE 12

(4''R,9S)-9-Deoxo-4'', 11,12-trideoxy-9,12-epoxy-11-oxo-4''-[(phenylmethyl)amino]erythromycin A (4''R,9S)-4''-Amino-9-deoxo-4'',11,12-trideoxy-9,12-epoxy-11-oxoerythromycin A (0.06 g, 0.084 mmol), the product of EXAMPLE 8, and 0.1 g (0.98 mmol) of benzaldehyde were dissolved in 3 mL of acetonitrile (CH$_3$CN). This solution was added, with stirring, to a suspension of sodium cyanoborohydride (0.022 g, 0.350 mmol) in 2 mL CH$_3$CN in a 10 mL round bottom flask. To the resultant solution, 0.05 mL of 3N hydrochloric acid solution was added. Some foaming was observed. The reaction mixture was stirred at ambient temperature for one hour. The reaction was quenched by the addition of 1 mL of 4% sodium bicarbonate solution and transferred to a separatory funnel, where it was diluted with 40 mL of CH$_2$Cl$_2$. The entire solution was washed with 3×20 mL of 4% sodium bicarbonate solution. The combined organic layers were washed with 20 mL of brine, dried over anhydrous sodium sulfate, filtered and concentrated to an oil. The oil was purified on a column (1.1×30 cm) which was packed with 5 g silica gel in CH$_3$CN and eluted with 0.2% ammonium hydroxide in CH$_3$CN. Fractions numbered 11–34 were combined and concentrated to yield 0.043 g. (64% yield) pure title compound.

FAB (M+H)+ at M/Z: 805 (805.071 calculated for $C_{44}H_{72}N_2O_{11}$.

$^1$HNMR (CDCl$_3$) delta 2.31 (s, N(CH$_3$)$_2$), 3.28 (s, OCH$_3$), 3.32 (dd, 2'), 3.76 (dd, 9), 3.79 (d, benzylic H), 3.94 (d, benzylic H), 4.44 (d, 1'), 4.74 (dq, 5'', $J_{4'',5''}$=1.5 Hz), 4.79 (d, 1''), 5.13 (dd, 13).

EXAMPLE 13

(4''R,9S,11S) 4''-Amino-9-deoxo-4'',12-dideoxy-9,12-epoxyerythromycin A

Method A

Step A (4''E,9S,11S)-9-Deoxo-4'',12-dideoxy-9,12-epoxy-4''-hydroxyiminoerythromycin A The product of EXAMPLE 6 (4 g, 5.5 mmol) was dissolved in a mixture of 50 mL of dimethoxyethane (dried over 4A molecular sieves) and 3 mL of isopropyl alcohol. In a separate 500 mL round bottom flask (which had been dried in the glassware oven overnight and was fitted with a calcium chloride drying tube) a solution of lithium borohydride (2.2 g, 101 mmol) was prepared in the same solvent mixture. Heat and some hydrogen gas were generated. It was necessary to cool the flask in a water bath to keep the borohydride solution at room temperature. The solution of (4''E)-9,10

Didehydro-9-deoxo-4",11,12 trideoxy-9,12-epoxy-11-oxo 4"hydroxyiminoerythromycin A was added to the borohydride solution. dropwise from an addition funnel, over a 10 minute period. The reaction mixture was kept at ambient temperature by immersing the reaction flask in a water bath, and it was stirred at ambient temperature for six hours. The reaction was monitored by TLC (elution solvent: chloroform/methanol/ammonia 9/1/0.2) at one hour intervals. After six hours the reaction mixture was kept at −5° C. overnight, then stirred at ambient temperature for an additional hour. The reaction mixture was poured into 100 mL of 50% aqueous methanol and swirled. Methylene chloride (200 mL) and 5% sodium bicarbonate solution were added and the resultant solution was stirred at ambient temperature for 5 minutes and then allowed to stand for 10 minutes without stirring. The solution was transferred to a separatory funnel and extracted with 3×300 mL of methylene chloride. The combined methylene chloride layers were washed with 300 mL of brine, dried over anhydrous sodium sulfate, filtered, and concentrated on a rotary evaporator to yield 3.74 g of residue. The residue was dissolved in 150 mL of methanol and the solution was kept at ambient temperature for 5 days to decompose borate ester complexes. The methanol was removed on a rotary evaporator and the 3.34 g residue was combined with 3.59 g of similarly prepared material and was purified on a silica gel column which was eluted with a mixture of chloroform, methanol and ammonia (9:1:0.5) to yield 3.3 g (41%) of the title compound from fractions numbered 61–120.

FAB (M+H)+ at M/Z: 731 (730.945 calculated for $C_{37}H_{66}N_2O_{12}$).

$^1$HNMR (CDCl$_3$) delta 2.29 (s, N(CH$_3$)$_2$), 3.23 (dd, 2'), 3.30 (s, OCH$_3$), 3.68 (dd, 9), 4.29 (dd, 11), 4.41 (d, 1'), 4.97 (dd, 13), 5.10 (dd, 1"), 5.15 (q, 5"), 8.80 (bs, N—OH).

Step B (9S,11S)-4"-Amino-9-deoxo-4",12-dideoxy-9,12-epoxyerthromycin A (4"E,9S,11S)-9-Deoxo-4",12-dideoxy-9,12-epoxy-4"-hydroxyiminoerythromycin A, the product of STEP A, (2.02 g, 2.76 mmol) was hydrogenated for 3 days as described in EXAMPLE 3, METHOD A, with methanol: 10% acetic acid as solvent. The catalyst was removed by filtration and the filter cake was washed with 800 mL MeOH, 800 mL MeOH: 10% concentrated. NH$_4$OH and finally with 800 mL of CH$_2$Cl$_2$. The filtrate and washings were combined and evaporated. The residue was dissolved in ETOAc and was washed with a mixture of brine and concentrated NH$_4$OH (9/1 v/v) The EtOAc layer was dried (Na$_2$SO$_4$), filtered and evaporated to provide 1.75 g of a mixture of 4"-amino epimers of the title compound.

FAB (M+H)+ at M/Z: 717 (716.961 calculated for $C_{37}H_{68}N_2O_{11}$).

Step C (4"R,9S,11S)-9-Deoxo-4",12-dideoxy-9,12-epoxy-4"-[[(phenylmethoxy)carbonyl]amino]erythromycin A The product of STEP B (1.74 g, 2.43 mmol) was converted to 2.39 g of crude 4"-CBZ derivative as described in EXAMPLE 7, STEP B. The title compound was obtained, after purification on a silica gel column (CH$_3$CN/concentrated. NH$_4$OH, 200/1 v/v) providing 0.88 g of a white glass.

FAB (M+H)+ at M/Z: 851 (851.097 calculated for $C_{45}H_{74}N_2O_{13}$).

$^1$HNMR (CDCl$_3$) delta 2.28 (s, N(CH$_3$)$_2$), 3.21 (dd, 2'), 3.31 (s, OCH$_3$), 3.47 (d, 4"), 3.65 (dd, 9), 4.28 (dd, 11), 4.42 (d, 1'), 4.67 (dq, 5", J$_{4",5"}$=1.2 Hz), 4.88 (d, 1"), 5.07 (dd, 13), 5.10 (bd, NH), 5.11 (d, benzylic H), 5.15 (d, benzylic H), 7.36 (m, C$_6$H$_5$).

Step D (4"R,9S,11S)-4"-Amino-9-deoxo-4",12 dideoxy-9,12-epoxyerythromycin A

The product of STEP C (0.88 g, 1.03 mmol) was deprotected as described in EXAMPLE 14, STEP D to yield 0.73 g (99% yield) of the title compound as a colorless solid.

FAB (M+H)+ at M/Z: 717 (716.961 calculated for $C_{37}H_{68}N_2O_{11}$).

IR (KBr): 1735 (C=O) cm$^{-1}$.

$^1$HNMR (CDCl$_3$) delta 2.28 (s, N(CH$_3$)$_2$), 3.22 (dd, 2'), 3.32 (s, OCH$_3$), 3.66 (dd, 9), 4.29 (bd, 11), 4.43 (d, 1'), 4.61 (dq, 5", J$_{4",5"}$=1.2 Hz), 4.88 (d, 1"), 5.09 (dd, 13).

Method B (4"R,9S,11S)-4"-Amino-9-deoxo4",12-dideoxy9,12-epoxyerythromycin A

The product of EXAMPLE 8, (4"R,9S,)-4"-amino-9-deoxo-4",11,12-trideoxy-9,12-epoxy-11-oxoerythromycin A, (0.05 g, 0.07 mmol), was dissolved in 2.5 mL of methanol. This solution was cooled in an ice/water bath. A separate solution was prepared (by dissolving 0.034 g of sodium borohydride (0.89 mmol) in 0.6 mL of water) and cooled in an ice/water bath. The sodium borohydride solution was added by syringe into the methanol solution in one portion. The reaction mixture was stirred for 1 h with a magnetic stirrer. The reaction mixture was then diluted with 30 mL of ethyl acetate, washed with 3×20 mL of 4% sodium bicarbonate solution, 20 mL of brine, dried over anhydrous sodium sulfate, filtered, and concentrated on a rotary evaporator to yield 0.031 g (62% yield) of the title compound.

FAB (M+H)+ at M/Z: 717 (716.961 calculated for $C_{37}H_{68}N_2O_{11}$).

The 300 MHz $^1$HNMR was identical to the product of METHOD A, STEP D.

EXAMPLE 14

(4"S,9S)-4"-Amino-9-deoxo-4",11,12-trideoxy-9,12-epoxy-11-oxoerythromycin A

Step A

4"-Amino-9,10-didehydro-9-deoxo 4",11,12-trideoxy-9,12-epoxy-11-oxoerythromycin A The product of EXAMPLE 6 (31.69 g, 43.6 mmol) was dissolved in 1800 mL of methanol. Raney nickel (158 g) and ammonium hydroxide (200 mL) were added. The hydrogenation mixture was put on a Parr shaker, at ambient temperature, under 4 atmospheres of hydrogen gas for 24 hours. The reaction mixture was filtered and concentrated on a rotary evaporator to yield 26 g of the title compound as a mixture of 4"-amino epimers, which was carried on to the next step without purification.

Step B (4"S)-9,10-Didehydro-9-deoxo-4",11,12-trideoxy-9,12-epoxy-11-oxo-4"-[[(phenylmethoxy[carbonyl]amino]erythromycin A 4"Amino-9,10-didehydro-9-deoxo-4",11,12-trideoxy-9,12-epoxy-11-oxoerythromycin A (26 g, 35.8 mmol),- from STEP A, was dissolved in 500 mL of methylene chloride. Carbobenzyloxy N-hydroxysuccinimide (9.6 g, 38.5 mmoL) was added and the reaction was carried out as described in EXAMPLE 7, STEP B. The crude product (34.8 g) was purified by silica gel column chromatography. The column was packed with 2 Kg of silica gel and eluted with acetonitrile containing 0.6% ammonium hydroxide. The solvent was removed (on a rotary evaporator) from the fractions containing the title compound to yield 14.4 g (40% yield) of (4"S) 9,10-didehydro-9-deoxo-4",11,12-trideoxy-9,12-epoxy-11-oxo4"- [[(phenylmethoxy[carbonyl]amino]erythromycin A.

FAB (M+H)+ at M/Z: 847 (847.056) calculated for $C_{45}H_{20}N_2O_{13}$.

IR (0.15% in $CCl_4$): 3440 (NH), 1734 (lactone, CBZ), 1697 (11 C=O), 1620 (C=C) cm−1.

$^1$HNMR ($CDCl_3$) delta 1.74 (s, 10 $CH_3$), 2.32 (s, N($CH_3$)$_2$), 3.22 (s, $OCH_3$), 3.37 (dd, 2'), 3.39 (t, 4", $J_{4'',5''}=10$ Hz), 4.15 (d, q, 5"), 5.03 (dd, 13), 5.07 (d, benzylic H), 5.16 (d, benzylic H), 5.23 (d, NH), 7.37 (m, $C_6H_5$).

Step C (4"S,9S)-9-Deoxo-4",11,12-trideoxy-9,12-epoxy-11-oxo4"-[[(phenylmethoxy)carbonyl]amino]erythromycin A (4"S)-9,10-Didehydro-9-deoxo-4"11,12-trideoxy-9,12-epoxy-11-oxo 4"-[[(phenylmethoxy[carbonyl]amino]erythromycin A (14 g, 16 mmol), from STEP B, was treated with diisobutylaluminum hydride as described in EXAMPLE 7, STEP C to yield 6.2 g (44% yield) of pure title compound after chromatography.

Anal calculated for $C_{45}H_{71}N_2O_{13}$ (849.081): C, 63.66; H, 8.55; N, 3.30. Found: C, 63.49; H, 8.59; N, 3.31.

FAB (M+H)+ at M/Z: 849.

IR (0.15% in $CCl_4$) 3480 (O—H), 3445 (sharp; N—H), 1755 (11 C=O) and 1734 Lactone, CBZ cm−1.

$^1$HNMR ($CDCl_3$): delta 2.30 (s, N($CH_3$)$_2$), 3.21 (s, $OCH_3$), 3.29 (dd, 2'), 3.39 (t, 4"), 3.78 (dd, 9), 4.12 (dq, 5", $J_{4'',5''}=10.5$ Hz), 4.34 (d, 1'), 4.87 (d, 1"), 5.10 (d, benzylic H), 5.13 (dd, 13), 5.16 (d, benzylic H), 5.22 (d, NH), 7.36 (m, $C_6H_5$).

Step D (4"S,9S)-4"-Amino-9-deoxo-4",11,12-trideoxy-9,12-epoxy-11-oxoerythromycin A (4"S,9S)-9-Deoxo-4", 11,12-trideoxy-9,12-epoxy-11-oxo-4"[[(phenylmethoxy)carbonyl]amino]erythromycin A (7.4 g, 8.45 mmol), from STEP C, was dissolved in 225 mL of methanol. Raney nickel (14.8 g) and ammonium hydroxide (25 mL) were added and the reaction was carried out as described in EXAMPLE 14, STEP A. The crude product was dissolved in 200 mL of methylene chloride and washed with 200 mL of 5% sodium bicarbonate. The aqueous layer was extracted with 3×150 mL of methylene chloride and the methylene chloride layers were all combined. The combined organic layers were washed with 300 mL of brine, dried over anhydrous sodium sulfate and concentrated on a rotary evaporator to yield 5.65 g (93.5% yield) of the title compound as a white glass.

Anal. calculated for $C_{37}H_{66}N_2O_{11}$ (714.945): C, 62.16; H, 9.31; N, 3.92. Found: C, 62.66; H, 9.24; N, 3.76.

FAB (C+H)+ at M/Z: 715.

$^1$HNMR ($CDCl_3$) delta 2.31 (s, N($CH_3$)$_2$), 3.25 (s, $OCH_3$), 3.33 (dd), 3.78 (dd, 9), 4.07 (dq, 5", $J_{4'',5''}=9.6$ Hz), 4.40 (d, 1'), 4.83 (d, 1"), 5.13 (dd, 13).

IR (0.15% in $CCl_4$): 3490 (OH), 1755 (11 C=O), 1738 (lactone) cm−1.

EXAMPLE 15

(4"S,9S,11S)-4"-Amino-9-deoxo-4",12-dideoxy-9,12-epoxyerythromycin A

Method A

Step A (9S,11S)-4"-Amino-9-deoxo-4",12-dideoxy-9,12-epoxyerythromycin A

The product of EXAMPLE 13, METHOD A, STEP A, (4"E,9S,11S)-9-deoxo-4",12-dideoxy-9,12-epoxyerythromycin A (2.23 g, 3.05 mmol) was reduced with Raney nickel (12 g) using the procedure described in EXAMPLE 14, STEP A. The reduction produced 2.17 g of the title compound as a mixture of 4"-amino epimers.

The desired amino epimer with the natural configuration at 4" was obtained as described in STEPS B and C.

Step B (4"S,9S,11S)-9-Deoxo-4",12-dideoxy-9,12-epoxy-4"-[[(phenylmethoxy)carbonyl]amino]erythromycin A The product of STEP A (2.17 g, 3.05 mmol) was converted to the 4"-CBZ derivative with carbobenzoxycarbonyl N-hydroxysuccinimide (1.05 g, 4.2 mmol) in methylene chloride as described in EXAMPLE 7, STEP B. The title compound was obtained, after purification on a silica gel column eluted with $CH_3CN$: 0.2% concentrated. $NH_4OH$, in 56% yield (1.46 g).

FAB (M+H)+ at M/Z: 851 (851.097 calculated for $C_{45}H_{74}N_2O_{13}$).

$^1$HNMR ($CDCl_3$) delta 2.27 (s, N($CH_3$)$_2$), 3.21 (dd, 2'), 3.23 (s, $OCH_3$), 3.49 (t, 4"), 3.67 (dd, 9), 4.08 (dq, 5", $J_{4'',5''}=10$ Hz), 4.29 (3H, m, 3, 11, 1'), 4.89 (d, 1"), 5.08 (d, benzylic H), 5.12 (dd, 13), 5.17 (d, benzylic H), 5.25 (d, NH), 7.36 (m, $C_6H_5$)

Step C (4"S,9S,11S)-4"-Amino-9-deoxo-4",12-dideoxy-9,12-epoxyerythromycin A The product of STEP B, (4.37, 5.1 mmol) was deprotected to the amino derivative with 9.5 g of Raney nickel as described in EXAMPLE 14, STEP A. The title compound was obtained in 91% yield (3.36 g).

Anal. calculated for $C_{37}H_{68}N_2O_{11}$ (716.961): C, 61.99; H, 9.56; N, 3.91. Found: C, 61.81; H, 9.47; N, 3.84.

FAB (M+H)+ at M/Z: 717.

IR ((0.15% in $CCl_4$): 3636 and 3480 (O—H and N—H), 1739 (C=O) cm−1.

$^1$HNMR ($CDCl_3$) delta 2.30 (s, N($CH_3$)$_2$), 3.22 (dd, 2'), 3.28 (s, $OCH_3$), 3.67 (dd, 9), 4.00 (dq, 5", $J_{4'',5''}=10$ Hz), 4.29 (2H, m, 3, 11), 4.40 (d, 1'), 4.85 (d, 1"), 5.09 (dd, 13).

Method B

(4"S,9S,11S)-4"-Amino-9-deoxo-4",12-dideoxy-9,12-epoxyerythromycin A

The product of EXAMPLE 14, (4"S,9S)-4"-amino-9-deoxo-4",11,12-trideoxy-9,12-epoxy-11-oxoerythromycin A (0.082 g, 0.11 mmol), was reduced, using sodium borohydride (0.56 g, 1.48 mmol), as described in EXAMPLE 13, METHOD B. The title compound was obtained in 74% yield (0.058 g) as a colorless glass.

FAB (M+H)+ at M/Z: 717 (716.961 calculate for $C_{37}H_{68}N_2O_{11}$).

The $^1$HNMR spectrum was identical to the product of METHOD A.

EXAMPLE 16

(4"S,9S)-9-Deoxo-4",11,12-trideoxy-9,12-epoxy-4"-(methylsulfonyl)amino-11-oxerythromycin A (4"S,9S)-4"-Amino-9-deoxo-4",11,12-trideoxy-9,12-epoxy-11-oxerythromycin A (0.10 g, 0.14 mmol), the product of EXAMPLE 14, was treated with methanesulfonic anhydride (0.075 g, 0.43 mmol) as described in EXAMPLE 11 for the 4"R isomer to yield 0.06 g (54% yield) of the title compound.

FAB (M+H)+ at M/Z: 793 (793.031 calculated for $C_{38}H_{68}N_2O_{12}S$).

$^1$HNMR (CDCl$_3$) delta 2.33 (bs, N(CH$_3$)$_2$), 3.02 (s, NSO$_2$CH$_3$), 3.15 (t, 4", J$_{4'',5''}$=10 Hz), 3.24 (s, OCH$_3$), 3.31 (bm, 2'), 3.78 (dd, 9), 4.19 (dq, 5"), 4.35 (d, 1"), 4.86 (2H, bd, 1", NHSO$_2$), 5.13 (dd, 13).

EXAMPLE 17

(9S,11S)-4"-O-Aminocarbonyl-9-deoxo-12-deoxy-9,12-epoxyerythromycin A

Step A (9S,11S)-2'-O-Acetyl-9-deoxo-12-deoxy-9,12-epoxy-11-O-trimethylsilyl-4"-O-[(phenylmethoxy)carbonyl]erythromycin A The product of EXAMPLE 5, METHOD B, STEP A (0.62 g, 0.69 mmol) was dissolved in 93 mL of methylene chloride. Imidazole (0.33 g, 46.8 mmol) was added to the clear solution with stirring, followed by trimethylsilyl chloride (0.43 mL, 0.37 g, 3.4 mmol). A white mist and heat were evolved during the addition and a precipitate formed. The cloudy suspension was stirred for one hour at ambient temperature. The precipitate became redissolved. The solution was transferred to a separatory funnel and washed with 100 mL of 5% sodium bicarbonate solution. The aqueous layer was extracted with 2×50 mL of methylene chloride and the organic layers were combined. The combined organic layers were washed with 100 mL of brine, dried over anhydrous sodium sulfate, filtered, and concentrated on a rotary evaporator to 0 59 g (89% yield) of the title compound.

FAB (M+H)+ at M/Z: 966 (966.302 calculated for $C_{50}H_{83}NO_{15}Si$).

$^1$HNMR(CDCl$_3$) delta 0.15 (s, Si(CH$_3$)3), 2.06 (s, COCH$_3$), 2.25 (s, N(CH$_3$)$_2$), 3.32 (s, OCH$_3$), 3.65 (dd, 9), 4.20 (d, 11), 4.48 (d,4"), 4.76 (dd, 2'), 5.05 (dd, 13), 5.13 (d, benzylic H), 5.24 (d, benzylic H), 7.36 (m, C$_6$H$_5$).

Step B (9S,11S)-2'-O-Acetyl-9-deoxo12-deoxy-9,12-epoxy-11-O-trimethylsilylerythromycin A The benzyloxycarbonyl (CBZ) group was removed from (9S,11S)-2'-O-acetyl-9-deoxo-12-deoxy-9,12-epoxy-11-O-trimethylsilyl-4"-O-[(phenylmethoxy)carbonyl]erythromycin A (0.59 g, 0.6 mmol), the product of STEP A, by catalytic hydrogenation as described in EXAMPLE 3, METHOD A to yield 0.49 g (96% yield) of the title compound.

FAB (M+H)+ at M/Z: 832 (832.166 calculated for $C_{42}H_{77}NO_{13}Si$).

$^1$HNMR (CDCl$_3$) delta 0.17 (s, Si(CH$_3$)$_3$), 2.08 (s, COCH$_3$), 2.28 (s, N(CH$_3$)$_2$), 3.04 (bt, 4"), 3.32 (s, OCH$_3$), 3.66 (dd, 9), 4.20 (d, 11), 4.77 (dd, 2), 5.06 (dd, 13).

Step C (9S,11S)-2"-O-Acetyl-9-deoxo-12-deoxy-9,12-epoxy-4"-O-(1-imidazolyl)carbonyl-11-O-trimethylsilylerythromycin A (9S,11S) 2'-O-Acetyl-9-deoxo-12-deoxy-9,12-epoxy-11-O-trimethylsilylerythromycin A (0.47 g, 0.57 mmol), from STEP B, was dissolved in 5 mL of methylene chloride. N,N'-Carbonyldiimidazole (0.37 g, 2.3 mmol) was added, followed by N,N-dimethylaminopyridine (0.28 g, 0.4 mmol). The reaction mixture was stirred at ambient temperature for three hours, at which time it was diluted by the addition of 50 mL of methylene chloride. The reaction mixture was transferred to a separatory funnel and washed with 100 mL of 0.3M (pH 5.0) phosphate buffer solution followed by 100 mL of 5% sodium bicarbonate solution. The combined aqueous layers were extracted with 2×50 mL of methylene chloride. The organic layers were combined, washed with 100 mL of brine, dried over anhydrous sodium sulfate, filtered and concentrated on a rotary evaporator to 0.37 g (70%) of the title compound.

FAB (M+H)+ at M/Z: 926 (926.240 calculated for $C_{46}H_{79}N_3O_{14}Si$).

$^1$HNMR (CDCl$_3$) delta 0.17 (s, Si(CH$_3$)$_3$, 2.14 (s, COCH$_3$), 2.29 (s, N(CH$_3$)$_2$), 3.34 (s, OCH$_3$), 3.66 (dd, 9), 4.21 (d, 11), 4.79 (d, 4"), 7.10/7.44/8.13 (3H, imidazolide).

Step D (9S,11S)-2'-O-Acetyl-4"-O-aminocarbonyl-9-deoxo-12-deoxo-9,12-epoxy-11-O-trimethylsilylerythromycin A (9S,11S)-2"-O-Acetyl-9-deoxo-12-deoxy-9,12-epoxy-4"-O-(1-imidazolyl)carbonyl-11-O-trimethylsilylerythromycin A (0.36 g, 0.39 mmol), from STEP C, was dissolved in 4 mL of acetonitrile. Concentrated (14.8M) ammonium hydroxide (4 mL, 59.2 mmol) was added with stirring at ambient temperature. The reaction mixture was stirred at ambient temperature for 40 minutes and then quenched with 0.3M (pH 5.0) phosphate buffer solution. The quenched reaction mixture was diluted with 100 mL of methylene chloride, and the layers separated. The organic layer was washed with 2×50 mL of 5% sodium bicarbonate solution and the aqueous layers were combined. The combined aqueous layers were extracted with 2×50 mL of methylene chloride. The combined organic layers were washed with 100 mL of brine, dried over anhydrous sodium sulfate, filtered and concentrated on a rotary evaporator to yield 0.25 g (73%) of the title compound.

FAB (M+H)+ at M/Z: 875 (875.192 calculated for $C_{43}H_{78}N_2O_{14}Si$).

$^1$HNMR (CDCl$_3$) delta 0.17 (s, Si(CH$_3$)$_3$), 2.09 (s, COCH$_3$), 2.30 (s, N(CH$_3$)$_2$), 3.33 (s, OCH$_3$), 3.65 (dd, 9), 4.20 (d, 11), 4.56 (d, 4″), 4.79 (dd, 2′), 5.05 (dd, 13).

Step E (9S,11S)-4″-O-aminocarbonyl-9-deoxo-12-deoxy-9,12-epoxyerythromycin A

The product from STEP D, (9S,11S)-2′-O-Acetyl-4″-O-aminocarbonyl-9-deoxo-12-deoxy-9,12-epoxy-11-O-trimethylsilylerythromycin A (0.25 g, 0.28 mmol), was dissolved in 10 mL of methanol and the solution kept at ambient temperature for 3 days to remove the 2′ acetyl ester. The methanol was evaporated and the residue (0.18 g) was dissolved in 0.5 mL of tetrahydrofuran (THF). Methylene chloride (1 mL) was added with swirling, followed by tetra-n-butyl ammonium fluoride (0.22 mL, 56.6 mmol). The reaction mixture was stirred at ambient temperature for 15 minutes, at which time 50 mL of benzene was added. The reaction mixture was washed with 100 mL of 5% sodium bicarbonate solution and 100 mL of brine, dried over anhydrous sodium sulfate, filtered, and concentrated on a rotary evaporator to give 0.1 g of residue. The residue was recrystallized from a mixture of methylene chloride and hexane (5/1 v/v) to yield 0.03 g (18% yield) of (9S,11S)-4″-O-aminocarbonyl-9-deoxo-12-deoxy-9,12epoxyerythromycin A.

Anal. calculated for $C_{38}H_{68}N_2O_{13}H_2O$ (778.987): C, 58.59; H, 9.06; N, 3.60. Found: C, 58.59; H, 8.73; N, 3.57.

FAB (M+H)+ at M/Z: 761 (760.971 calculated for $C_{38}H_{68}N_2O_{13}$)

$^1$H NMR (CDCl$_3$) delta 2.29 (s, N(CH$_3$)$_2$), 3.21 (dd, 2′), 3.33 (s, OCH$_3$), 3.66 (dd, 9), 4.29 (dd, 11), 4.38 (3H, m, 3,4″,5″), 5.09 (dd, 13).

IR (0.15% in CCl$_4$): 1710 (OCONH$_2$), 1740 (Lactone) cm$^{-1}$.

EXAMPLE 18

(9S)-9-Deoxo-11,12-dideoxy-9,12-epoxy-11-hydroxyiminoerythromycin A

The product of EXAMPLE 5 (1.11 g, 1.55 mmol) was dissolved in 15 mL of absolute ethanol. Hydroxylamine hydrochloride (1.27 g, 18.28 mmol) and triethylamine (1.50 mL, 10.72 mmol) were added to the solution at ambient temperature and the reaction mixture was heated in an oil bath to 80° C. The reaction mixture was stirred for 3 days at 80 C. and for three days at 70° C. The reaction was monitored daily with HPLC on a C$_8$ reverse phase column 4.6×250 mm (YMC, INC); eluent: 55% water, 40% acetonitrile and 5% methanol containing 10 g/L sodium acetate and 0.5 mL glacial acetic acid; isocratic elution; flow rate=1.00 mL/min.). After six days the reaction mixture was diluted with 150 mL of 4% sodium bicarbonate solution and brought to pH 10 with 3 mL of concentrated ammonium hydroxide. The aqueous mixture was extracted with 3×33 mL of chloroform. The combined chloroform extracts were washed with 75 mL of 4% sodium bicarbonate, dried over anhydrous sodium sulfate, filtered and concentrated on a rotary evaporator to give 1.1 g of white glass. This crude product was purified on a silica gel column (2.4×44 cm) which was eluted with a step-gradient of methanol in chloroform containing 0.2% ammonium hydroxide. The methanol concentration was increased from 2% in the initial 500 mL of eluent to 5% in the final 500 mL of eluent. It was increased by 0.5% each step (500 mL).

(9S,11Z)-9-Deoxo-11,12-dideoxy-9,12-epoxy-11-hydroxyiminoerythromycin A (0.14 g) was collected from fractions numbered 90–100, mp 218°–235° C. (CH$_3$CN).

Anal. calculated for $C_{37}H_{66}N_2O_{12}$ (730.945): C, 60.80; H, 9.10; N, 3.82. Found: C, 60.82; H, 9.26, N, 4.19.

IR (0.15% solution in CCl$_4$): 3595, 1738 cm$^{-1}$.

$^1$HNMR (CCDCl$_3$) delta 2.32 (s, N(CH$_3$)$_2$, 3.05 (t, 4″), 3.34 (s, OCH$_3$), 3.35 (dd, 2′), 3.55 (dd, 9), 4.57 (d, 1′), 4 74 (d, 1″), 4.92 (dd, 13).

$^1$HNMR (SO(CD$_3$)$_2$) delta 10.88 (s, NOH).

(9S,11E)-9-Deoxo-11,12-dideoxy-9,12-epoxy-11-hydroxyiminoerythromycin A (0.35 g) was collected from fractions numbered 115–150, mp 145°–148° C. (CH$_3$CN).

Anal. calculated for $C_{37}H_{66}N_2O_{12}$ (730.945): C, 60.80; H, 9.10; N, 3.83. Found: C, 60.35; H, 9.36; N, 3.82.

IR (0.15% solution in CCl$_4$): 3595, 1738 cm$^{-1}$.

$^1$HNMR (CDCl$_3$) delta 2.31 (s, N(CH$_3$)$_2$), 3.02 (t, 4″), 3.26 (dd, 2′), 3.30 (s, OCH$_3$), 3.82 (dd, 9), 4.39 (d, 1′), 4.85 (d, 1″), 5.21 (dd, 13).

$^1$HNMR (SO(CD$_3$)$_2$) delta 10.79 (s, NOH).

EXAMPLE 19

(9S,11S)-11-Amino-9-deoxo-11,12-deoxy-9,12-epoxyerythromycin A

Method A

A mixture of the two isomeric products from EXAMPLE 18 (0.21 g, 0.29 mmol) was reduced, using Raney nickel catalyst and methanol solvent, as described in EXAMPLE 7, STEP A. After semi-preparative scale chromatography with HPLC on a C$_8$ reverse phase column 20×250 mm; eluent: 35% CH$_3$CN in water containing 20 g/L sodium acetate trihydrate and 1.0 mL/L glacial acetic acid; isocratic elution; flow rate=12 mL/min) to separate out the two isomeric amine products, the title compound was obtained (0.047 g) in 23% yield, mp 168°–172° C. (CH$_3$CN).

Anal. calculated for $C_{37}H_{68}N_2O_{11}$ (716.961): C, 61.99; H, 9.56; N, 3.91. Found: C, 62.25; H, 9.62; N, 3.91.

FAB (M+H)+ at M/Z: 717.

IR (0.15% in CCl$_4$): 1739 (C=O) cm$^{-1}$.

$^1$HNMR (CDCl$_3$) delta 2.29 (s, N(CH$_3$)$_2$), 3.02 (t, 4″), 3.23 (dd, 2′), 3.31 (s, OCH$_3$), 3.50 (d, 11, J$_{10,11}$=10.5 Hz), 3.58 (dd, 9), 4.38 (d, 1′), 4.85 (d, 1″), 5.10 (dd, 13).

Method B

Step A (9S)-9-Deoxo-11,12-dideoxy-9,12-epoxy-11-iminoerythromycin A

The product from EXAMPLE 18, (9S)-9-deoxo-11,12-dideoxy-9,12-epoxy-11-hydroximinoerythromycin A (4.0 g, 5.4 mmol), was dissolved in 150 mL of methanol and the resultant solution was cooled in an ice bath. The flask was flushed with nitrogen and maintained under a positive nitrogen pressure. Concentrated ammonium hydroxide (30 mL) was added, followed by 20 mL (23.2 mmol) of titanium (III) chloride in ca. 25 wt. % hydrochloric acid, dropwise, over a 30 minute period. After stirring the reaction for 1 h at ambient temperature, the reaction mixture was blue but showed no substrate by HPLC. The reaction mixture was then diluted with 1.2 L of brine and 100 mL of concentrated ammonium hydroxide. The aqueous solution was extracted with 4×100 mL of chloroform. The combined organic layers were washed with a mixture of 40 mL of water, 50 mL of brine, and 10 mL of concentrated ammonium hydroxide, dried over anhydrous sodium sulfate, filtered, and evaporated in vacuo to yield 3.35 g (87% yield) of (9S)-9-deoxo-11,12-dideoxy-9,12-epoxy-11-iminoerythromycin A as a white glass.

Step B (9S,11S)-11-Amino-9-deoxo-11,12-dideoxy-9,12-epoxyerythromycin A

The product of STEP A, (9S)-9-deoxy11,12-dideoxy-9,12-epoxy-11-iminoerythromycin A, (3.13 g, 4.38 mmol) was dissolved in 100 mL of methanol and the resultant solution was cooled to −25° C. in a dry ice/CCl4 bath. Cerium (III) chloride heptahydrate (1.69 g, 4.5 mmol) was added, followed by 0.17 g (4.5 mmol) of sodium borohydride. After 0.5 h the reaction mixture was diluted with 600 mL of brine, 50 mL of concentrated ammonium hydroxide and 600 mL of water. The aqueous solution was extracted with 6×100 mL of chloroform. The combined organic layers were washed with a mixture of 100 mL of brine and 10 mL of concentrated ammonium hydroxide, dried over anhydrous sodium sulfate, filtered and concentrated in vacuo to give 3.01 g of the crude product, which was, according to HPLC analysis on a reverse phase $C_8$ column; 40% acetonitrile eluent; isocratic elution; flow rate=1 mL/min), 51.6% title compound. This crude product and 1.66 g of a previous run were treated under mild hydrolytic conditions to convert an interfering impurity to the 11-ketone. The crude product (4.67 g) was dissolved in acetonitrile/water (1:1 v/v) and 0.5 mL of glacial acetic acid was added to adjust the pH to 5.0. After 20 minutes the reaction mixture was poured into 1.0 L of 4% sodium bicarbonate and 20 mL of concentrated ammonium hydroxide was added. The resultant aqueous solution was extracted with 3×100 mL of chloroform. The combined chloroform layers were washed with 100 mL of 4% sodium bicarbonate, dried over anhydrous sodium sulfate, and concentrated in vacuo. The concentrate was dissolved in acetonitrile and reconcentrated to remove residual chloroform which yielded 4.52 g of white glass. The white glass was purified by chromatography on a silica gel column (2.9×62 cm) which had been washed with 30% methanol in acetonitrile containing 1% concentrated ammonium hydroxide and 500 mL of 1% concentrated ammonium hydroxide in acetonitrile. The column was also preconditioned with 4% methanol in acetonitrile, containing 0.1% concentrated ammonium hydroxide (the initial eluent). The column was run with a step gradient at 2.75 mL/min and fractions were collected every 8 min. The methanol concentration in the eluent was increased from 4% to 6% and finally 10%. The ammonium hydroxide concentration was increased from 0.1% to 0.4%. The title compound was obtained in 66% yield (2.07 g) from fractions 131-300, mp 168°-172° C. ($CH_3CN$).

FAB (M+H)+ at M/Z: 717 (716 961 calculated for $C_{37}H_{68}N_2O_{11}$).

IR (0.15% in $CCl_4$): 1738 (C=O) cm$^{-1}$.

The $^1$HNMR was identical to the product of METHOD A.

EXAMPLE 20

(4"R,9S,11S)-4",11-Diamino-9-deoxo-4",11,12-trideoxy-9,12-epoxyerythromycin A

Step A (9S,11S)-2'-O-Acetyl-9-deoxo-12-deoxy-9,12-epoxyerythromycin A

The product of EXAMPLE 4 (11.2 g, 15.6 mmol) was treated with 5.0 mL of acetic anhydride and 10.0 mL of triethylamine, as described in EXAMPLE 2, STEP B to yield 9.68 g (82% yield) of the tile compound.

FAB (M+H)+ at M/Z: 760 (759.984 calculated for $C_{39}H_{69}NO_{13}$).

$^1$HNMR (DCDl3) delta 2.08(s,COCH3), 2.26(s,N(CH3)2), 3.04 (t,4"), 3.32 (s OCH3), 3.67 (dd,9), 4.28 (dd,11), 4.49 (d,1'), 4.76 (dd,2'), 4.85 (d,1"), 5.09 (dd,13).

Step B (9S)-2'-O-Acetyl-9-deoxo-4",11,12-trideoxy-9,12-epoxy-4",11-dioxoerythromycin A A solution of potassium dichromate (24.5 g, 83.3 mmol) was prepared in 500 mL of water, to which concentrated (18M) sulfuric acid (18 mL, 337.6 mmol) was added at ambient temperature. A solution of (9S,11S)-2'-acetyl-9-deoxo-12-deoxy-9,12-epoxyerythromycin A (9.44 g, 12.4 mmol), from STEP A, was prepared in a mixture of 250 mL of methylene chloride ($CH_2Cl_2$) and 250 mL of dichloroethane ($CH_2ClCH_2Cl$) and added to the chromic acid solution. The reaction was carried out as described in EXAMPLE 2, STEP C, however, glacial acid was not added. The title compound was obtained as 8.81 g of crude material, which was taken on to the next step without purification.

Step C (4"E,9S)-9-Deoxo-4",11,12-trideoxy-9,12-epoxy-4"-hydroxyimino-11-oxoerythromycin A The product of STEP B was dissolved in 300 mL of methanol. In a separate 1 L round-bottom flask, a solution of hydroxylamine hydrochloride (4.03 g, 58 mmol) and 8.2 mL of triethylamine was prepared. The methanol solution of (9S)-2'-O-Acetyl-9-deoxo-4",11,12-trideoxy-9,12-epoxy-4",11-dioxoerythromycin A was added to the hydroxylamine solution at ambient temperature and the reaction mixture was heated to reflux. After 5.5 hours the reaction mixture was concentrated on a rotary evaporator to 30 mL and was diluted with 500 mL of 4% sodium bicarbonate and 3 mL of concentrated ammonium hydroxide. The resultant aqueous mixture was extracted with 1×200 mL and 2×75 mL portions of chloroform. The combined chloroform layers were washed with 100 mL brine, dried over anhydrous sodium sulfate, filtered and concentrated on a rotary evaporator to obtain 9.0 g of residue. The residue was dissolved in 75 mL of boiling methylene chloride and 200 mL of ethyl acetate was added. The solution was concentrated on a steam bath until crystallization started then left to stand at ambient temperature for 24 h. The crystals were filtered and air dried to yield 4.77 g (53%) of pure title compound, mp 252°-256° C.

Anal. calculated for $C_{37}H_{64}N_2O_{12}$(728.929): C, 60.97; H, 8.85; N, 3.84. Found: C, 60.87; H, 8.71; N, 3.55.

IR (0.15% in $CCl_4$): 1750 and 1729 (C=O) cm$^{-1}$.

¹HNMR (CDCl₃) delta 2.31 (s,N(CH₃)₂), 3.30 (dd,2'), 3.31 (s, OCH₃), 3.27 (dd,9), 4.46 (d,1'), 5.06 (m,2H,1",13), 5.17(q,5"), 8.50 (bs,NOH).

Step D (9S)-9-Deoxo-4",11,12-trideoxy-9,12-epoxy-4",11-di(-hydroxyimino)erythromycin A To a solution of triethylamine (1.2 mL, 8.57 mmole) in 10 mL of ethanol was added 858 mg (12.4 mmole) of hydroxylamine hydrochloride and 750 mg (1.03 mmole) of 11-oxo-9,12-oxy-9-deoxyerythromycin A 4"-oxime from step C. The mixture was stirred and heated to reflux in an oil bath. After 7 days at reflux the reaction mixture was diluted with 180 mL of brine and 10 mL of concentrated ammonium hydroxide. The product was extracted with 5×33 mL portions of CHCl₃. The combined CHCl₃ extracts were washed with 50 mL of 4% aqueous NaHCO₃, dried over Na₂SO₄, filtered and concentrated to give 739 mg of a white glass. The product was purified by chromatography on 100 g. of silica gel (2.4×44 cm) by elution with a mixture of chloroform, acetonitrile, methanol and concentrated ammonium hydroxide (75:20:5:0.2 v/v/v/v). The fractions containing the product, as a 4 to 1 mixture of two oxime isomers, were combined and the solvents removed with a rotary evaporator to yield 405 mg (53%) of a white solid.

FAB (M+H)+ at M/Z: 744 (743.944 calculated for $C_{37}H_{65}N_3O_{12}$).

¹HNMR (CDCl₃) major isomer, delta 2.31 (s, N(CH₃)₂), 3 26 (dd, 2'). 3.31 (s OCH₃), 3 83 (dd, 9), 4.43 (d, 1'), 4.99 (dd, 1"), 5.13 (q, 5"), 5.23 (dd, 13), 7.83 (bs, NOH).

Step E

4"R,9S,11S)-4",11-Diamino-9-deoxo-4",11,12-trideoxy-9,12-epoxyerythromycin A (9S)-9 Deoxo-4",11,12-trideoxy-9,12-epoxy-4",11-di(-hydroxyimino)erythromycin A (373 mg, 0.50 mmole), the product of Step D, was dissolved in 54 mL of methanol. Then, 6 mL of concentrated ammonium hydroxide and 3.0 g of Raney nickel were added. The reaction mixture was put on a Parr shaker at 4 atm. of hydrogen for 4 days. The reaction mixture was filtered and the filter cake washed with methanol. The combined methanol filtrates were concentrated on a rotary evaporator and the residue dissolved in a small volume of acetonitrile. The acetonitrile mixture was filtered (0.45 u, nylon) and the solvent evaporated to provide 253 mg of the crude product as a mixture of 4" and 11 amino epimers. The desired isomer was isolated by reverse phase HPLC using a YMC, Inc. C₈ column (20×250 mm) eluted with a mixture of water, acetonitrile, and methanol (14:5:1 v/v/v) containing 30 g/L sodium acetate and 1.5 mL/L glacial acetic acid at a flow rate of 12 mL/min. The product was recovered from fractions, eluted between 8 and 9 minutes after injection, providing 13.4 mg of a white solid.

FAB (M+H)+ at M/Z: 716 (715.977 calculated for $C_{37}H_{69}N_3O_{10}$).

¹HNMR (CDCl₃) delta 2.31 (s, N(CH₃)₂), 3.25 (dd,2'), 3.32 (s, OCH₃), 3.50 (d,11,J₁₀,₁₁=10.5 Hz), 3.57 (dd, 9), 4.45 (d, 1'), 4.61 (dq,5", J₄",5"'=1.2 Hz), 4.89 (d, 1"), 5.10 (dd, 13).

EXAMPLE 21

(4"R,9S)-9-Deoxo-11,12-dideoxy-9,12-epoxy-11-oxo-erythromycin A

A 700 mg sample of (9S)-2'-O-acetyl-9-deoxo-4",11,12-trideoxy-9,12-epoxy-4",11-dioxoerythromycin A (from Example 20, Step B), was dissolved in a mixture of 50 mL of isopropyl alcohol and 50 mL of ethyl acetate. Then, 1.2 g of Raney nickel was added and the mixture was put on a Parr shaker under 4 atm. of hydrogen at ambient temperature for 18 hours. The reaction mixture was filtered and the filter washed with ethylacetate. The solvents were removed using a rotary evaporator. The residue was dissolved in 200 mL of acetonitrile, filtered (0.45 u, nylon), and then concentrated to dryness in vacuo. The 2'-acetate was cleaved in methanol (100 mL) on standing at ambient temperature for two days. The methanol was removed and the residue was chromatographed on 100 g. of silica gel, eluting with acetonitrile: concentrated ammonium hydroxide (10:0.07 v/v), to provide 284 mg (40% yield) of the title compound, mp. 165°–168° C. (CH₃CN).

Anal. calculated for $C_{37}H_{65}NO_{12}$ (715.930): C, 62.07; H, 9.15; N, 1.96. Found: C, 61.53; H, 9.01; N, 1.93.

¹HNMR (CDCl₃) delta 2.31 (s, N(CH₃)₂), 3.08 (bd, 4"), 3.28 (s, OCH₃), 3.32 (dd,2'), 3.78 (dd,9), 4.40 (d,1"), 4.64 (dq, 5", J₄", 5"=1.0 Hz), 4.87 (d,1'), 5.14 (dd,13).

EXAMPLE 22

(4"S,9S,11S)-4",11-Diamino-9-deoxo-4",11,12-trideoxy-9,12-epoxyerythromycin A

Step A (4"S,9S)-4"-Amino-9-deoxo-4",11,12-trideoxy-9,12-epoxy-11-hydroxyiminoerythromycin A The product of EXAMPLE 14, STEP D, (4"S,9S)-4"-amino-9-deoxo-4"11,12-trideoxy-9,12-epoxy-11-oxo-erythromycin A, (9.29 g, 13 mmol) was treated with hydroxylamine hydrochloride (19.5 g, 280 mmol) and triethylamine (36 mL) as described in EXAMPLE 18. The crude product (10.51 g), as a mixture of Z and E oxime isomers, was purified on a silica gel column. The column was packed in acetonitrile: 0.6% concentrated ammonium hydroxide. The column was eluted with a step gradient of ammonium hydroxide from 0.2% in acetonitrile in the initial 2.8 L of eluent to 0.6% in the second 2.8 L of eluent to 0.8% in the third 2.8 L of eluent to a final value of 1% in the last fractions collected. Fractions were combined based on tlc analytical data, providing 5.60 g of a mixture of Z and E oxime isomers. A small portion of the early eluting material was crystallized from acetonitrile and provided the pure Z-oxime, m.p. 239°–242° C.

Anal. calculated for $C_{37}H_{67}N_3O_{11}$ (729.960): C, 60.88; H, 9.25; N, 5.76. Found: C, 60.92; H, 9.32; N, 6.00.

FAB (M+H)+ at M/Z: 730.

IR (0.15% in CCl₄) v 3595 (NOH) and 1738 cm⁻¹ (Lactone)

1HNMR(CDCl₃) delta 2.31 (s, N(CH₃)₂), 3.29 (s, OCH₃), 3.35 (dd, 2'), 3.55 (dd, 9), 4.03 (dq, 5", J₄", 5"=10 Hz), 4.58 (d, 1'), 4.73 (d, 1"), 4.93 (dd, 13), 8.26 (bs, NOH).

Rechromatography of latter eluting material afforded the pure E-oxime.

FAB (M+H)+ at M/Z: 730 (729.960 calculated for $C_{37}H_{67}N_3O_{11}$).

IR (0.15% in CCl₄) v 3595 (NOH) and 1738 cm⁻¹ (lactone).

¹HNMR(CDCl₃) delta 2.32 (s, N(CH₃)₂), 3.25 (s, OCH₃), 3.28 (dd, 2'), 3.81 (dd, 9), 4.03 (dq, 5", J₄", 5"=10 Hz), 4.39 (d, 1'), 4.83 (d, 1"), 5.21 (dd, 13), 6.98 (bs, NOH).

Step B (4"S,9S)-4"-Amino-9-deoxo-4",11,12-trideoxy-9,12-epoxy-11-iminoerythromycin A The product of STEP A (5.31 g, 7.28 mmol) was treated with titanium (III) chloride as described in EXAMPLE 19, METHOD B, STEP A. The title compound was obtained in 96% yield (4.97 g) and carried on to the next step without purification.

Step C (4"S,9S,11S)-4",11-Diamino-9-deoxo-4",11,12-trideoxy-9,12-epoxyerythromycin A The product of STEP B (4.97 g, 7.0 mmol) was treated with sodium borohydride (0.51 g) and cerium (III) chloride heptahydrate (3.52 g) as described in EXAMPLE 19, METHOD B, STEP B. The crude product (4.54 g) was purified on a silica gel column (4.4×42 cm). The column was packed in acetonitrile: 5% ammonium hydroxide and equilibrated (1.25 L) with chloroform/acetonitrile/methanol/ammonium hydroxide (10:2.5:0.15:0.02 v/v/v/v). The pH of the eluate was 9. The concentrations of methanol and ammonia were increased in steps during the elution. The initial 2.8 L of eluting solvent was the same as the equilibrating solvent. In the second 2.8 L the solvent proportions were 10:2.5:0.2:0.2 and in the third 2.8 L the solvent proportions were 10:2.5:0.3:0.03. In the final fractions the solvent proportions were 10:3.0:0.5:0.05. The fractions containing (4"S,9S,11S)-4",11-diamino-9-deoxo-4",11,12-trideoxy-9,12-epoxyerythromycin A were combined and concentrated in vacuo. The title compound was obtained pure in 56% yield (2.8 g)

Anal. calculated for C₃₇H₆₉N₃O₁₀(715.977): C, 62.07; H,9.71; N, 5.87. Found: C, 61.76; H, 9.72; N, 5.73

IR ((0.15% in CCl₄): 3480 (N—H), 1736 (C=O) cm⁻¹.

FAB (M+H)⁺ at M/Z: 716.

¹HNMR(CDCl₃) delta 2.29 (s, N(CH₃)₂), 3.22 (dd, 2'), 3.28 (s, OCH₃), 3.50 (d, 11, J₁₀,₁₁=10 Hz), 4.01 (dq, 5",J₄",₅"=10 Hz), 4.40 (d, 1'), 4.87 (d, 1"), 5.10 (dd, 13).

EXAMPLE 23

(9S,11S)-4"-O-Acetyl-9-deoxo-12-deoxy-9,12-epoxyerythromycin A

Step A (9S,11S)-2',4"-O-Diacetyl-9-deoxo-12-deoxy-9,12-epoxy-11-O-trimethylsilylerythromycin A To a stirred solution of (9S,11S)-2'-O-acetyl-9-deoxo-12-deoxy-9,12-epoxy-11-O-trimethylsilylerythromycin A (0.60 g, 0.72 mmol), the product of Example 17, Step B, in 4 mL of CH₂Cl₂ was added 0.12 g (0.98 mmol) of 4-dimethylaminopyridine and 0.42 mL (4.39 mmol) of acetic anhydride. After 40 min. the reaction mixture was diluted with 100 mL of benzene, washed with 5% NaHCO₃ and concentrated to dryness with a rotary evaporator to provide 370 mg (62% yield) of the title compound.

¹HNMR(CDCl₃) delta 0.17 (s, Si(CH₃)3), 2.08 (s, COCH₃), 2.13 (s, COCH₃), 2.31 (s, N(CH₃)₂), 3.32 (s, OCH₃), 3.65 (dd, 9), 4.20 (d, 11), 4.56 (d, 1'), 4.70 (d, 4"), 4.81 (dd, 2'), 4.91 (d, 1"), 5.05 (dd, 13).

Step B (9S,11S)-4"-O-Acetyl-9-deoxo-12-deoxy-9,12-epoxyerythromycin A

The product of STEP A (0.37 g, 0.45 mmol) was dissolved in a mixture of 50mL of methanol and 1 mL of triethylamine and heated to 50° for 18 hours. The solvents were removed and then the residue was dissolved in 50 mL of benzene. The benzene layer was washed with 5% NaHCO₃ and then with brine. The benzene was removed to provide 0.25 g of residue. This residue was converted to the title compound with tetra-n butylammonium fluoride as described in EXAMPLE 17, STEP E. After purification, (9S,11S)-4"-O-acetyl-9-deoxo-12-deoxy-9,12-epoxyerythromycin A was obtained in 28% Yield (0.1 g).

Anal. calculated for C₃₉H₆₉NO₁₃H₂O (777.999): C, 60.21; H, 9.20; N, 1.80. Found: C, 60.69; H, 9.05; N, 1.77.

FAB (M+H)⁺ at M/Z: 760 (759.984 calculated for C₃₉H₆₉NO₁₃).

IR bands (0.15% in CCl₄) v 3480 (O—H), 1720 (C=O) cm⁻¹.

¹HNMR(CDCl₃) delta 2.13 (s, COCH₃), 2.30 (s, N(CH₃)₂), 3.21 (dd, 2'), 3.33 (s, OCH₃), 3.66 (dd, 9), 4.28 (dd, 11), 4.46 (d, 1'), 4.71 (d, 4"), 4.89 (d, 1"), 5.08 (dd, 13).

EXAMPLE 24

(9S)-4"-Deoxo-4",11,12-trideoxy-9,12-epoxy-4"-methylamino-11-oxoerythromycin

Step A (9S)-4"-Amino-9-deoxo-4",11,12-trideoxy-9,12-epoxy-11-oxoerythromycin A The product from EXAMPLE 20, STEP C, (9S)-9-deoxo-4",11,12-trideoxy-9,12-epoxy-4"-hydroxyimino-11-oxoerythromycin A, (0.62 g, 0.85 mmol) was reduced with Raney nickel (1.0 g) in methanol as described in EXAMPLE 14, STEP A. The title compound, an isomeric mixture of the products of EXAMPLES 8 and 14, was obtained in 90% yield and taken on to the next step.

Step B (9S)-9-Deoxo-4",11,12-trideoxy-9,12-epoxy-4"-dimethylamino-11-oxoerythromycin A The product of STEP A (0.55 g, 0.77 mmol) was treated with sodium cyanoborohydride (0.19 g, 3.1 mmol) as described in EXAMPLE 12, using 37% formalin (0.58 mL, 7.74 mmol) instead of benzaldehyde and acetic acid (0.09 mL) instead of hydrochloric acid. The title compounds were obtained and purified as a mixture of isomers. The purification was carried out on a silica gel column which was pretreated and eluted with 0.2% ammonium hydroxide in acetonitrile. The column flow rate was 2.5 mL/min. The fractions containing the desired products were combined and concentrated in vacuo to yield 0.292 g (51% yield) of the title compound as an isomeric mixture of EXAMPLES 29C and 30B (see Table 1), as a white glass.

Step C

(9S)-9-Deoxo-4",11,12-trideoxy-9,12-epoxy-4"-methylamino-11-oxoerythromycin A The products of STEP B (0.227 g 0.305 mmol) were treated with acetic anhydride (0.64 mmol) and triethyl amine (0.1 mL) in methylene chloride as described in EXAMPLE 1, STEP A. The 2'-O-acetyl compound was obtained in 98% crude yield (0.234 g) and transferred to a 100 mL round-bottom flask and cooled in an ice/water bath. In a separate flask, 12.5 mL of methanol was cooled in an ice/water bath. Sodium acetate trihydrate (0.22 g, 1.617 mmol) was dissolved in the methanol followed by 0.078 g (0.307 mmol) solid iodine. When all the iodine had dissolved, the methanol solution was added to the flask containing the (9S)-2'-O-acetyl-9-deoxo-4",11,12-trideoxy-9,12-epoxy-4"-dimethylamino-11-oxoerythromycin A. The reaction mixture was illuminated with a 150 watt flood lamp. After 2 h, 0.1 g of sodium thiosulfate was added to decompose the excess iodine. The clear white solution was allowed to stand at ambient temperature for approximately 64 h. The methanol was evaporated in vacuo and the residue was dissolved in 80 mL of benzene. The benzene solution was washed with 3×35 mL of brine containing 1% concentrated ammonium hydroxide, dried over anhydrous sodium sulfate, filtered and evaporated to give 0.166 g (79% yield) of the title compounds, as an isomeric mixture. The isomers were separated by semi-preparative scale HPLC on a reverse phase $C_8$ column (20×250 mm); eluent: 45% acetonitrile, 5% methanol in water containing 30 g/L sodium acetate trihydrate and 1.5 mL/L glacial acetic acid; isocratic elution; flow rate=12 mL/min. Seven 0.4 mL injections were made of the product in methanol solution (0.055 g/mL). The fractions containing each product were separately pooled and concentrated in vacuo to remove the organic solvents. The concentrated aqueous solutions were made basic (pH 10.5) with 7% sodium carbonate solution and extracted with 3×20 mL of chloroform. Both of the combined chloroform layers were washed with brine containing 1% concentrated ammonium hydroxide and concentrated in vacuo. The residues were separately dissolved in acetonitrile, treated with anhydrous sodium carbonate, filtered, and the solvents were removed on a rotary evaporator.

A first isomeric product (4"R,9S)-9-deoxo-4",11,12-trideoxy-9,12-epoxy-4"-methylamino-11-oxoerythromycin A was obtained in 36% yield (0.075 g).

Anal calculated for $C_{38}H_{68}N_2O_{11}$ (728.972): C, 62.61; H, 9.40; N, 3.84. Found: C, 62.43; H, 9.42; N, 3.85.

FAB $(M+H)^+$ at M/Z: 729.

IR (0.15% in $CCl_4$): 1755 and 1738 (C=O) $cm^{-1}$.

$^1$HNMR($CDCl_3$) delta 2.31 (s, $N(CH_3)_2$), 2.52 (s, $NCH_3$), 3.27 (s, $OCH_3$), 3.35 (dd, 2'), 3.77 (dd, 9), 4.40 (d, 1'), 4.72 (dq, 5", $J_{4",5"}$=1.5 Hz), 4.78 (d, 1"), 5.15 (dd, 13).

A second isomeric product (4"S,9S)-9-deoxo-4",11,12-trideoxy-9,12-epoxy-4"-methylamino-11-oxoerythromycin A was obtained in 18% yield (0.0384 g).

Anal. calculated for $C_{38}H_{68}N_2O_{11}$ (728.972): C, 62.61; H, 9.40; N, 3.84. Found: C, 62.48; H, 9.63; N, 3.78.

FAB $(M+H)^+$ at M/Z: 729.

IR (0.15% in $CCl_4$) 1755 and 1738 (C=O) $cm^{-1}$.

$^1$HNMR($CDCl_3$) delta 2.31 (s, $N(CH_3)_2$), 2.53 (s, $NCH_3$), 3.23 (s, $OCH_3$), 3.32 (dd, 2'), 3.77 (dd, 9), 4.04 (dq, 5", $J_{4",5"}$=10 Hz), 4.40 (d, 1"), 4.81 (d, 1"), 5.13 (dd, 13).

EXAMPLE 25

(9S,11S)-2'-O-Acetyl-9-deoxo-12-deoxy-9,12-epoxy-11-O-triethylsilyl-4"-O-(2-oxoethyl)erythromycin A

Step A

(9S,11S)-2'-O-Acetyl-9-deoxo-12-deoxy-9,12-epoxy-11-O-triethylsilyl-4"-O-[(phenylmethoxy)carbonyl]erythromycin A The product from EXAMPLE 5, METHOD B, Step A, (9S,11S)-2'-O-acetyl-9-deoxo-12-deoxy-9,12-epoxy-4"-O-[(phenyl methoxy)carbonyl]erythromycin A, (0.65 g, 0.73 mmol) was treated with triethylsilyl chloride (0.6 mL, 4.38 mmol) in 4 mL of chloroform by the procedure described in EXAMPLE 17, Step A. The title compound was obtained (0.62 g) in 84% yield.

FAB $(M+H)^+$ at M/Z: 1008 (1008.383 calculated for $C_{53}H_{89}NO_{15}Si$).

$^1$HNMR ($CDCl_3$) delta 0.65 (q, $Si(C_2H_5)_3$), 1.00 (t, $Si(C_2H_5)_3$), 2.04 (s, $COCH_3$), 2.25 (s, $N(CH_3)_2$), 3.32 (s, $OCH_3$), 3.64 (dd,9), 4.28 (d, 11), 4.48 (d, 4"), 4.52 (d,1'), 4.75 (dd,2'), 4.90 (d,1"), 5.07 (dd,13), 5.13 (d, benzylic H), 5.25 (d, benzylic H), 7.36 (m, $C_6H_5$).

Step B

(9S,11S)-2'-O-Acetyl-9-deoxo-12-deoxy-9,12-epoxy-11-O-triethylsilylerythromycin A The product of Step A (0.62 g, 0.61 mmol) was catalytically hydrogenated in ethylacetate using 0.3 g of 10% palladium on carbon as catalyst, as described in EXAMPLE 3, METHOD A. The title compound was obtained (0.43g) in 80% yield.

FAB $(M+H)^+$ at M/Z: 874 (874.248 calculated for $C_{45}H_{83}NO_{13}Si$).

$^1$HNMR ($CDCl_3$) delta 0.65 (q, $Si(C_2H_3)_3$), 1.00 (t, $Si(C_2H_5)_3$), 2.07 (s, $COCH_3$), 2.25 (s, $N(CH_3)_2$), 3.03 (dd,4"), 3.31 (s, $OCH_3$), 3.63 (dd, 9), 4.28 (d, 11), 4.48 (d,1'), 4.76 (dd,2'), 4.83 (d,1"), 5.07 (dd,13).

Step C

(9S,11S)-2'-O-Acetyl-9-deoxo-12-deoxy-9,12-epoxy-11-O-triethylsilyl-4"-O-(2-propenyl)erythromycin A The product of Step B (1.24 g, 1.41 mmol) was dissolved in 13 mL of dimethyl formamide (DMF). This solution was cooled to −50° C. and 3 mL of 1 M sodium bis(trimethylsilyl) amide were added, followed by 0.25 mL (2.8 mmol) of allyl bromide. The reaction mixture was stirred for one hour at 50° C. and quenched with 3 mL of brine. The solvent was removed in vacuo and the residue was partitioned between chloroform and brine. The chloroform layer was evaporated and the oil was purified on a silica gel column; the eluent was 5% methanol in chloroform. The title compound was obtained (0.97 g) in 75% yield.

FAB $(M+H)^+$ at M/Z: 914 (914.303 calculated for $C_{48}H_{87}NO_{13}Si$)

$^1$HNMR ($CDCl_3$) delta 0.65 (q, Si $C_2H_5)_3$), 1.00 (t, $Si(C_2H_5)_3$), 2.04 (s, $COCH_3$), 2.26 (s, $N(CH_3)_2$), 2.87 (d, 4"), 3.33 (s, $OCH_3$), 3.64 (dd, 9), 4.13 (m, allylic $CH_2$), 4.30 (d, 11), 4.53 (d, 1'), 4.75 (dd, 2'), 4.83 (d, 1"), 5.07 (dd, 13), 5.20 (m, C=$CH_2$), 5.95 (m, CH=C).

Step D

(9S,11S)-2'-O-Acetyl-9-deoxo-12-deoxy-9,12-epoxy-11-O-triethylsilyl-4"-O-(2-oxoethyl)erythromycin A The product of Step C (0.49 g, 0.6 mmol) was dissolved in 12 mL of 20% water in THF at ambient temperature, and methylmorpholine N-oxide (15 g, 1.5 mmol) was added, followed by 1.3 mL (0.06 mmol) of 2.5 wt % osmium tetroxide in t-butyl alcohol. The reaction mixture was stirred for 3 h at ambient temperature then quenched with 5% sodium hydrogen sulfite on celite and filtered. The solvent was removed in vacuo and the residue purified on a silica gel column with 10% methanol in chloroform containing 1% concentrated ammonium hydroxide. The dihydroxy intermediate was obtained (0.4 g) in 79% yield.

The dihydroxy intermediate (0.4 g, 0.47 mmol) was dissolved in 20% water in THF at 0° C. Sodium metaperiodate (0.5 g, 2.3 mmol) was added and the reaction mixture was stirred for 2.5 h at 0° C. and filtered through 2.5 q of silica gel with 10% methanol in chloroform. The solvents were removed in vacuo and the resultant oil was purified on silica gel eluted with 10% methanol in chloroform. The title compound was obtained (0.37 g) in 97% yield.

FAB (M+H)+ at M/Z: 916 (higher mass peaks also seen, 916.285 calculated for $C_{47}H_{85}NO_{14}Si$).

$^1$HNMR (CDCl$_3$) delta 0.65 (q, S C$_2$H$_5$)$_3$), 1.00 (t, Si(C$_2$H$_5$)$_3$), 2.05 (s, COCH$_3$), 2.27 (s, N(CH$_3$)$_2$), 2.93 (d, 4"), 3.36 (s, OCH$_3$), 3.64 (dd, 9), 4.25 (d, OCH$_2$C), 4.29 (d, 11), 4.52 (d, 1'), 4.77 (dd, 2'), 4.83 (d, 1"), 5.08 (dd, 13), 9.80 (t, CHO).

EXAMPLE 26

Following the synthesis outlined in EXAMPLE 12, using the product of EXAMPLE 25 and the appropriate amine, followed by the removal of the acetyl and silyl protecting groups as described in EXAMPLE 17, EXAMPLES 26A, 26B, 26C and 26D were made as disclosed in Table 1. The structure of each was confirmed by $^1$H-NMR, elemental analysis and/or mass spectra as designated.

EXAMPLE 27

9,10-Dihehydro-9-deoxo-11,12-dideoxy-9,12-epoxy-6-O-methyl-11-oxoerythromycin A

Step A

2'-O-Acetyl-6-O-methylerythromycin A

An acetyl protecting group was added to the amino sugar of 6-O-Methylerythromycin A with acetic anhydride and triethylamine in methylene chloride as described in EXAMPLE 1, Step 1. The title compound was then taken on to the next step.

Step B

2'-O-Acetyl-6-O-methyl-4"-O-[(phenylmethoxy)carbonyl]erythromycin A

A benzyloxycarbonyl protecting group was attached to the product of Step A with benzyloxycarbonyl chloride, as described in EXAMPLE 1, Step 2. The title compound was obtained and taken on to the next step.

Step C

2'-O-Acetyl-11-deoxy-6-O-methyl-11-oxo-4"-O-[(phenylmethoxy)carbonyl]erythromycin A Oxalyl chloride (5.0 mL, 57.5 mmol) was dissolved in 50 mL of methylene chloride in a dry flask under a nitrogen atmosphere. This solution was cooled to −70° C. in a dry ice/acetone bath and 6.9 mL (88.3 mmol) of dimethyl sulfoxide (DMSO) in 5 mL of methylene chloride was added over a 5 minute period. The solution was allowed to stir for 6 min and a solution of 5 g (5.41 mmol) of 2'-O-acetyl 6-O-methyl-4"-O-[(phenylmethoxy)carbonyl]erythromycin A, from Step B, in 20 mL of methylene chloride was added by syringe, over a 5 min period. The reaction mixture was stirred at −70° C. for 65 min and 26 mL of triethylamine was added slowly. The reaction mixture was warmed to ambient temperature and it was diluted with 500 mL of methylene chloride. The diluted methylene chloride solution was washed with 3×250 mL of 6% phosphate buffer, followed by 3×250 mL of 4% sodium bicarbonate solution and 250 mL of brine, dried over anhydrous sodium sulfate, filtered and concentrated on a rotary evaporator. The residue (5.14 g) was purified on a silica gel (120 g) column (2.5×60 cm) under positive pressure (flash chromatography) of air (11 psi). The column was eluted with 1.5 L of CH$_2$Cl$_2$:CH$_3$OH:NH$_4$OH (98:2.0:0.2). The fractions containing the title compound were pooled and concentrated to give 3.21 g (64% yield) of pure 2'-O-Acetyl-11-deoxy-6-O-methyl-11-oxo-4"-O-[(phenylmethoxy)carbonyl]erythromycin A which existed predominantly as the 9,12 hemiacetal.

FAB (M+H)+ at M/Z: 922 (922.130 calculated for $C_{48}H_{75}NO_{16}$).

$^1$HNMR (CDCl$_3$, major isomer) delta 2.06 (s, COCH$_3$), 2.26 (s, N(CH$_3$)$_2$), 3.25 (s, OCH$_3$), 3.29 (s, OCH$_3$), 4.48 (m, 4", 5"), 4.52 (d, 1'), 4.75 (dd, 2'), 4.85 (d, 1"), 5.13 (dd, 13), 5.20 (s, benzylic CH$_2$), 7.36 (m, C$_6$H$_5$).

Step D

9,10-Didehydro-9-deoxo-11,12-dideoxy-9,12-epoxy-6 0-methyl-11-oxoerythromycin A The product of Step C (3.21 g, 3.46 mmol) was dissolved in a solution of 36 mL ammonia and 60 mL of methanol in a bomb. 20% Palladium on carbon (1.6 g) was added and the reaction was carried out under 500 psi hydrogen at 60° C. for 3 h. The reaction mixture was allowed to cool overnight in the sealed reaction bomb then filtered by gravity under argon. It was refiltered through a nylon membrane filter to remove any traces of catalyst. The solvent was removed in vacuo and the residue redissolved in 125 mL of methanol. The solution was allowed to stir overnight in an oil bath at 50° C. The methanol was removed in vacuo. The residue (2.56 g) was purified on a silica gel (250 g) column (5×30 cm). The column was run under 11 psi of air and eluted with 1 L of CH$_2$Cl$_2$:CH$_3$OH:NH$_4$OH (9.8:0.2:0.02), followed by 1 L of CH$_2$Cl$_2$:CH$_3$OH:NH$_4$OH (9.7:0.3:0.03). The fractions containing the title compound were combined and concentrated in vacuo to give 2.22 g (88% yield) of pure 9,10-didehydro-9-deoxo-11,12-dideoxy-9,12-epoxy-6-O-methyl-11-oxoerythromycin A.

FAB (M+H)+ at M/Z: 728 (727.941 calculated for $C_{38}H_{65}NO_{12}$).

¹HNMR (CDCl₃) delta 1.77 (s, 10 CH₃), 2.30 (s, N(CH₃)₂), 3.01 (t, 4"), 3.19 (dd, 2'), 3.21 (s, 3"OCH₃), 4.37 (d, 1'), 4.86 (d, 1"), 5.26 (dd, 13).

EXAMPLE 28

Following the synthesis described in EXAMPLE 13, Step A, the product of EXAMPLE 27 was reduced with lithium borohydride (LiBH₄) to obtain EXAMPLE 28A as disclosed in Table 1.

Following the synthesis described in EXAMPLE 7, Step C, the product of EXAMPLE 27 was reduced with diisobutyl aluminum hydride (DIBAH) to obtain EXAMPLE 28B as disclosed in Table 1.

The structure of each was confirmed by ¹H NMR, elemental analysis and/or mass spectra as indicated in Table 1.

EXAMPLE 29

Following the synthesis outlined in EXAMPLE 12 using the product of EXAMPLE 14 as the amine, the appropriate aldehyde and sodium cyanoborohydride (NaCNBH₃) as the reducing agent, and in the case of Example 29A, subsequent treatment with hydrogen and formaldehyde in the presence of an appropriate catalyst, Examples 29A, 29B and 29C were obtained as disclosed in Table 1.

Following the synthesis outlined in EXAMPLE 14, using the product of EXAMPLE 14 as the amine starting material, the appropriate aldehyde and palladium on carbon (Pd/C) as the reduction catalyst, EXAMPLE 29D was obtained as disclosed in Table 1.

Following the synthesis outlined in EXAMPLE 9, using the product of EXAMPLE 14 as the starting material and the appropriate reagents, EXAMPLE 29E was obtained as disclosed in Table 1.

Following the synthesis outlined in EXAMPLE 10, using the product of EXAMPLE 14 as the starting material and the appropriate reagents EXAMPLE 29F was obtained as disclosed in Table 1.

The structure of each of the above examples was confirmed by ¹H-NMR, elemental analysis and/or mass spectra as indicated in Table 1 below. It should be understood that $R_1$, $R_2$, and $R_3$ as used herein correspond to the R groups identified by Formula I.

EXAMPLE 30

Following the synthesis outlined in EXAMPLE 12 using the product of EXAMPLE 8 as the amine, the appropriate aldehyde and reducing agent, and in the case of Example 30A, subsequent treatment with hydrogen and formaldehyde in the presence of an appropriate catalyst, EXAMPLES 30A and 30B were obtained as disclosed in Table 1.

Following the synthesis described in EXAMPLE 14 and using the product of EXAMPLE 8 as the amine starting material, the appropriate aldehyde and the appropriate hydrogenation catalyst, EXAMPLE 30C disclosed in Table 1, was obtained.

The structure of each was confirmed by ¹H-NMR, elemental analysis and/or mass spectra as indicated in Table 1.

EXAMPLE 31

(9S)-4"-O-Aminocarbonyl-9-deoxo-11,12-dideoxy-9,12-epoxy-11-oxoerythromycin A

The title compound was prepared from the product of Example 5, as the 2'-O-acetyl derivative, according to the procedures given in Example 17, Steps C and D.

FAB (M+H)+ at M/Z: 759 (758.955 calculated for $C_{38}H_{66}N_2O_{13}$).

NMR (CDCl₃) delta 3.30 (dd, 2'), 3.79 (dd, 9), 4.38 (d, 1'), 4.56 (d, 4"), 4.87 (d, 1"), 5.14 (dd, 13)

EXAMPLE 32

(4"S,9S)-4"-[(aminocarbonyl)amino]-9-deoxo-4",11,12-trideoxy-9,12-epoxy-11-oxoerythromycin A The title compound was prepared from the product of Example 14, as the 2'-O-acetyl derivative, following the procedures given in Example 17, Steps C and D.

FAB (M+H)+ at M/Z: 758 (757.971 calculated for $C_{38}H_{67}N_3O_{12}$).

¹H NMR (CDCl₃) delta 3.37 (dd, 2'), 3.79 (dd, 9), 4.26 (bd, 4"), 4.31 (d, 1'), 4.89 (d, 1"), 5.13 (dd, 13).

EXAMPLE 33

(9S,11S)-11-Amino-9-deoxo-4",11,12-trideoxy-9,12-epoxyerythromycin A

Step A (9S,11S)-11-(N-Benzyloxycarbonyl)amino-9-deoxo-11,12-dideoxy-9,12-epoxyerythromycin A The product of EXAMPLE 19, (9S,11S)-11-amino-9-deoxo-11,12 dideoxy-9,12-epoxyerythromycin A (8g, 11.17 mmol), was dissolved in 161 mL of methylene chloride; 2.8 g (11.24 mmol) of benzyloxycarbonyl N-hydroxysuccinimide was added and the reaction mixture stirred overnight at ambient temperature. The reaction mixture was then transferred to a separatory funnel and washed with 300 mL of 5% aqueous sodium bicarbonate solution. The aqueous layer was back-extracted with 3×100 mL of methylene chloride and the organic layers combined. The combined organic layers were dried over anhydrous sodium sulfate and concentrated under reduced pressure to give 10.43 g of the title compound. The product was taken on to the next step without purification.

Step B (9S,11S)-2'-O-Acetyl-11-(N-benzyloxycarbonyl)amino-9-deoxo-11,12-dideoxy-9,12-epoxyerythromycin A To a solution of 10.43 g of (9S,11S) 11-(N-benzyloxycarbonyl)amino 9 deoxo-11,12-dideoxy-9,12-epoxyerythromycin A, from Step A, in 104 mL of methylene chloride, at ambient temperature, was added 5.21 g (37.7 mmol) of potassium carbonate and 2.76 mL (29.2 mmol) of acetic anhydride and the reaction mixture stirred at ambient temperature overnight. The reaction mixture was transferred to a separatory funnel and washed with 50 mL of 5% aqueous sodium bicarbonate. The aqueous layer was back-extracted with 3×100 mL of methylene chloride and the organic layers were combined. The combined organic layers were washed with brine, dried over anhydrous sodium sulfate, filtered and concentrated under reduced pressure to give 8.65 g of the title compound. The product was carried on to the next step without purification.

Step C (9S,11S)-2'-O-Acetyl-11-(N-benzyloxycarbonyl)amino-9-deoxo-11,12-dideoxy 9,12 epoxy-4"-O-(1'-H-1'-imidazole)thiocarbonylerythromycin A A solution of 6.86 g of (9S,11S)-2'-O-acetyl-11-(N-benzyloxycarbonyl)amino-9-deoxo-11,12-dideoxy-9,12-epoxyerythromycin A, from Step B, in 16 mL of methylene chloride was prepared in an oven dried flask. To this solution was added 3.75 g (30.7 mmol) of N,N-dimethyl-4-aminopyridine, followed by 3.5 g (19.6 mmol) of 1,1'-thiocarbonyl-bis-1-H-imidazole. The reaction mixture was stirred at ambient temperature for 24 hours, diluted with 200 mL of methylene chloride and washed with pH 5 phosphate buffer solution. The organic layer was separated and washed with 5% aqueous sodium bicarbonate solution. The combined aqueous layers were back-washed with 2×50 mL of methylene chloride. The combined organic layers were washed with brine, dried over anhydrous sodium sulfate, filtered and concentrated under reduced pressure. The residue (a yellow glass) was purified by chromatography on silica gel eluted with chloroform:acetonitrile (1:1) to give 3.19 g (28.5% yield from (9S,11S)-11-amino-9-deoxo-11,12-dideoxy-9,12-epoxyerythromycin A) of the title compound. MS DCI-NH$_3$ M/Z: 1004 (M+H)$^+$; $^1$H NMR (CDCl$_3$) delta 0.84 (t, 3H, 15), 2.13 (s, 3H, COCH$_3$), 2.29 (s, 6H, NMe$_2$), 3.38 (s, 3H, OCH$_3$), 3.42 (m, 1H, 5'), 3.50 (d, 1H, 5), 3.59 (dd, 1H, 9), 7.06 (dd, 1H, Im), 7.30–7.40 (m, 5H, Ph), 7.63 (m, 1H, Im), 8.33 (d, 1H, Im).

Step D (9S,11S)-2'-O-Acetyl-11-(N-benzyloxycarbonyl)amino-9-deoxo-4",11,12-trideoxy-9,12-epoxyerythromycin A A mixture of 2 g (2 mmol) of (9S,11S) 2'-O-acetyl-11-(N-benzyloxycarbonyl)amino-9-deoxo-11,12-dideoxy-9,12-epoxy-4"-O-(1'-H 1'-imidazole)thiocarbonylerythromycin A (from Step C), 30 mL of dry toluene and 20 mg of 2,2'-azobisisobutyronitrile was prepared in an oven dried 50 mL flask and flushed with nitrogen. Tri-n-butyltin hydride (2.05 mL, 7.65 mmol) was added at ambient temperature and the reaction mixture heated to 65° C. The reaction mixture was heated at 65° C. for 18 hours, allowed to cool to ambient temperature and washed with 52 mL of a 4.8% aqueous sodium bicarbonate solution containing 1% ammonia. The aqueous layer was back-extracted with roluene. The combined toluene layers were extracted with 3×50 mL of hexane/acetonitrile. The combined acetonitrile layers were dried over sodium sulfate, filtered and concentrated in vacuo to give 1.46 g (84% yield) of the title compound as a white glass. MS EI M/Z: 877 (M+H)$^+$.

Step E (9S,11S)-11-Amino-9-deoxo-4",11,12-trideoxy-9,12-epoxyerythromycin A

To a solution of 1.46 g (1.67 mmol) of (9S,11S)-2'-O-acetyl-11-(N-benzyloxycarbonyl)amino-9-deoxo-4",11,12-trideoxy-9,12-epoxyerythromycin A, from Step D, in 900 mL of methanol was added 10 mL of concentrated aqueous ammonium hydroxide solution and 3 g of Raney nickel. The reaction mixture was hydrogenated at ambient temperature under 4 atmospheres of hydrogen for 22 hours. The reaction mixture was filtered and concentrated in vacuo. The residue was dissolved in 100 mL of methylene chloride and the methylene chloride solution washed with 50 mL of 5% sodium bicarbonate solution. The aqueous layer was back extracted with 3×50 mL of methylene chloride. The combined organic layers were dried over anhydrous sodium sulfate, filtered and concentrated in vacuo. The residue (900 mg) was purified on silica gel pretreated with acetonitrile:ammonium hydroxide (10:0.03). The column was eluted with the above solvent until fifty 26 mL fractions were collected. The solvent was then changed to acetonitrile:ammonium hydroxide (10:0.07). Fractions 110–125 were combined, concentrated and rechromatographed by the same procedure eluting only with acetonitrile:ammonium hydroxide (10:0.03) to give the title compound. MS FAB M/Z: 701 (M+H)$^+$; $^1$H NMR (CDCl$_3$) delta 0.83 (t, 3H, 15), 1.26 (s, 3H, 12), 2.30 (s, 6H, NMe$_2$), 2.51 (dt, 1H, 3'), 2.71 (m, 1H, 2), 3.21 (dd, 1H, 2'), 3.25 (s, 3H, OCH$_3$), 4.45 (d, 1H, 1'), 4.95 (d, 1H, 1"), 5.10 (dd, 1H, 13).

EXAMPLE 34

In-Vitro Antibiotic Activity

The antimicrobial spectra of several of the compounds of the present invention were tested as described below. The results are indicated in Tables 2 and 3.

Twelve petri dishes containing successive aqueous dilutions of the test compounds, mixed with 10 mL of sterilized Brain Heart Infusion (BHI) agar (Difco 0418-01-5), were prepared. Each plate was inoculated with 1:100 (or 1:10 for slow growing strains (primarily Micrococcus and Streptococcus) dilutions of up to 32 different microorganisms, using a Steers replicator block. The inoculated plates were incubated at 35 37° C. for 20–24 hours. In addition, a control plate, using BHI agar containing no test compound, was prepared and incubated at the beginning and the end of each test.

An additional plate containing a compound having known susceptibility patterns for the organisms being tested and belonging to the same antibiotic class as the test compounds was also prepared and incubated as a further control, as well as to provide test-to test comparability. Erythromycin A was used for this purpose.

After incubation, each plate was read. The MIC (minimum inhibitory concentration) is defined as the lowest concentration of test compound yielding no growth, a slight haze, or sparsely isolated colonies on the inoculum spot as compared to the growth control containing no test compound.

TABLE 1

| EXAMPLE | R$_1$ | R$_2$ | R$_3$ | SCHEME | REAGENT | TYPICAL NMR ppm from TMS | | | MASS SPECTRUM (M/Z) |
|---|---|---|---|---|---|---|---|---|---|
| 26A | OH | O(CH$_2$)$_2$NH$_2$ | H | IV | AMMONIA | 9 | 3.65 | dd | 761 |
| | | | | | | 11 | 4.28 | dd | C$_{39}$H$_{72}$N$_2$O$_{12}$ |
| | | | | | | 2' | 3.21 | dd | (761.015) |
| | | | | | | 4" | 2.85 | dd | |

TABLE 1-continued

| EXAMPLE | $R_1$ | $R_2$ | $R_3$ | SCHEME | REAGENT | TYPICAL NMR ppm from TMS | | | MASS SPECTRUM (M/Z) |
|---|---|---|---|---|---|---|---|---|---|
| 26B | OH | O(CH$_2$)$_2$NMe$_2$ | H | IV | HNMe$_2$ | 1''' | 3.70 | m | |
| | | | | | | 2''' | 2.90 | m | 789 |
| | | | | | | 9 | 3.65 | dd | C$_{41}$H$_{76}$N$_2$O$_{12}$ |
| | | | | | | 11 | 4.28 | dd | (789.069) |
| | | | | | | 2' | 3.21 | dd | |
| | | | | | | 4'' | 2.82 | d | |
| | | | | | | 1''' | 3.64 | m | |
| | | | | | | 2''' | 2.55 | m | |
| | | | | | | NMe$_2$ | 2.26 | s | |
| 26C | OH | O(CH$_2$)$_2$NMeBzl | H | IV | N-METHYL BENZYLAMINE | 9 | 3.65 | dd | 865 |
| | | | | | | 11 | 4.28 | dd | C$_{47}$H$_{80}$N$_2$O$_{12}$ |
| | | | | | | 2' | 3.18 | dd | (865.168) |
| | | | | | | 4'' | 2.80 | d | |
| | | | | | | 1''' | 3.75 | m | |
| | | | | | | 2''' | 2.63 | m | |
| | | | | | | NMe | 2.23 | s | |
| | | | | | | NCH$_2$ | 3.49 | d | |
| | | | | | | | 3.55 | d | |
| | | | | | | C$_6$H$_5$ | 7.30 | m | |
| 26D | OH | O(CH$_2$)$_2$NHBzl | H | IV | BENZYLAMINE | 9 | 3.65 | dd | 851 |
| | | | | | | 11 | 4.28 | dd | C$_{46}$H$_{78}$N$_2$O$_{12}$ |
| | | | | | | 2' | 3.17 | dd | (851.141) |
| | | | | | | 4'' | 2.83 | d | |
| | | | | | | 1''' | 3.80 | m | |
| | | | | | | 2''' | 2.85 | m | |
| | | | | | | NCH$_2$ | 3.80 | m | |
| | | | | | | C$_6$H$_5$ | 7.30 | m | |
| 28A | OH | OH | Me | III | LiBH$_4$ | 9 | 3.56 | dd | 732 |
| | | | | | | 11 | 4.28 | dd | C$_{38}$H$_{69}$NO$_{12}$ |
| | | | | | | 13 | 5.07 | dd | (731.973) |
| | | | | | | 1' | 4.36 | d | |
| | | | | | | 2' | 3.19 | dd | |
| | | | | | | 1'' | 4.83 | d | |
| | | | | | | '' | 3.01 | t | |
| | | | | | | 6 OMe | 3.22 | s | |
| 28B | =O | OH | Me | III | DIBAH | 9 | 3.74 | dd | 730 |
| | | | | | | 13 | 5.17 | dd | C$_{38}$H$_{67}$NO$_{12}$ |
| | | | | | | 1' | 4.37 | d | (729.957) |
| | | | | | | 2' | 3.18 | dd | |
| | | | | | | '' | 4.89 | d | |
| | | | | | | 4'' | 3.01 | t | |
| | | | | | | 6 OMe | 3.28 | s | |
| 29A | =O | MeN(CH$_2$)$_2$NMe$_2$ | H | VII | NaBH$_3$CN | 9 | 3.78 | dd | 800 |
| | | | | | | 13 | 5.16 | dd | C$_{42}$H$_{77}$N$_3$O$_{11}$ |
| | | | | | | 1' | 4.37 | d | (800.095) |
| | | | | | | 2' | 3.33 | dd | |
| | | | | | | 1'' | 4.77 | d | |
| | | | | | | 5'' | 4.52 | dq | (J$_{4'',5''}$ = 10 Hz) |
| | | | | | | NMe$_2$ | 2.35 | s | (12 H) |
| | | | | | | NMe | 2.52 | s | (3 H) |
| 29B | =O | NHBzl | H | VII | NaBH$_3$CN | 9 | 3.77 | dd | |
| | | | | | | 13 | 5.11 | dd | C$_{44}$H$_{72}$N$_2$O$_{11}$ |
| | | | | | | 1' | 4.43 | d | (805.071) |
| | | | | | | 2' | 3.30 | dd | |
| | | | | | | 1'' | 4.84 | d | |
| | | | | | | 5'' | 4.11 | dq | (J$_{4'',5''}$ = 10 Hz) |
| | | | | | | Bzl | 3.82 | d | |
| | | | | | | Bzl | 3.94 | d | |
| | | | | | | C$_6$H$_5$ | 7.30 | m | |
| 29C | =O | N-piperidino | H | VII | NaBH$_3$CN | 9 | 3.78 | dd | |
| | | | | | | 13 | 5.17 | dd | C$_{42}$H$_{74}$N$_2$O$_{11}$ |
| | | | | | | 1' | 4.37 | d | (783.065) |
| | | | | | | 2' | 3.33 | dd | |
| | | | | | | 1'' | 4.75 | d | |
| | | | | | | 5'' | 4.47 | dq | (J$_{4'',5''}$ = 10 Hz) |
| 29A | =O | MeN(CH$_2$)$_2$NMe$_2$ | H | VII | NaBH$_3$CN | 9 | 3.78 | dd | 800 |
| | | | | | | 13 | 5.16 | dd | C$_{42}$H$_{77}$N$_3$O$_{11}$ |
| | | | | | | 1' | 4.37 | d | (800.095) |
| | | | | | | 2' | 3.33 | dd | |
| | | | | | | 1'' | 4.77 | d | |
| | | | | | | 5'' | 4.52 | dq | (J$_{4'',5''}$ = 10 Hz) |
| | | | | | | NMe$_2$ | 2.35 | s | (12 H) |
| | | | | | | NMe | 2.52 | s | (3 H) |
| 29B | =O | NHBzl | H | VII | NaBH$_3$CN | 9 | 3.77 | dd | |
| | | | | | | 13 | 5.11 | dd | C$_{44}$H$_{72}$N$_2$O$_{11}$ |
| | | | | | | 1' | 4.43 | d | (805.071) |
| | | | | | | 2' | 3.30 | dd | |
| | | | | | | 1'' | 4.84 | d | |
| | | | | | | 5'' | 4.11 | dq | (J$_{4'',5''}$ = 10 Hz) |

TABLE 1-continued

| EXAMPLE | R₁ | R₂ | R₃ | SCHEME | REAGENT | TYPICAL NMR ppm from TMS | | | MASS SPECTRUM (M/Z) |
|---|---|---|---|---|---|---|---|---|---|
| | | | | | | Bzl | 3.82 | d | |
| | | | | | | Bzl | 3.94 | d | |
| | | | | | | C₆H₅ | 7.30 | m | |
| 29C | =O | N-piperidino | H | VII | NaBH₃CN | 9 | 3.78 | dd | C₄₂H₇₄N₂O₁₁ |
| | | | | | | 13 | 5.17 | dd | (783.065) |
| | | | | | | 1' | 4.37 | d | |
| | | | | | | 2' | 3.33 | dd | |
| | | | | | | 1" | 4.75 | d | |
| | | | | | | 5" | 4.47 | dq | ($J_{4",5"}$ = 10 Hz) |
| 29D | =O | NMe₂ | H | VII | CH₂O Pd/C | 9 | 3.78 | dd | 743 |
| | | | | | | 13 | 5.15 | dd | C₃₉H₇₀N₂O₁₁ |
| | | | | | | 1' | 4.38 | d | (743.000) |
| | | | | | | 2' | 2.32 | dd | |
| | | | | | | 1" | 4.78 | d | |
| | | | | | | 5" | 4.48 | dq | ($J_{4",5"}$ = 10 Hz) |
| | | | | | | 4"-NMe₂ | 2.51 | s | |
| 29E | =O | N=CHNMe₂ | H | VII | Me₂NCH(OMe)₂ | 9 | 3.77 | dd | 770 |
| | | | | | | 13 | 5.15 | dd | C₄₀H₇₁N₃O₁₁ |
| | | | | | | 1' | 4.43 | d | (770.025) |
| | | | | | | 2' | 3.32 | dd | |
| | | | | | | 1" | 4.85 | d | |
| | | | | | | 5" | 4.51 | dq | ($J_{4",5"}$ = 10 Hz) |
| | | | | | | 4"-NMe₂ | 2.74 | s | |
| | | | | | | N=CH | 7.18 | s | |
| 29F | =O | NHC(O)CH₃ | H | VII | ACETIC ANHYDRIDE | 9 | 3.78 | dd | 757 |
| | | | | | | 13 | 5.15 | dd | C₃₉H₆₈N₂O₁₂ |
| | | | | | | 1' | 4.34 | d | (756.983) |
| | | | | | | 2' | 3.35 | dd | |
| | | | | | | 1" | 4.87 | d | |
| | | | | | | 4" | 3.72 | t | |
| | | | | | | 5" | 4.13 | dq | ($J_{4",5"}$ = 10 Hz) |
| | | | | | | C(O)CH₃ | 2.03 | s | |
| | | | | | | NH | 5.91 | d | |
| 30A | =O | MeN(CH₂)₂NMe₂ | H | VI | NaBH₃CN | 9 | 3.78 | dd | 800 |
| | | | | | | 13 | 5.12 | dd | C₄₂H₇₇N₃O₁₁ |
| | | | | | | 1' | 4.39 | d | (800.095) |
| | | | | | | 2' | 3.35 | dd | |
| | | | | | | 1" | 4.90 | d | |
| | | | | | | 5" | 4.65 | dq | ($J_{4",5"}$ = 2.5 Hz) |
| | | | | | | NMe₂ | 2.42 | s | (12 H) |
| | | | | | | NMe | 2.61 | s | (3 H) |
| 30B | =O | N-piperidino | H | VI | NaBH₃CN | 9 | 3.77 | dd | 783 |
| | | | | | | 13 | 5.11 | dd | C₃₉H₇₀N₂O₁₁ |
| | | | | | | 1' | 4.39 | d | (783.065) |
| | | | | | | 2' | 3.36 | dd | |
| | | | | | | 1" | 4.88 | d | |
| | | | | | | 5" | 4.63 | dq | ($J_{4",5"}$ = 2.5 Hz) |
| 30C | =O | NMe₂ | H | VI | CH₂O Pd/C | 9 | 3.77 | dd | 743 |
| | | | | | | 13 | 5.09 | dd | C₃₉H₇₀N₂O₁₁ |
| | | | | | | 1' | 4.39 | d | (743.000) |
| | | | | | | 2' | 3.30 | dd | |
| | | | | | | 1" | 4.91 | d | |
| | | | | | | 5" | 4.62 | dq | ($J_{4",5"}$ = 3.0 Hz) |
| | | | | | | 4"-NMe₂ | 2.60 | s | |

TABLE 2

IN-VITRO ANTIMICROBIAL ACTIVITY PRIMARY SCREEN

| ORGANISM MIC (microgram/mL) | Ex. 4 | MIC-Std | Ex. 5 | MIC-Std | Ex. 7 | MIC-Std |
|---|---|---|---|---|---|---|
| Staphylococcus aureus ATCC 6538P | 0.2 | 0.2 | 0.39 | 0.2 | 0.2 | 0.2 |
| Staphylococcus aureus CMX 686B | 0.2 | 0.2 | 0.39 | 0.2 | 0.2 | 0.2 |
| Staphylococcus aureus A5177 | 3.1 | 1.56 | 3.1 | 1.56 | 0.39 | 1.56 |
| Staphylococcus aureus 45 | 0.2 | 0.2 | 0.1 | 0.1 | 0.2 | 0.2 |
| Staphylococcus aureus 45 RAR2 | 0.39 | 0.2 | 0.2 | 0.2 | 0.39 | 0.2 |
| Staphylococcus aureus CMX 503A | 0.2 | 0.2 | 0.2 | 0.2 | 0.2 | 0.2 |
| Staphylococcus aureus CMX 553 | 0.2 | 0.2 | 0.1 | 0.2 | 0.2 | 0.2 |
| Staphylococcus epidermidis 3519 | 0.2 | 0.2 | 0.2 | 0.2 | 0.39 | 0.2 |
| Micrococcus luteus ATCC 9341 | 0.05 | 0.05 | <0.05 | 0.05 | 0.05 | 0.02 |
| Micrococcus luteus ATCC 4698 | 0.1 | 0.1 | 0.1 | 0.1 | 0.2 | 0.1 |
| Enterococcus faecium ATCC 8043 | 0.1 | 0.05 | 0.1 | 0.05 | 0.1 | 0.05 |
| Streptococcus bovis A5169 | 0.02 | 0.02 | 0.1 | 0.1 | 0.1 | 0.05 |
| Streptococcus agalactiae CMX 508 | 0.05 | 0.05 | 0.1 | 0.05 | 0.05 | 0.05 |
| Streptococcus pyrogenes EES61 | 0.01 | 0.02 | <0.05 | 0.02 | 0.1 | 0.05 |
| Streptococcus pyrogenes 2548 INDUC | 3.1 | 3.1 | 1.56 | 3.1 | 0.39 | 3.1 |
| Escherichia coli JUHL | 25 | 25 | 100 | 25 | >100 | 50 |
| Escherichia coli SS | 0.2 | 0.2 | 0.2 | 0.2 | 1.56 | 0.39 |
| Escherichia coli DC-2 | 50 | 50 | >100 | 50 | 100 | 50 |

TABLE 2-continued

IN-VITRO ANTIMICROBIAL ACTIVITY PRIMARY SCREEN

| | | | | | | |
|---|---|---|---|---|---|---|
| *Escherichia coli* H560 | 25 | 25 | 100 | 25 | 25 | 12.5 |
| *Enterobacter aerogenes* ATCC 13048 | 50 | 50 | >100 | 50 | 100 | 100 |
| *Klebsiella pneumoniae* ATCC 8045 | 50 | 50 | >100 | 50 | 100 | 50 |
| *Providencia stuartii* CMX 640 | >100 | >100 | >100 | >100 | >100 | >100 |
| *Pseudomonas aeruginosa* BMH10 | 50 | 100 | 100 | 100 | 100 | 100 |
| *Pseudomonas aeruginosa* A5007 | >100 | >100 | >100 | >100 | >100 | >100 |
| *Pseudomonas aeruginosa* K799/WT | 100 | 50 | 100 | 50 | 100 | 50 |
| *Pseudomonas aeruginosa* K799/61 | 0.39 | 0.78 | 1.56 | 0.78 | 0.78 | 1.56 |
| *Pseudomonas cepacia* 2961 | >100 | >100 | 100 | >100 | >100 | >100 |
| *Acinetobacter SP* CMX 669 | 3.1 | 6.2 | 12.5 | 6.2 | 25 | 6.2 |

| ORGANISM MIC (microgram/mL) | Ex. 8 MIC-Std | | Ex. 9 MIC-Std | | Ex. 10 MIC-Std | |
|---|---|---|---|---|---|---|
| *Staphylococcus aureus* ATCC 6538P | 0.2 | 0.2 | 0.39 | 0.2 | 0.39 | 0.2 |
| *Staphylococcus aureus* CMX 686B | 0.2 | 0.2 | 0.39 | 0.2 | 0.39 | 0.2 |
| *Staphylococcus aureus* A5177 | 0.39 | 0.78 | 0.78 | 1.56 | 0.39 | 0.78 |
| *Staphylococcus aureus* 45 | 0.2 | 0.1 | 0.39 | 0.1 | 0.39 | 0.1 |
| *Staphylococcus aureus* 45 RAR2 | 0.2 | 0.2 | 0.78 | 0.2 | 0.39 | 0.2 |
| *Staphylococcus aureus* CMX 503A | 0.2 | 0.1 | 0.39 | 0.2 | 0.39 | 0.1 |
| *Staphylococcus aureus* CMX 553 | 0.1 | 0.2 | 0.39 | 0.2 | 0.39 | 0.2 |
| *Staphylococcus epidermidis* 3519 | 0.2 | 0.2 | 0.39 | 0.2 | 0.39 | 0.2 |
| *Micrococcus luteus* ATCC 9341 | 0.02 | 0.02 | 0.02 | 0.02 | 0.05 | 0.02 |
| *Micrococcus luteus* ATCC 4698 | 0.05 | 0.1 | 0.2 | 0.1 | 0.2 | 0.1 |
| *Enterococcus faecium* ATCC 8043 | 0.05 | 0.05 | 0.1 | 0.05 | 0.2 | 0.05 |
| *Streptococcus bovis* A5169 | 0.05 | 0.05 | <0.005 | 0.02 | 0.2 | 0.05 |
| *Streptococcus agalactiae* CMX 508 | 0.02 | 0.2 | 0.01 | 0.02 | 0.1 | 0.2 |
| *Streptococcus pyrogenes* EES61 | 0.01 | 0.01 | <0.005 | 0.01 | 0.02 | 0.01 |
| *Streptococcus pyrogenes* 2548 INDUC | 0.39 | 3.1 | 6.2 | 3.1 | 0.78 | 3.1 |
| *Escherichia coli* JUHL | 100 | 50 | >100 | 50 | >100 | 50 |
| *Escherichia coli* SS | 0.2 | 0.2 | 0.78 | 0.2 | 0.39 | 0.2 |
| *Escherichia coli* DC-2 | 100 | 50 | >100 | 50 | >100 | 50 |
| *Escherichia coli* H560 | 25 | 12.5 | 50 | 25 | 100 | 12.5 |
| *Enterobacter aerogenes* ATCC 13048 | >100 | 50 | >100 | 100 | >100 | 50 |
| *Klebsiella pneumoniae* ATCC 8045 | 100 | 50 | >100 | 100 | >100 | 50 |
| *Providencia stuartii* CMX 640 | >100 | >100 | >100 | >100 | >100 | >100 |
| *Pseudomonas aeruginosa* BMH10 | 100 | 100 | >100 | 50 | >100 | 100 |
| *Pseudomonas aeruginosa* A5007 | >100 | >100 | >100 | >100 | >100 | >100 |
| *Pseudomonas aeruginosa* K799/WT | >100 | 50 | 100 | 50 | >100 | 50 |
| *Pseudomonas aeruginosa* K799/61 | 0.78 | 1.56 | 3.1 | 0.78 | 1.56 | 1.56 |
| *Pseudomonas cepacia* 2961 | >100 | >100 | >100 | >100 | >100 | >100 |
| *Acinetobacter SP* CMX 669 | 6.2 | 6.2 | 50 | 6.2 | 50 | 6.2 |

| ORGANISM MIC (microgram/mL) | Ex. 11 MIC-Std | | Ex. 12 MIC-Std | | Ex. 13 MIC-Std | |
|---|---|---|---|---|---|---|
| *Staphylococcus aureus* ATCC 6538P | 0.39 | 0.2 | 0.39 | 0.2 | 0.2 | 0.2 |
| *Staphylococcus aureus* CMX 686B | 0.39 | 0.2 | 0.39 | 0.2 | 0.2 | 0.2 |
| *Staphylococcus aureus* A5177 | 0.39 | 1.56 | 0.39 | 1.56 | 0.78 | 1.56 |
| *Staphylococcus aureus* 45 | 0.39 | 0.1 | 0.2 | 0.1 | 0.2 | 0.1 |
| *Staphylococcus aureus* 45 RAR2 | 0.39 | 0.2 | 0.39 | 0.2 | 0.2 | 0.2 |
| *Staphylococcus aureus* CMX 503A | 0.39 | 0.2 | 0.39 | 0.2 | 0.2 | 0.2 |
| *Staphylococcus aureus* CMX 553 | 0.2 | 0.2 | 0.2 | 0.2 | 0.2 | 0.2 |
| *Staphylococcus epidermidis* 3519 | 0.78 | 0.2 | 0.39 | 0.2 | 0.2 | 0.2 |
| *Micrococcus luteus* ATCC 9341 | 0.05 | 0.02 | 0.05 | 0.02 | 0.01 | 0.02 |
| *Micrococcus luteus* ATCC 4698 | 0.1 | 0.1 | 0.39 | 0.1 | 0.05 | 0.1 |
| *Enterococcus faecium* ATCC 8043 | 0.05 | 0.05 | 0.2 | 0.05 | 0.05 | 0.05 |
| *Streptococcus bovis* A5169 | <0.005 | 0.02 | 0.05 | 0.02 | 0.01 | 0.02 |
| *Streptococcus agalactiae* CMX 508 | 0.02 | 0.02 | 0.1 | 0.02 | 0.02 | 0.02 |
| *Streptococcus pyrogenes* EES61 | <0.005 | 0.01 | 0.1 | 0.01 | <0.005 | 0.01 |
| *Streptococcus pyrogenes* 2548 INDUC | 0.78 | 3.1 | 3.1 | 3.1 | 0.78 | 3.1 |
| *Escherichia coli* JUHL | >100 | 50 | >100 | 50 | 50 | 50 |
| *Escherichia coli* SS | 0.78 | 0.2 | 3.1 | 0.2 | 0.2 | 0.2 |
| *Escherichia coli* DC-2 | >100 | 50 | >100 | 50 | 50 | 50 |
| *Escherichia coli* H560 | >100 | 25 | >100 | 25 | 12.5 | 25 |
| *Enterobacter aerogenes* ATCC 13048 | >100 | 100 | >100 | 100 | 100 | 100 |
| *Klebsiella pneumoniae* ATCC 8045 | >100 | 100 | >100 | 100 | 25 | 100 |
| *Providencia stuartii* CMX 640 | >100 | >100 | >100 | >100 | >100 | >100 |
| *Pseudomonas aeruginosa* BMH10 | >100 | 50 | >100 | 50 | 100 | 50 |
| *Pseudomonas aeruginosa* A5007 | >100 | >100 | >100 | >100 | >100 | >100 |
| *Pseudomonas aeruginosa* K799/WT | 100 | 50 | 100 | 50 | 100 | 50 |
| *Pseudomonas aeruginosa* K799/61 | 3.1 | 0.78 | 3.1 | 0.78 | 1.56 | 0.78 |
| *Pseudomonas cepacia* 2961 | >100 | >100 | >100 | >100 | >100 | >100 |
| *Acinetobacter SP* CMX 669 | 50 | 6.2 | >100 | 6.2 | 25 | 6.2 |

| ORGANISM MIC (microgram/mL) | Ex. 14 MIC-Std | | Ex. 15 MIC-Std | | Ex. 16 MIC-Std | |
|---|---|---|---|---|---|---|
| *Staphylococcus aureus* ATCC 6538P | 0.39 | 0.2 | 0.39 | 0.2 | 0.39 | 0.2 |
| *Staphylococcus aureus* CMX 686B | 0.39 | 0.2 | 0.39 | 0.2 | 0.39 | 0.2 |
| *Staphylococcus aureus* A5177 | 3.1 | 1.56 | 1.56 | 1.56 | 0.39 | 1.56 |
| *Staphylococcus aureus* 45 | 0.39 | 0.2 | 0.39 | 0.1 | 0.39 | 0.1 |
| *Staphylococcus aureus* 45 RAR2 | 0.39 | 0.2 | 0.39 | 0.2 | 0.78 | 0.2 |
| *Staphylococcus aureus* CMX 503A | 0.39 | 0.2 | 0.39 | 0.2 | 0.39 | 0.2 |

TABLE 2-continued

IN-VITRO ANTIMICROBIAL ACTIVITY PRIMARY SCREEN

| | | | | | | |
|---|---|---|---|---|---|---|
| Staphylococcus aureus CMX 553 | 0.2 | 0.2 | 0.2 | 0.2 | 0.39 | 0.2 |
| Staphylococcus epidermidis 3519 | 0.39 | 0.2 | 0.2 | 0.2 | 0.39 | 0.2 |
| Micrococcus luteus ATCC 9341 | 0.05 | 0.02 | 0.01 | 0.02 | 0.02 | 0.02 |
| Micrococcus luteus ATCC 4698 | 0.1 | 0.1 | 0.05 | 0.1 | 0.05 | 0.1 |
| Enterococcus faecium ATCC 8043 | 0.1 | 0.05 | 0.1 | 0.05 | 0.05 | 0.05 |
| Streptococcus bovis A5169 | 0.1 | 0.05 | 0.01 | 0.02 | <0.005 | 0.02 |
| Streptococcus agalactiae CMX 508 | 0.05 | 0.05 | 0.02 | 0.02 | 0.02 | 0.02 |
| Streptococcus pyrogenes EES61 | 0.05 | 0.05 | 0.02 | 0.01 | <0.005 | 0.01 |
| Streptococcus pyrogenes 2548 INDUC | 3.1 | 3.1 | 6.2 | 3.1 | 3.1 | 3.1 |
| Escherichia coli JUHL | 25 | 50 | 12.5 | 50 | >100 | 50 |
| Escherichia coli SS | 0.2 | 0.39 | 0.1 | 0.2 | 0.39 | 0.2 |
| Escherichia coli DC-2 | 25 | 50 | 6.2 | 50 | >100 | 50 |
| Escherichia coli H560 | 12.5 | 12.5 | 3.1 | 25 | >100 | 25 |
| Enterobacter aerogenes ATCC 13048 | >100 | 100 | 50 | 100 | >100 | 100 |
| Klebsiella pneumoniae ATCC 8045 | 100 | 50 | 25 | 100 | >100 | 100 |
| Providencia stuartii CMX 640 | >100 | >100 | >100 | >100 | >100 | >100 |
| Pseudomonas aeruginosa BMH10 | 50 | 100 | 50 | 50 | 100 | 50 |
| Pseudomonas aeruginosa A5007 | >100 | >100 | >100 | >100 | >100 | >100 |
| Pseudomonas aeruginosa K799/WT | >100 | 50 | 100 | 50 | 100 | 50 |
| Pseudomonas aeruginosa K799/61 | 1.56 | 1.56 | 0.78 | 0.78 | 3.1 | 0.78 |
| Pseudomonas cepacia 2961 | >100 | >100 | >100 | >100 | >100 | >100 |
| Acinetobacter SP CMX 669 | 12.5 | 6.2 | 6.2 | 6.2 | 50 | 6.2 |

| ORGANISM MIC (microgram/mL) | Ex. 17 MIC-Std | | Ex. 18 MIC-Std | | Ex. 19 MIC-Std | |
|---|---|---|---|---|---|---|
| Staphylococcus aureus ATCC 6538P | 0.2 | 0.1 | 0.2 | 0.2 | 0.2 | 0.2 |
| Staphylococcus aureus CMX 686B | 0.39 | 0.2 | 0.2 | 0.2 | 0.2 | 0.2 |
| Staphylococcus aureus A5177 | 12.5 | 1.56 | 0.78 | 0.78 | 0.39 | 0.78 |
| Staphylococcus aureus 45 | 0.78 | 0.1 | 0.2 | 0.1 | 0.2 | 0.1 |
| Staphylococcus aureus 45 RAR2 | 0.39 | 0.2 | 0.39 | 0.2 | 0.39 | 0.2 |
| Staphylococcus aureus CMX 503A | 0.39 | 0.1 | 0.2 | 0.2 | 0.2 | 0.2 |
| Staphylococcus aureus CMX 553 | 0.39 | 0.1 | 0.2 | 0.2 | 0.2 | 0.2 |
| Staphylococcus epidermidis 3519 | 0.78 | 0.1 | 0.39 | 0.2 | 0.2 | 0.2 |
| Micrococcus luteus ATCC 9341 | 0.05 | 0.02 | 0.1 | 0.02 | 0.01 | 0.02 |
| Micrococcus luteus ATCC 4698 | 0.2 | 0.1 | 0.1 | 0.1 | 0.1 | 0.1 |
| Enterococcus faecium ATCC 8043 | 0.2 | 0.05 | 0.2 | 0.05 | 0.05 | 0.05 |
| Streptococcus bovis A5169 | 0.05 | 0.01 | 0.1 | 0.05 | 0.1 | 0.05 |
| Streptococcus agalactiae CMX 508 | 0.02 | 0.02 | 0.05 | 0.05 | 0.02 | 0.05 |
| Streptococcus pyrogenes EES61 | 0.02 | 0.01 | 0.02 | 0.01 | <0.005 | 0.01 |
| Streptococcus pyrogenes 2548 INDUC | 1.56 | 1.56 | 1.56 | 1.56 | 3.1 | 1.56 |
| Escherichia coli JUHL | 50 | 25 | >100 | 50 | >100 | 50 |
| Escherichia coli SS | 0.2 | 0.2 | 1.56 | 0.2 | 0.78 | 0.2 |
| Escherichia coli DC-2 | 50 | 50 | >100 | 50 | 50 | 50 |
| Escherichia coli H560 | 25 | 12.5 | >100 | 12.5 | 6.2 | 12.5 |
| Enterobacter aerogenes ATCC 13048 | 50 | 100 | >100 | 100 | 100 | 100 |
| Klebsiella pneumoniae ATCC 8045 | 25 | 50 | >100 | 100 | 25 | 100 |
| Providencia stuartii CMX 640 | >100 | >100 | >100 | >100 | >100 | >100 |
| Pseudomonas aeruginosa BMH10 | 25 | 100 | >100 | 100 | 50 | 100 |
| Pseudomonas aeruginosa A5007 | >100 | >100 | >100 | >100 | >100 | >100 |
| Pseudomonas aeruginosa K799/WT | 25 | 50 | >100 | 100 | 100 | 100 |
| Pseudomonas aeruginosa K799/61 | 0.78 | 0.78 | 6.2 | 1.56 | 0.78 | 1.56 |
| Pseudomonas cepacia 2961 | >100 | >100 | >100 | >100 | >100 | >100 |
| Acinetobacter SP CMX 669 | 50 | 3.1 | >100 | 6.2 | 1.56 | 6.2 |

TABLE 3

IN-VITRO ANTIMICROBIAL ACTIVITY PRIMARY SCREEN

| ORGANISM MIC (microgram/mL) | Ex. 20 MIC-Std | | Ex. 21 MIC-Std | | Ex. 22 MIC-Std | | Ex. 27 MIC-Std | |
|---|---|---|---|---|---|---|---|---|
| Staphylococcus aureus ATCC 6538P | 0.2 | 0.2 | 0.2 | 0.2 | 0.2 | 0.1 | 0.39 | 0.1 |
| Staphylococcus aureus A5177 | 0.78 | 1.56 | 1.56 | 1.56 | 1.56 | 1.56 | 0.39 | 0.1 |
| Staphylococcus aureus 45 | 0.2 | 0.1 | 0.1 | 0.1 | 0.1 | 0.1 | 3.1 | 0.78 |
| Staphylococcus aureus 45 RAR2 | 0.39 | 0.2 | 0.2 | 0.2 | 0.2 | 0.2 | 0.39 | 0.39 |
| Staphylococcus aureus 642A | 0.39 | 0.2 | 0.2 | 0.2 | 0.2 | 0.2 | 0.39 | 0.1 |
| Staphylococcus aureus NCTC 10649 | 0.39 | 0.2 | 0.2 | 0.1 | 0.2 | 0.1 | 0.39 | 0.1 |
| Staphylococcus aureus CMX 553 | 0.2 | 0.2 | 0.2 | 0.1 | 0.2 | 0.1 | 0.39 | 0.1 |
| Staphyloccus epidermidis 3519 | 0.2 | 0.2 | 0.2 | 0.1 | 0.2 | 0.1 | 0.39 | 0.1 |
| Micrococcus luteus ATCC 9341 | 0.02 | 0.02 | =<0.005 | 0.02 | =<0.005 | 0.02 | 0.05 | 0.02 |
| Micrococcus luteus ATCC 4698 | 0.1 | 0.1 | 0.05 | 0.1 | 0.05 | 0.1 | 0.2 | 0.1 |
| Enterococcus faecium ATCC 8043 | 0.05 | 0.05 | 0.05 | 0.05 | 0.05 | 0.05 | 0.1 | 0.05 |
| Streptococcus bovis A5169 | =<.005 | 0.01 | 0.01 | 0.01 | 0.01 | 0.01 | 0.05 | 0.01 |
| Streptococcus agalactiae CMX 508 | 0.02 | 0.05 | 0.01 | 0.05 | 0.01 | 0.05 | 0.05 | 0.02 |
| Streptococcus pyrogenes EES61 | =<.005 | 0.01 | 0.01 | 0.01 | 0.01 | 0.01 | 0.05 | 0.01 |
| Streptococcus pyrogenes 2548 INDUC | 0.78 | 1.56 | 1.56 | 1.56 | 1.56 | 1.56 | 100 | 3.1 |
| Escherichia coli JUHL | 3.1 | 50 | 1.56 | 25 | 1.56 | 25 | >100 | 25 |
| Escherichia coli SS | 0.05 | 0.2 | 0.1 | 0.2 | 0.1 | 0.2 | 0.78 | 0.2 |
| Escherichia coli DC-2 | 3.1 | 50 | 3.1 | 50 | 3.1 | 50 | >100 | 25 |
| Escherichia coli H560 | 1.56 | 25 | 0.78 | 12.5 | 0.78 | 12.5 | 100 | 12.5 |
| Enterobacter aerogenes ATCC 13048 | 12.5 | 100 | 6.2 | 50 | 6.2 | 50 | >100 | 50 |

TABLE 3-continued

IN-VITRO ANTIMICROBIAL ACTIVITY PRIMARY SCREEN

| | | | | | | | | |
|---|---|---|---|---|---|---|---|---|
| Klebsiella pneumoniae ATCC 8045 | 1.56 | 50 | 1.56 | 25 | 1.56 | 25 | >100 | 50 |
| Providencia stuartii CMX 640 | >100 | >100 | >100 | >100 | >100 | >100 | >100 | >100 |
| Pseudomonas aeruginosa BMH10 | 25 | 100 | 12.5 | 50 | 12.5 | 50 | 100 | 25 |
| Pseudomonas aeruginosa A5007 | >100 | >100 | >100 | >100 | >100 | >100 | >100 | >100 |
| Pseudomonas aeruginosa K799/WT | 50 | 50 | 100 | 100 | 100 | 100 | >100 | 50 |
| Pseudomonas aeruginosa K799/61 | .78 | 1.56 | 0.39 | 1.56 | 0.39 | 1.56 | | |
| Pseudomonas cepacia 2961 | >100 | >100 | >100 | 100 | >100 | 100 | >100 | >100 |
| Acinetobacter SP CMX 669 | 1.56 | 6.2 | 0.39 | 3.1 | 0.39 | 3.1 | 25 | 3.1 |

| ORGANISM MIC (microgram/mL) | Ex. 28A | MIC-Std | Ex. 28B | MIC-Std | Ex. 31 | MIC-Std | Ex. 32 | MIC-Std |
|---|---|---|---|---|---|---|---|---|
| Staphylococcus aureus ATCC 6538P | 0.2 | 0.2 | 0.39 | 0.1 | 0.05 | 0.1 | 0.1 | 0.1 |
| Staphylococcus aureus A5177 | 0.2 | 0.2 | 0.39 | 0.1 | 50 | 3.1 | >100 | 3.1 |
| Staphylococcus aureus 45 | 3.1 | 1.56 | 3.1 | 0.78 | 0.05 | 0.1 | 0.2 | 0.1 |
| Staphylococcus aureus 45 RAR2 | 0.2 | 0.2 | 0.39 | 0.1 | 0.05 | 0.2 | 0.39 | 0.2 |
| Staphylococcus aureus 642A | 0.2 | 0.2 | 0.39 | 0.2 | 0.05 | 0.2 | 0.1 | 0.2 |
| Staphylococcus aureus NCTC 10649 | 0.2 | 0.2 | 0.39 | 0.1 | 0.05 | 0.2 | 0.1 | 0.2 |
| Staphylococcus aureus CMX 553 | 0.2 | 0.2 | 0.39 | 0.1 | 0.05 | 0.2 | 0.2 | 0.2 |
| Staphyloccus epidermidis 3519 | 0.2 | 0.2 | 0.39 | 0.1 | 0.05 | 0.1 | 0.2 | 0.1 |
| Micrococcus luteus ATCC 9341 | 0.05 | 0.05 | 0.05 | 0.02 | 0.02 | 0.02 | 0.05 | 0.02 |
| Micrococcus luteus ATCC 4698 | 0.1 | 0.2 | 0.1 | 0.1 | 0.05 | 0.1 | 0.2 | 0.1 |
| Enterococcus faecium ATCC 8043 | 0.05 | 0.05 | 0.1 | 0.05 | 0.05 | 0.05 | 0.2 | 0.05 |
| Streptococcus bovis A5169 | 0.02 | 0.02 | 0.05 | 0.02 | 0.05 | 0.01 | 0.05 | 0.01 |
| Streptococcus agalactiae CMX 508 | 0.05 | 0.05 | 0.02 | 0.02 | 0.02 | 0.05 | 0.05 | 0.05 |
| Streptococcus pyogenes EES61 | 0.02 | 0.02 | 0.02 | 0.01 | 0.02 | 0.01 | 0.02 | 0.01 |
| Streptococcus pyogenes 2548 INDUC | 3.1 | 3.1 | 3.1 | 3.1 | 0.78 | 1.56 | 0.78 | 1.56 |
| Escherichia coli JUHL | 25 | 25 | >100 | 50 | 100 | 25 | 100 | 25 |
| Escherichia coli SS | 0.2 | 0.2 | 0.39 | 0.2 | 0.2 | 0.2 | 0.2 | 0.2 |
| Escherichia coli DC-2 | 25 | 25 | >100 | 50 | 100 | 50 | 100 | 50 |
| Escherichia coli H560 | 25 | 25 | >100 | 25 | 50 | 25 | 100 | 25 |
| Enterobacter aerogenes ATCC 13048 | 50 | 50 | >100 | 50 | 100 | 50 | 100 | 50 |
| Klebsiella pneumoniae ATCC 8045 | 50 | 50 | >100 | 50 | 100 | 25 | 50 | 25 |
| Providencia stuartii CMX 640 | >100 | >100 | >100 | >100 | >100 | >100 | >100 | >100 |
| Pseudomonas aeruginosa BMH10 | 50 | 50 | 50 | 100 | 50 | 50 | 100 | 50 |
| Pseudomonas aeruginosa A5007 | >100 | >100 | >100 | >100 | >100 | >100 | >100 | >100 |
| Pseudomonas aeruginosa K799/WT | >100 | 100 | >100 | 50 | 100 | 50 | 50 | 50 |
| Pseudomonas aeruginosa K799/61 | 0.78 | 1.56 | 3.1 | 0.78 | 1.56 | 0.78 | 0.78 | 0.78 |
| Pseudomonas cepacia 2961 | >100 | >100 | >100 | 100 | >100 | >100 | >100 | >100 |
| Acinetobacter SP CMX 669 (86:0168P) | 6.2 | 6.2 | 12.5 | 3.1 | 25 | 3.1 | 100 | 3.1 |

EXAMPLE 35

In-Vivo Antibacterial Activity

An acute mouse protection test was conducted on ten mice with each of three concentrations of selected compounds of the invention. Each concentration was a four-fold dilution of the previous concentration. The initial concentration will vary with the microorganism with which the mouse is challenged. Mouse mortality was used to calculate an $ED_{50}$ value, i.e., the dose of drug required to protect 50% of the test animals against death due to the inoculum challenge.

The acute mouse protection test was conducted on female, Swiss albino mice, 18–20 grams in weight. The mice were injected intraperitoneally with an 18-hour culture of the indicated test organism which was diluted sufficiently to provide the desired $LD_{50}$ value. The desired infecting dose was within the range of from about 10 to 1000 times the $LD_{50}$. Preferably, the infecting dose is 100 times the $LD_{50}$. To check the potency of the inoculum, a titration of the indicated test organism was carried out in control animals. The titration determines the $LD_{50}$ for a particular microorganism. The treatment groups of animals were dosed orally, by gavage, or subcutaneously with the test compounds at 1 and 5 hours post-infection and observed for 7 days. The $ED_{50}$ were calculated using the mortality data collected. The results are indicated in Table 4 below, and demonstrate the effectiveness of the inventive compounds in treating infection.

TABLE 4

IN-VIVO MOUSE PROTECTION ASSAY
$ED_{50}$ mg/kg

| | Staphylococcus aureus (NCTC 10649) | | Streptococcus pyogenes C-203 | | Streptococcus pneumoniae (ATCC 6303) | | Haemophilus influenzae (ATCC 43095) | |
|---|---|---|---|---|---|---|---|---|
| Example | Oral | Subcutaneous | Oral | Subcutaneous | Oral | Subcutaneous | Oral | Subcutaneous |
| 4 | 55.0 | 22.6 | 20 | 3.3 | 20.4 | 1.3 | 237.8 | 11.3 |
| Std* | 95.8 | 12.9 | 31.1 | 1.9 | 29.9 | 3.9 | 67 | 29.7 |
| 5 | 25.2 | 22.6 | 3.9 | 1.7 | 23.7 | <0.4 | — | — |
| Std* | 58.1 | 8.3 | 21.4 | 1.8 | 28.2 | 1.6 | — | — |
| 15 | — | 30.1 | 47.9 | 5.0 | 37.3 | 4.0 | — | — |
| 13 | 126.2 | 39.6 | 51.5 | 9.3 | 84.8 | 4.0 | — | — |
| Std* | 91.8 | 10.9 | 64.6 | 7.3 | 33.6 | 2.1 | — | — |
| 19 | 75.4 | 20.7 | 28.9 | 2.5 | <9.4 | 1.1 | 101.4 | — |

TABLE 4-continued

| | IN-VIVO MOUSE PROTECTION ASSAY ED$_{50}$ mg/kg | | | | | | | |
|---|---|---|---|---|---|---|---|---|
| | Staphylococcus aureus (NCTC 10649) | | Streptococcus pyogenes C-203 | | Streptococcus pneumoniae (ATCC 6303) | | Haemophilus influenzae (ATCC 43095) | |
| Example | Oral | Subcutaneous | Oral | Subcutaneous | Oral | Subcutaneous | Oral | Subcutaneous |
| Std* | 123.2 | 11.6 | 53.3 | 6.4 | 13.8 | 2.2 | 251.8 | — |

*Standard-erythromycin

EXAMPLE 36

Pharmacokinetic Evaluation in Dogs

Selected compounds of the present invention were formulated as solutions in dilute lactobionic acid at a concentration of 10 or 20 mg/ml. Groups of two or three dogs were given a 10 mg macrolide/kg intravenous bolus or oral dose (by gavage). Plasma samples, obtained at selected time points from 15 minutes to 32 hours after dosing, were assayed using reverse phase HPLC with electrochemical detection (parent drug) and microbiological assay (total microbiological activity). Plasma concentration time curves were subjected to multi exponential curve fitting to determine terminal elimination half life values. Area under the curve (AUC) values, calculated by the trapezoidal method, were used to calculate absolute bioavailability. The results are indicated in Table 5 below.

TABLE 5

Pharmacokinetic Parameters of Selected Macrolides in Dog after a 10 mg/kg Dose

| | | IV | Oral | | | |
|---|---|---|---|---|---|---|
| Compound | Assay | t½* (hour) | t½* (hour) | Cmax** (mcg/ml) | Tmax*** (hour) | % ABS**** |
| Ery. A++ | Micro | 1.4 | 2.0 | 2.5 | 0.3 | 72 |
| Ex. 4 | Micro | 2.9 | 2.7 | 4.3 | 0.4 | 75 |
| | HPLC | 2.9 | 2.9 | 3.9 | 0.25 | 69 |
| Ex. 5 | Micro | 14.7 | 10.5 | 2.5 | | 76 |
| | HPLC | 12.2 | 10.2 | 2.5 | 4 | 81 |
| Ex. 19 | Micro | 6.6 | 5.8 | 3.3 | 0.4 | 67 |
| | HPLC | 7.5 | 8.1 | 3.2 | 0.25 | 59 |
| Ex. 13 | Micro | 18.3 | 9.1 | 1.7 | 0.4 | 58 |
| | HPLC | 9.9 | 9.6 | 1.6 | 0.4 | 68 |
| Ex. 22 | Micro | 10.2 | 9.8 | 3.5 | 0.6 | 57 |
| | HPLC | 9.3 | 11.5 | 3.2 | 0.5 | 43 |

*Biological half life
**Maximum concentration in blood
***Time to achieve maximum concentration in blood
****Percent absorbance
++Erythromycin A

EXAMPLE 37

Treatment of Induced Otitis Media

The effectiveness of one of the compounds of the present invention in treating otitis media was examined as desribed below. A five hour log phase culture of Haemophilus influenzae ATCC 43095 was prepared in brain heart infusion broth (BHIB) supplemented with 4% Fildes enrichment and 0.001% nicotinamide adenine dinucleotide (NAD; commerically available from Sigma Chemical Co., St. Louis, Missouri). Female mongolian gerbils weighing from about 40 g to about 50 g Tumblebrook Farms, West Brookfield, Massachusetts) were anesthetized with diethyl ether and injected percutaneously into the superior posterior chamber of the middle ear bulla with a 0.02 mL inoculum containing approximately 10$^6$ bacteria.

Immediately prior to treatment with the test compounds, middle ear aspirates from five gerbils were obtained as described below and cultured to determine the level of infection at the onset of therapy. The test compounds produced by Example 19, (9S,11S)-11-Amino-9-deoxo-11,12-deoxy-9,12-epoxyerythromycin A, was administered orally by gavage in a 0.5 mL volume beginning 17 hours post infection and continuing three times daily for two days to groups of five gerbils. As a standard, a second group of gerbils was similarly treated using erythromycin. Eighteen hours after the final treatment, the gerbils were euthanized, 0.02 mL of BHIB injected into the middle ear bulla through the tympanic membrane, and middle ear aspirates collected and cultured.

The aspirates were diluted in BHIB and plated in duplicate onto chocolate agar. Colonies were counted after overnight incubation, and bacterial counts were expressed as colony forming units (CFUs) per middle ear. The minimum number of bacteria detectable by this method was 100 CFUs. Bacterial counts from the treated animals were compared with untreated controls and the 50% effective dose (ED$_{50}$) in mg/kg required to reduce CFUs by 90% was calculated by regression analysis for each test compound. Gerbils were considered cured of infection if no bacteria were removed from undiluted middle ear aspirates.

Using the above procedures, the ED$_{50}$ of the test compound was found to be 46.5 mg/kg while that of erythromycin was shown to be greater than 300 mg/kg. These results demonstrate the efficacy of the inventive compounds in the treatment of middle ear infection.

This invention has been described in terms of specific embodiments set forth in detail. It should be understood, however, that these embodiments are presented by way of illustration only, and that the invention is not necessarily limited thereto. For example, although erythromycin A is described herein, it will be appreciated that there are minor structural differences between the erythromycins A and C. Therefore, the reactions and products of this invention are applicable to both erythromycin A and C. Modifications and variations within the spirit and scope of the claims that follow will be readily apparent from this disclosure, as those skilled in the art will appreciate.

What is claimed is:

1. A compound having the structure:

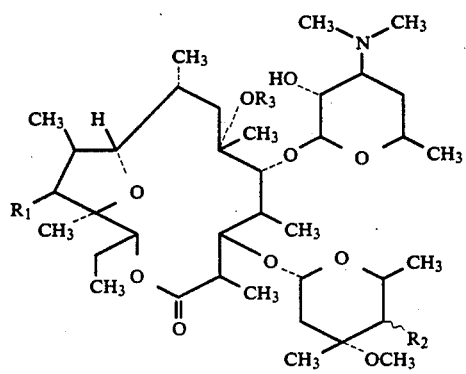

wherein $R_1$ is an oxo, oxime, hydroxy or amino group at the 11 position;

$R_2$ is hydrogen, an oxygen-containing group selected from the group consisting of hydroxy, oxime, $C_1$— to —$C_8$ alkanoyloxy, $C_1$— to —$C_8$ aminoalkoxy, aminocarbonyloxy and carbonate, or a nitrogen-containing group selected from the group consisting of amino, oxime, imine and carbamyl at the 4″ position; and $R_3$ is hydrogen or methyl;

or a pharmaceutically acceptable salt thereof.

2. An antibacterial composition comprising a therapeutically effective amount of an erythromycin derivative as defined in claim 1 in combination with a pharmaceutically acceptable carrier.

3. A method of treating bacterial infections in mammals, comprising administering to the mammal in need thereof a therapeutically effective amount of an erythromycin derivative as defined in claim 1.

4. A compound selected from the group consisting of:
(9S,11S)-9-Deoxo-12-deoxy-9,12-epoxyerythromycin A;
(9S)-9-Deoxo-11,12-dideoxy 9,12-epoxy-11-oxoerythromycin A;
(4″R,9S)-9-Deoxo-4″,11,12-trideoxy -9,12-epoxy-11-oxo-4″-[[(phenylmethoxy)carbonyl]amino]erythromycin A;
(4″R,9S)-4″-Amino-9-deoxo-4″, 11,12-trideoxy-9,12-epoxy-11-oxoerythromycin A;
(4″R,9S)-9-Deoxo-4″,11,12-trideoxy-9,12-epoxy-4″-[[(dimethyamino)methylene]amino]-11-oxoerythromycin A;
(4″R,9S)-4″-Acetylamino-9-deoxo-4″,11,12-trideoxy-9,12-epoxy-11-oxoerythromycin A;
(4″R,9S)-9-Deoxo-4″,11,12-trideoxy-9,12-epoxy-4″-[(methylsulphonyl)amino]-11-oxoerythromycin A;
(4″R,9S)-9-Deoxo-4″,11,12-trideoxy-9,12-epoxy-11-oxo-4″-[(phenylmethyl)amino]erythromycin A;
(4″R,9S,11S)-4″-Amino-9-deoxo-4″,12-dideoxy-9,12-epoxyerythromycin A;
(4″S,9S)-4″-Amino-9-deoxo-4″,11,12-trideoxy-9,12-epoxy-11-oxoerythromycin A;
(4″S,9S,11S)-4″-Amino-9-deoxo-4″,12-dideoxy-9,12-epoxyerythromycin A;
(4″S,9S)-9-Deoxo-4″,11,12-trideoxy-9,12-epoxy-4″-(methylsulfonyl)amino-11-oxoerythromycin A;
(9S,11S)-4″-O-aminocarbonyl-9-deoxo-12-deoxy-9,12-epoxyerythromycin A;
(9S)-9-Deoxo-11,12-dideoxy-9,12-epoxy-11-hydroxyiminoerythromycin;
(9S,11S)-11-Amino-9-deoxo-11,12-deoxy-9,12-epoxyerythromycin A;
(9S,11S)-11-Amino-9-deoxo-4″,11,12-trideoxy-9,12-epoxyerythromycin A
(4″R,9S,11S)-4″,11-Diamino-9-deoxo-4″,11,12-trideoxy-9,12-epoxyerythromycin A;
(4″R,9S)-9-Deoxo-11,12-dideoxy-9,12-epoxy-11-oxoerythromycin A;
(4″S,9S,11S)-4″,11-Diamino-9-deoxo-4″,11,12-trideoxy-9,12-epoxyerythromycin A;
(9S,11S)-4″-O-Acetyl-9-deoxo-12-deoxy-9,12-epoxyerythromycin A;
(9S)-4″-O-Aminocarbonyl-9-deoxo-11,12-dideoxy-9,12-epoxy-11-oxoerythromycin A;
(4″S,9S)-4″-[(Aminocarbonyl)amino]-9-deoxo-4″,11,12-trideoxy-9,12-epoxy-11-oxoerythromycin A; and pharmaceutically acceptable salts thereof.

5. A compound having the structure:

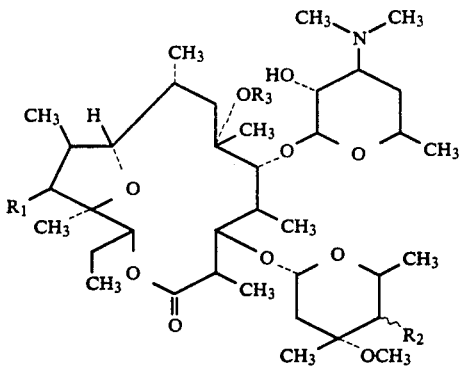

wherein $R_2$ is hydroxy, $R_3$ is hydrogen and $R_1$ is selected from the group consisting of oxo and hydroxy.

* * * * *